(12) United States Patent
Laird et al.

(10) Patent No.: US 12,098,365 B2
(45) Date of Patent: Sep. 24, 2024

(54) MODIFIED MAMMALIAN CELLS

(71) Applicant: GENENTECH, INC., South San Francisco, CA (US)

(72) Inventors: Michael Wilson Laird, South San Francisco, CA (US); Shahram Misaghi, South San Francisco, CA (US); Amy Shen, South San Francisco, CA (US); Anthony Tomlinson, South San Francisco, CA (US); Inn Huam Yuk, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 17/213,611

(22) Filed: Mar. 26, 2021

(65) Prior Publication Data

US 2021/0309989 A1     Oct. 7, 2021

Related U.S. Application Data

(60) Provisional application No. 63/155,225, filed on Mar. 1, 2021, provisional application No. 63/128,419, filed on Dec. 21, 2020, provisional application No. 63/000,464, filed on Mar. 26, 2020.

(51) Int. Cl.
  C12N 15/10    (2006.01)
  C12N 5/071    (2010.01)

(52) U.S. Cl.
  CPC ......... *C12N 15/102* (2013.01); *C12N 5/0682* (2013.01); *C12N 2510/00* (2013.01)

(58) Field of Classification Search
  CPC .................................................. C12N 5/0682
  See application file for complete search history.

(56) References Cited

U.S. PATENT DOCUMENTS

| | | |
|---|---|---|
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,122,469 A | 6/1992 | Mather et al. |
| 5,208,020 A | 5/1993 | Chari et al. |
| 5,399,346 A | 3/1995 | Anderson et al. |
| 5,500,362 A | 3/1996 | Robinson et al. |
| 5,571,894 A | 11/1996 | Wels et al. |
| 5,587,458 A | 12/1996 | King et al. |
| 5,624,821 A | 4/1997 | Winter et al. |
| 5,648,260 A | 7/1997 | Winter et al. |
| 5,731,168 A | 3/1998 | Carter et al. |
| 5,770,429 A | 6/1998 | Lonberg et al. |
| 5,821,337 A | 10/1998 | Carter et al. |
| 5,869,046 A | 2/1999 | Presta et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,248,516 B1 | 6/2001 | Winter et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,189,826 B2 | 3/2007 | Rodman |
| 7,332,581 B2 | 2/2008 | Presta |
| 7,371,826 B2 | 5/2008 | Presta |
| 7,521,541 B2 | 4/2009 | Eigenbrot et al. |
| 7,527,791 B2 | 5/2009 | Adams et al. |
| 7,855,275 B2 | 12/2010 | Eigenbrot et al. |
| 8,309,300 B2 | 11/2012 | Junutula et al. |
| 9,000,130 B2 | 4/2015 | Bhakta et al. |
| 2003/0157108 A1 | 8/2003 | Presta |
| 2004/0093621 A1 | 5/2004 | Shitara et al. |
| 2004/0110282 A1 | 6/2004 | Kanda et al. |
| 2004/0132140 A1 | 7/2004 | Satoh et al. |
| 2004/0259150 A1 | 12/2004 | Nakamura et al. |
| 2005/0014934 A1 | 1/2005 | Hinton et al. |
| 2005/0031613 A1 | 2/2005 | Nakamura et al. |
| 2007/0061900 A1 | 3/2007 | Murphy et al. |
| 2008/0069820 A1 | 3/2008 | Fuh et al. |
| 2016/0176954 A1 | 6/2016 | Ruike et al. |

FOREIGN PATENT DOCUMENTS

| | | |
|---|---|---|
| EP | 0 307 247 A2 | 3/1989 |
| EP | 0 404 097 A2 | 12/1990 |
| EP | 2 101 823 B1 | 9/2009 |

(Continued)

OTHER PUBLICATIONS

Cristea et al. In vivo cleavage of transgene donors promotes nuclease-mediated targeted integration. Biotechnology and Bioengineering 2013, 110;3:871-880 (Year: 2013).*
Zhang et al. CRISPR/Cas9-mediated gene editing in human iPSC-derived macrophages reveals lysosomal acid lipase function in human macrophages. Arteriosclerosis, Thrombosis, and Vascular Biology 2017, 37:2156-2160. (Year: 2017).*
Han et al. Iron homeostasis determines fate of human pluripotent stem cells via glycerophospholipids-epigenetic circuit. Stem Cells 2019, 37:489-503. (Year: 2019).*
MacDonald et al. Bioinformatic analysis of Chinese hamster ovary host cell protein lipases. AIChE Journal 2018, 64; 12:4247-4254. (Year: 2018).*

(Continued)

*Primary Examiner* — Allison M Fox
*Assistant Examiner* — Jennifer S Spence
(74) *Attorney, Agent, or Firm* — Lawrence S. Graham

(57) ABSTRACT

The present disclosure relates to methods, cells, and compositions for producing a product of interest, e.g., a recombinant protein. In particular, the present disclosure provides improved mammalian cells expressing the product of interest, where the cells (e.g., Chinese Hamster Ovary (CHO) cells) have reduced or eliminated activity, e.g., expression, of certain host cell proteins, e.g., enzymes including, but not limited to, certain lipases, esterases, and/or hydrolases.

14 Claims, 16 Drawing Sheets

Figure 2:
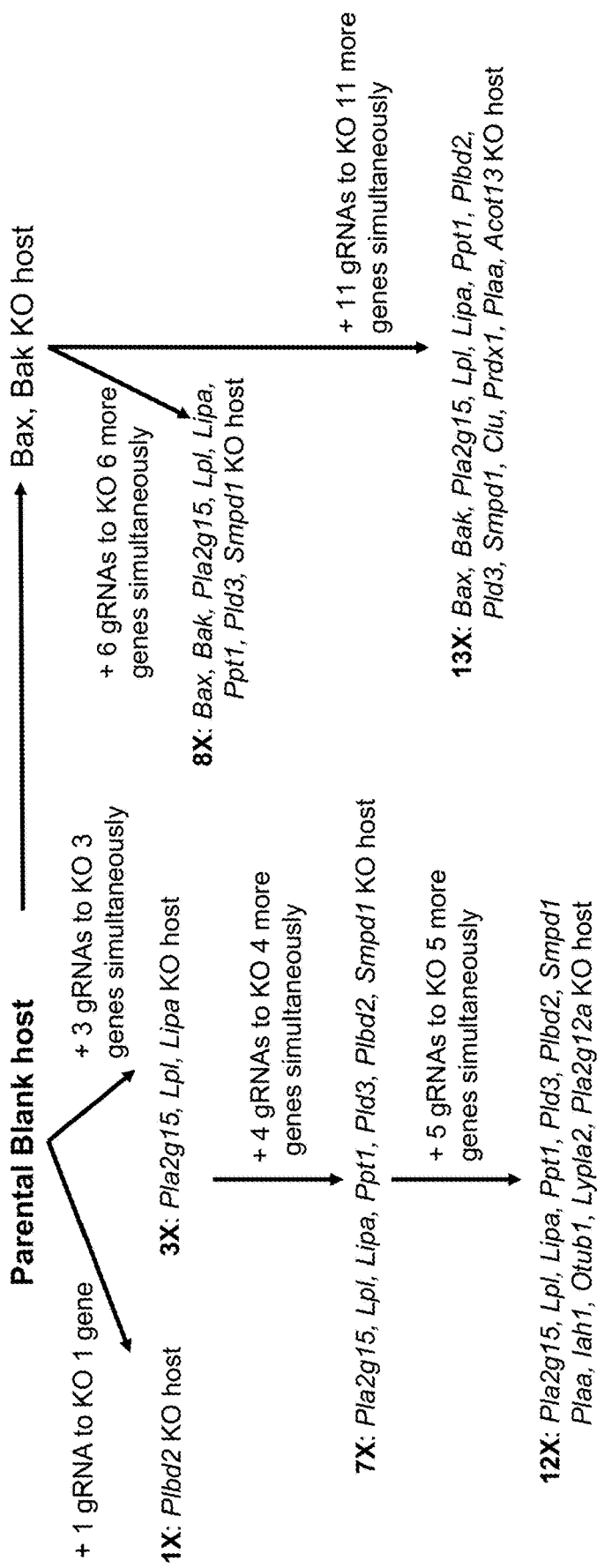

Specification includes a Sequence Listing.

(56) References Cited

FOREIGN PATENT DOCUMENTS

| | | |
|---|---|---|
| WO | WO 87/00195 A1 | 1/1987 |
| WO | WO 90/03430 A1 | 4/1990 |
| WO | WO 93/01161 A1 | 1/1993 |
| WO | WO 93/16185 A2 | 8/1993 |
| WO | WO 94/11026 A2 | 5/1994 |
| WO | WO 94/29351 A2 | 12/1994 |
| WO | WO 97/30087 A1 | 8/1997 |
| WO | WO 98/50431 A2 | 11/1998 |
| WO | WO 98/58964 A1 | 12/1998 |
| WO | WO 99/22764 A1 | 5/1999 |
| WO | WO 99/51642 A1 | 10/1999 |
| WO | WO 99/54342 A1 | 10/1999 |
| WO | WO 01/77342 A1 | 10/2001 |
| WO | WO 03/011878 A2 | 2/2003 |
| WO | WO 03/085107 A1 | 10/2003 |
| WO | WO 2004/009792 A2 | 1/2004 |
| WO | WO 2004/056312 A2 | 7/2004 |
| WO | WO 2004/065540 A2 | 8/2004 |
| WO | WO 2004/106381 A1 | 12/2004 |
| WO | WO 2005/061547 A2 | 7/2005 |
| WO | WO 2005/100402 A1 | 10/2005 |
| WO | WO 2006/029879 A2 | 3/2006 |
| WO | WO 2006/082515 A2 | 8/2006 |
| WO | WO 2007/042261 A2 | 4/2007 |
| WO | WO 2008/024715 A2 | 2/2008 |
| WO | WO 2008/119567 A2 | 10/2008 |
| WO | WO 2009/080251 A1 | 7/2009 |
| WO | WO 2009/080252 A1 | 7/2009 |
| WO | WO 2009/080253 A1 | 7/2009 |
| WO | WO 2009/089004 A1 | 7/2009 |
| WO | WO 2010/112193 A1 | 10/2010 |
| WO | WO 2010/115589 A1 | 10/2010 |
| WO | WO 2010/136172 A1 | 12/2010 |
| WO | WO 2010/145792 A1 | 12/2010 |
| WO | WO 2011/034605 A2 | 3/2011 |
| WO | WO 2012/130831 A1 | 10/2012 |
| WO | WO 2013/026831 A1 | 2/2013 |
| WO | WO 2013/026833 A1 | 2/2013 |
| WO | WO 2013/026839 A1 | 2/2013 |
| WO | WO 2013/120929 A1 | 8/2013 |
| WO | WO 2014/121712 A1 | 8/2014 |
| WO | WO 2014/177460 A1 | 11/2014 |
| WO | WO 2015/095539 A1 | 6/2015 |
| WO | WO 2015/148806 A1 | 10/2015 |
| WO | WO 2015/150447 A1 | 10/2015 |
| WO | WO 2015/153513 A1 | 10/2015 |
| WO | WO 2016/016299 A1 | 2/2016 |
| WO | WO 2016/020309 A1 | 2/2016 |
| WO | WO 2016/040856 A2 | 3/2016 |
| WO | WO 2016/172485 A2 | 10/2016 |
| WO | WO 2018/039499 A9 | 3/2018 |
| WO | WO 2019/126634 A2 | 6/2019 |
| WO | WO 2020/023566 A1 | 1/2020 |
| WO | WO 2021/076620 A1 | 4/2021 |

OTHER PUBLICATIONS

Toutain-Kidd et al. Polysorbate 80 inhibition of Pseudomonas aeruginosa biofilm formation and its cleavage by the secreted lipase LipA. Antimicrobial Agents and Chemotherapy 2009, 53;1:136-145. (Year: 2009).*
Yang et al. Engineered CHO cells for production of diverse, homogeneous glycoproteins. Nature Biotechnology 2015, 33;8:842-845. (Year: 2015).*
ThermoFisher product datasheet, 2010. (Year: 2010).*
Almagro et al., "Humanization of antibodies," Front. Biosci. 13:1619-1633 (2008).
Anderson, "Prospects for Human Gene Therapy," Science 226:401-409 (1984).
Atwell et al., "Stable Heterodimers from Remodeling the Domain Interface of a Homodimer using a Phage Display Library," J. Mol. Biol 270:26-35 (1997).
Baca et al., "Antibody Humanization Using Monovalent Phage Display," J. Biol. Chem. 272:10678-10684 (1997).
Bacac et al., "CEA TCB: A novel head-to-tail 2:1 T cell bispecific antibody for treatment of CEA-positive solid tumors," OncoImmunology 5(8):e1203498 (2016), 4 pages.
Barnes et al., "Methods for Growth of Cultured Cells in Serum-Free Medium," Anal Biochem., 102:255-270 (1980).
Barnes et al., "Serum-free Cell Culture: a Unifying Approach," Cell 22:649-655 (1980).
Blomer et al., "Highly Efficient and Sustained Gene Transfer in Adult Neurons with a Lentivirus Vector," Journal of Virology 71(9):6641-6649 (1997).
Boch et al., "TALEs of genome targeting," Nature Biotechnology 29(2):135-136 (2011).
Boerner et al., "Production Of Antigen-Specific Human Monoclonal Antibodies From In Vitro-Primed Human Splenocytes," J. Immunol., 147:86-95 (1991).
Bregni et al., "Human Peripheral Blood Hematopoietic Progenitors Are Optimal Targets of Retroviral-Mediated Gene Transfer," Blood 80:1418-1422 (1992).
Brennan et al., "Preparation of Bispecific Antibodies by Chemical Recombination of Monoclonal Immunoglobulin G1 Fragments," Science 229:81-83 (1985).
Brigham et al., "Rapid Communication: In vivo Transfection of Murine Lungs with a Functioning Prokaryotic Gene Using a Liposome Vehicle," Am. J. Med. Sci. 298:278-281 (1989).
Brodeur et al., Monoclonal Antibody Production Techniques and Applications, pp. 51-63 (Marcel Dekker, Inc., New York, 1987).
Bruggemann et al., "Comparison of The Effector Functions of Human Immunoglobulins Using A Matched Set of chimeric Antibodies," J. Exp. Med. 166:1351-1361 (1987).
Carter et al., "Humanization of an anti-p185HER2 antibody for human cancer therapy," Proc. Natl Acad. Sci. USA, 89:4285-4289 (1992).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Chari et al., "Immunoconjugates Containing Novel Maytansinoids: Promising Anticancer Drugs," Cancer Res. 52: 127-131 (1992).
Cheng et al., "A Rapid High-Sensitivity Reversed-Phase Ultra High Performance Liquid Chromatography Mass Spectrometry Method for Assessing Polysorbate 20 Degradation in Protein Therapeutics," J Pharm Sci, vol. 108:2880-2886 (2019).
Chiu et al., "Knockout of a difficult-to-remove CHO host cell protein, lipoprotein lipase, for improved polysorbate stability in monoclonal antibody formulations," Biotechnol Bioeng, 114(5):1006-1015 (2017).
Chothia et al., "Canonical Structures for the Hypervariable Regions of Immunoglobulins," J. Mol. Biol 196:901-917 (1987).
Chowdhury, "Engineering Hot Spots for Affinity Enhancement of Antibodies," Methods Mol. Biol. 207:179-196 (2008).
Clackson et al., "Making antibody fragments using phage display libraries," Nature 352:624-628 (1991).
Cleveland et al., "Routine Large-Scale Production of Monoclonal Antibodies in a Protein-Free Culture Medium," J. Immunol Methods 56:221-234 (1983).
Clynes et al., "Fe receptors are required in passive and active immunity to melanoma," Proc. Nat'l Acad. Sci. USA 95:652-656 (1998).
Cornetta et al., "Gene Transfer into Primates and Prospects for Gene Therapy in Humans," Nucleic Acid Research and Molecular Biology 36:311-322 (1987).
Corvari et al., "Mechanisms of Surfactant Degradation: Focus on Enzymatic Hydrolysis," WCBP CMC Strategy Forum 012720 (Jan. 27, 2020) 21 pgs.
Corvari, "Mechanisms of Hydrolytic Degradation of Surfactants, Focus on Enzymatic Hydrolysis," PharmSci360, 23 pgs. (Nov. 3, 2018).
Cragg et al., "Antibody specificity controls in vivo effector mechanisms of anti-CD20 reagents," Blood 103:2738-2743 (2004).

(56) References Cited

OTHER PUBLICATIONS

Cragg et al., "Complement-mediated lysis by anti-CD20 mAb correlates with segregation into lipid rafts," Blood 101:1045-1052 (2003).

Cunningham et al., "High-Resolution Epitope Mapping of hGH-Receptor Interactions by Alanine-Scanning Mutagenesis," Science 244:1081-1085 (1989).

Dall' Acqua et al., "Increasing the Affinity of a Human IgG1 for the Neonatal Fc Receptor: Biological Consequences," J. Immunol 169:5171-5180 (2002).

Dall'Acqua et al., "Antibody humanization by framework shuffling," Methods 36:43-60 (2005).

Dall'Acqua et al., "Properties of Human IgGis Engineered for Enhanced Binding to the Neonatal Fc Receptor (FcRn)," J. Biol. Chem. 281(33):23514-23524 (2006).

Danos et al., "Safe and efficient generation of recombinant retroviruses with amphotropic and ecotropic host ranges," Proc. Natl. Acad. Sci. USA 85:6460-6464 (1988).

DeWitt et al., "Genome editing via delivery of Cas9 ribonucleoprotein," Methods 121-122:9-15 (2017).

Dixit et al., "Residual Host Cell Protein Promotes Polysorbate 20 Degradation in a Sulfatase Drug Product Leading to Free Fatty Acid Particles," J Pharm Sci, 105:1657-1666 (2016).

Duncan et al., "The binding site for Clq on IgG," Nature 332:738-740 (1988).

Durai et al., "Zinc finger nucleases: custom-designed molecular scissors for genome engineering of plant and mammalian cells," Nucleic Acids Res. 33(18):5978-5990 (2005).

Eglitis et al., "Retroviral Vectors for Introduction of Genes into Mammalian Cells," BioTechniques 6:608-614 (1988).

Felgner et al., "Lipofection: A highly efficient, lipid-mediated DNA-transfection procedure," Proc. Natl. Acad. Sci. U.S.A. 84:7413-7417 (1987).

Ferrara et al., "Modulation of Therapeutic Antibody Effector Functions by Glycosylation Engineering: Influence of Golgi Enzyme Localization Domain and Co-Expression of Heterologous $\beta 1$, 4-N-acetylglucosaminyltransferase III and Golgi $\alpha$-mannosidase II," Biotechn Bioeng 93(5):851-861 (2006).

Firan et al., "The MHC class I-related receptor, FcRn, plays an essential role in the maternofetal transfer of $\gamma$-globulin in humans," Int. Immunol. 13(8):993-1002 (2001).

Friedman, "Progress Toward Human Gene Therapy," Science 244:1275-1281 (1989).

Gazzano-Santoro et al., "A non-radioactive complement-dependent cytotoxicity assay for anti-CD20 monoclonal antibody," J. Immunol. Methods 202:163-171 (1997).

Graham et al., "Characteristics of a Human Cell Line Transformed by DNA from Human Adenovirus Type 5," J. Gen Virol., 36:59-72 (1977).

Grevys et al., "Fc Engineering of Human IgGi for Altered Binding to the Neonatal Fc Receptor Affects Fc Effector Functions," J. Immunol. 194:5497-5508 (2015).

Gruber et al., "Efficient Tumor Cell Lysis Mediated by a Bispecific Single Chain Antibody Expressed in *Escherichia coli*," J. Immunol., 152:5368 (1994).

Guyer et al., "Immunoglobulin Binding By Mouse Intestinal Epithelial Cell Receptors," J. Immunol. 117(2):587-593 (1976).

Hall et al., "Polysorbates 20 and 80 Degradation by Group XV Lysosomal Phospholipase A2 Isomer X1 in Monoclonal Antibody Formulations," Journal Of Pharmaceutical Sciences, 105(5):1633-1642 (2016).

Ham et al., "Media and Growth Requirements," Meth. Enz., 58:44 (1979).

Hellstrom et al., "Antitumor effects of L6, anIgG2a antibody that reacts with most human carcinomas," Proc. Nat'l Acad. Sci. USA 83:7059-7063 (1986).

Hellstrom et al., "Strong antitumor activities of IgG3 antibodies to a human melanoma-associated ganglioside," Proc. Nat'l Acad. Sci. USA 82:1499-1502 (1985).

Holliger et al., "Diabodies: Small bivalent and bispecific antibody fragments," Proc. Natl. Acad. Sci. USA 90:6444-6448 (1993).

Holliger et al., "Engineered antibody fragments and the rise of single domains," Nature Biotechnology 23(9):1126-1136 (2005).

Holliger et al., "Specific killing of lymphoma cells by cytotoxic T-cells mediated by a bispecific diabody," Prot. Eng 9(3):299-305 (1996).

Hoogenboom et al. in Methods in Molecular Biology 178:1-37 (O'Brien et al., ed., Human Press, Totowa, NJ, (2001).

Huang et al., "A Novel Sample Preparation for Shotgun Proteomics Characterization of HCPs in Antibodies," Anal. Chem. 89(10):5436-5444 (2017).

Huang et al., "HCP Profiling and Lipase Monitoring for DNA Derived Biopharmaceuticals by LC/MS/MS," BEPBA Conference on Host Cell Protein, Dubrovnik, Croatia (May 14-16, 2018) 28 pgs.

Hudson et al., "Engineered antibodies," Nat. Med. 9:129-134 (2003).

Hughes et al., "Retroviral Gene Transfer to Primitive Normal and Leukemic Hematopoietic Cells Using Clinically Applicable Procedures," J. Clin. Invest. 89:1817-1824 (1992).

Idusogie et al., "Mapping of the C1q Binding Site on Rituxan, a Chimeric Antibody with a Human IgG1 Fc," J. Immunol. 164:4178-4184 (2000).

Johnson et al., "Effector Cell Recruitment with Novel Fv-based Dual-affinity Re-targeting Protein Leads to Potent Tumor Cytolysis and in Vivo B-cell Depletion," J. Mol. Biol. 399:436-449 (2010).

Johnson, "Gene Therapy for Cystic Fibrosis," Chest 107:77S-83S (1995).

Kabat et al., Sequences of Proteins of Immunological Interest, 5th Ed. Public Health Service, National Institutes of Health, Bethesda, MD (1991).

Kanda et al., "Comparison of Cell Lines for Stable Production of Fucose-Negative Antibodies With Enhanced ADCC," Biotechnol. Bioeng., 94(4):680-688 (2006).

Kashmiri et al., "SDR grafting—a new approach to antibody humanization," Methods 36:25-34 (2005).

Kido et al., "Use of a retroviral vector with an internal opsin promoter to direct gene expression to retinal photoreceptor cells," Current Eye Research 15:833-844 (1996).

Kim et al., "Identifying amino acid residues that influence plasma clearance of murine IgG1 fragments by site-directed mutagenesis," Eur. J. Immunol. 24:542-548 (1994).

Kim et al., "Localization of the site of the murine IgG1 molecule that is involved in binding to the murine intestinal Fc receptor," Eur. J. Immunol. 24:2429-2434 (1994).

Kim et al., "Mapping the site on human IgG for binding of the MHC class I-related receptor, FcRn," Eur. J. Immunol. 29:2819-2825 (1999).

Kindt et al. Kuby Immunology, 6th ed., W.H. Freeman and Co., p. 91 (2007).

Kipriyanov et al., "Bispecific Tandem Diabody for Tumor Therapy with Improved Antigen Binding and Pharmacokinetics," J Mol. Biol. 293:41-56 (1999).

Klein at al., "The use of CrossMAb technology for the generation of bi- and multispecific antibodies," MABS 8(6):1010-1020 (2016).

Klimka et al., "Human anti-CD30 recombinant antibodies by guided phage antibody selection using cell panning," Br. J. Cancer, 83:252-260 (2000).

Kostelny et al., "Formation of A Bispecific Antibody By The Use of Leucine Zippers," J. Immunol., 148(5):1547-1553 (1992).

Kozbor et al., "A Human Hybrid Myeloma for Production Of Human Monoclonal Antibodies," J. Immunol, 133(6):3001-3005 (1984).

Lee et al., "Targeted chromosomal deletions in human cells using zinc finger nucleases," Genome Res. 20(1):81-89 (2010).

LeGal La Salle et al., "An Adenovirus Vector for Gene Transfer into Neurons and Glia in the Brain," Science 259:988-990 (1993).

Li et al., "Human antibodies for immunotherapy development generated via a human B cell hybridoma technology," Proc. Natl. Acad. Sci. USA, 103(10):3557-3562 (2006).

Li et al., "piggyBac transposase tools for genome engineering," PNAS 110(25):E2279-E2287 (2013).

Lonberg, "Fully human antibodies from transgenic mouse and phage display platforms," Curr. Opin. Immunol. 20:450-459 (2008).

(56) References Cited

OTHER PUBLICATIONS

Lonberg, "Human antibodies from transgenic animals," Nat. Biotech. 23(9):1117-1125 (2005).
MacCallum et al., Antibody-antigen Interactions: Contact Analysis and Binding Site Topography J. Mol. Biol. 262:732-745 (1996).
Mather et al., "Culture of Testicular Cells in Hormone-Supplemented Serum-Free Medium," Annals N.Y. Acad. Sci., 383:44-68 (1982).
Mather, "Establishment and Characterization of Two Distinct Mouse Testicular Epithelial Cell Lines," Biol. Reprod., 23:243-252 (1980).
Medesan et al., "Localization of the site of the IgG molecule that regulates maternofetal transmission,in mice," Eur. J. Immunol. 26:2533-2536 (1996).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Improved Retroviral Vectors for Gene Transfer and Expression," Biotechnology 7:980-990 (1989).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).
Milstein et al., "Hybrid hybridomas and their use in immunohistochemistry," Nature 305:537-540 (1983).
Miyoshi et al., "Stable and efficient gene transfer into the retina using an HIV-based lentiviral vector," Proc. Natl. Acad. Sci. U.S.A. 94:10319-10323 (1997).
Moen, "Directions in Gene Therapy," Blood Cells 17:407-416 (1991).
Morrison et al., "Chimeric human antibody molecules: Mouse antigen-binding domains with human constant region domains," Proc. Natl. Acad. Sci. USA, 81:6851-6855 (1984).
Nagorsen et al., "Immunomodulatory therapy of cancer with T cell-engaging BiTE antibody blinatumomab," Exp Cell Res 317:1255-1260 (2011).
Naldini et al., "In Vivo Gene Delivery and Stable Transduction of Nondividing Cells by a Lentiviral Vector," Science 272:263-267 (1996).
Ni, "Research progress and future perspectives in antibodomics and antibodomic drugs," Xiandai Mianyixue, 26(4):265-268 (2006).
O'Gorman et al., "Protamine-Cre recombinase transgenes efficiently recombine target sequences in the male germ line of mice, but not in embryonic stem cells," Proc Natl Acad Sci USA 94:14602-14607 (1997).
Ono et al., "Plasmid DNAs directly injected into mouse brain with lipofectin can be incorporated and expressed by brain cells," Neuroscience Letters 117:259-263 (1990).
Osbourn et al., "From rodent reagents to human therapeutics using antibody guided selection," Methods 36:61-68 (2005).
Padlan, "A Possible Procedure for Reducing the Immunogenicity of Antibody Variable Domains While Preserving Their Ligand-Binding Properties," Mol. Immunol. 28:489-498 (1991).
Partial Search Report dated Aug. 19, 2021 in International Application No. PCT/US2021/024295.
Petkova et al., "Enhanced half-life of genetically engineered human IgG1 antibodies in a humanized FcRn mouse model: potential application in humorally mediated autoimmune disease," Int'l. Immunol. 18(12):1759-1769 (2006).
Pluckthun, in The Pharmacology of Monoclonal Antibodies, vol. 113, Rosenburg and Moore eds., (Springer-Verlag, New York), pp. 269-315 (1994).
Polakis, "Antibody Drug Conjugates for Cancer Therapy," Pharmacol Review 68:3-19 (2016).
Portolano et al., "Lack of Promiscuity in Autoantigen-Specific H and L Chain Combinations as Revealed by Human H and L Chain "Roulette"" J. Immunol. 150:880-887 (1993).
Presta et al., "Humanization of an Antibody Directed Against IgE," J. Immunol., 151:2623-2632 (1993).
Queen et al., "A humanized antibody that binds to the interleukin 2 receptor," Proc. Nat'l Acad. Sci. USA 86:10029-10033 (1989).
Ravetch et al., "Fe Receptors," Annu. Rev. Immunol. 9:457-492 (1991).
Riechmann et al., "Reshaping human antibodies for therapy," Nature 332:323-329 (1988).
Ripka et al., "Two Chinese Hamster Ovary Glycosylation Mutants Affected in the Conversion of GDP-Mannose to GDP-Fucose," Arch. Biochem. Biophys. 249:533-545 (1986).
Rosenberg et al., "Gene Transfer into Humans—Immunotherapy of Patients With Advanced Melanoma, Using Tumor-Infiltrating Lymphocytes Modified By Retroviral Gene Transduction," N. Engl. J. Med 323:570-578 (1990).
Rosok et al., "A Combinatorial Library Strategy for the Rapid Humanization of Anticarcinoma BR96 Fab," J. Biol. Chem. 271:22611-22618 (1996).
Schaefer et al., "Immunoglobulin domain crossover as a generic approach for the production of bispecific IgG antibodies," PNAS, 108(27):11187-11192 (2011).
Seimetz et al., "Development and approval of the trifunctional antibody catumaxomab (anti-EpCAM x anti-CD3) as a targeted cancer immunotherapy," Cancer Treat. Rev. 36:458-467 (2010).
Sharp, "Gene Therapy," The Lancet 337:1277-1278 (1991).
Shields et al., "High Resolution Mapping of the Binding Site on Human IgG1 for FcγRI, FcγRII, FcγRIII, and FcRn and Design of IgG1 Variants with Improved Binding to the FcγR," Biol. Chem. 276(9):6591-6604 (2001).
Sims et al., "A Humanized CD18 Antibody Can Block Function without Cell Destruction," J. Immunol. 151:2296-2308 (1993).
Spiess et al., "Alternative molecular formats and therapeutic applications for bispecific antibodies," Mol. Immunol. 67:95-106 (2015).
Stadler et al., "Elimination of large tumors in mice by mRNA-encoded bispecific antibodies," Nature Medicine (2017) 6 pgs.
Straubinger et al., "Liposomes as Carriers for Intracellular Delivery of Nucleic Acids," Methods in Enzymology 101:512-527 (1983).
Tolstoshev et al., "Gene expression using retroviral vectors," Current Opinion in Biotechnology 1:55-61 (1990).
Trubitsyna et al., "Use of mariner transposases for one-step delivery and integration of DNA in prokaryotes and eukaryotes by transfection," Nucleic Acids Res 45(10):e89, 10 pages (2017).
Tutt et al., "Trispecific F(ab')3 Derivatives That Use Cooperative Signaling Via The TCR/CD3 Complex and CD2 To Activate and Redirect Resting Cytotoxic T Cells," J. Immunol. 147:60-69 (1991).
Umana et al., "Engineered glycoforms of an antineuro-blastoma IgG1 with optimized antibody-dependent cellular cytotoxic activity," Nat Biotechnol 17:176-180 (1999).
Urlaub et al., "Isolation of Chinese hamster cell mutants deficient in dihydrofolate reductase activity," Proc. Natl. Acad. Sci. USA, 77(7):4216-4220 (1980).
Van Dijk et al., "Human antibodies as next generation therapeutics," Curr. Opin. Chem Biol. 5:368-374 (2001).
Vitetta et al., "Redesigning Nature's Poisons to Create Anti-Tumor Reagents," Science 238:1098-1104 (1987).
Vollmers et al., "Death by Stress: Natural IgM-Induced Apoptosis," Methods and Findings in Experimental and Clinical Pharmacology, 27(3):185-191 (2005).
Vollmers et al., "The "early birds": natural IgM antibodies and immune surveillance," Histology and Histopathology, 20:927-937 (2005).
Wolff et al., "Direct Gene Transfer into Mouse Muscle in Vivo," Science 247:1465-1468 (1990).
Wright et al., "Effect of glycosylation on antibody function: implications for genetic engineering," TIBTECH 15:26-32 (1997).
Wu et al., "Receptor-mediated Gene Delivery and Expression in Vivo," Journal of Biological Chemistry 263:14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xu et al., "Correction of the enzyme deficiency in hematopoietic cells of Gaucher patients using a clinically acceptable retroviral supernatant transduction protocol," Exp. Hemat. 22:223-230 (1994).
Yamane-Ohnuki et al., "Establishment of FUT8 Knockout Chinese Hamster Ovary Cells: An Ideal Host Cell Line for Producing

(56) References Cited

OTHER PUBLICATIONS

Completely Defucosylated Antibodies With Enhanced Antibody-Dependent Cellular Cytotoxicity," Biotech. Bioeng. 87:614-622 (2004).

Yeung et al., "Engineering Human IgG1 Affinity to Human Neonatal Fc Receptor: Impact of Affinity Improvement on Pharmacokinetics in Primates," J. Immunol. 182:7663-7671 (2009).

* cited by examiner

FIGURE 1

| Enzymes | Protein Name | Gene Symbol | Found in which product | |
|---|---|---|---|---|
| | Lipoprotein lipase | Lpl | X | X |
| | Phospholipase B-domain containing 2 | Plbd2 | X | |
| | Lipase A | Lipa | X | X |
| | Phospholipase A-2-activating protein | Plaa | X | |
| | Phospholipase D family member 3 | Pld3 | X | |
| Lipases | Phospholipase A2 group XV | Pla2g15 | X | |
| | Phospholipase C beta 1 | Plcb1 | | X |
| | Phospholipase C delta 1 | Plcd1 | | X |
| | DDHD domain containing protein 1 | Ddhd1 | | X |
| | Lysophospholipase-like protein 1 | Lyplal1 | | X |
| | Phospholipase A2 group XIIA | Pla2g12a | X | |
| | Peroxiredoxin 6 | Prdx6 | | X |
| | Lysophospholipase 1 | Lypla1 | X | |
| | Phospholipase A1 member A | Pla1a | X | |
| | Sphingomyelin phosphodiesterase 1 | Smpd1 | X | X |
| | Palmitoyl-protein thioesterase 1 | Ppt1 | X | X |
| | Isoamyl acetate hydrolyzing esterase 1 (putative) | Iah1 | X | X |
| Esterases | OTU deubiquitinase, ubiquitin aldehyde binding 1 | Otub1 | X | X |
| | Lysophospholipase 2 (Acyl-protein thioesterase 2) | Lypla2 | X | X |
| | Acyl-coA thioesterase 13 | Acot13 | | X |
| | Fatty acid synthase | Fasn | | X |
| | Carboxylesterase 1f/Liver carboxylesterase B-1-like | Ces1f/Ces-b1l | X | |
| | Carboxylesterase 1 | Ces1 | X | |
| | Sialic acid acetylesterase | Siae | X | |
| | Phospholipase A2 group VII | Pla2g7 | | X |
| Hydrolases | Ubiquitin specific peptidase 5 | Usp5 | | X |
| | N-acylsphingosine amidohydrolase 1 (Acid ceramidase) | Asah1 | | X |
| | Acylcarnitine hydrolase | Hach | X | |

FIGURE 3

| Blank KO host | Genes Knocked Out |
|---|---|
| Parental Blank Host | None |
| 1X KO | Plbd2 |
| 3X KO | Pla2g15, Lpl, Lipa |
| 7X KO | Pla2g15, Lpl, Lipa, Ppt1, Pld3, Plbd2, Smpd1 |
| 12X KO | Pla2g15, Lpl, Lipa, Ppt1, Pld3, Plbd2, Smpd1, Plaa, Iah1, Otub1, Lypla2, Pla2g12a |
| 8X KO | Bax, Bak, Pla2g15, Lpl, Lipa, Ppt1, Pld3, Smpd1 |
| 13X KO | Bax, Bak, Pla2g15, Lpl, Lipa, Ppt1, Plbd2, Pld3, Smpd1, Clu, Prdx1, Plaa, Acot13 |

FIGURE 15

| Product | Genes Knocked Out (KO) in CHO Parental Blank Host Cells | Decrease by PS20 Degradation Assay (Relative to Control Cells without KO) |
|---|---|---|
| mAb W | 7X (Pla2g15, Lpl, Lipa, Ppt1, Pld3, Plbd2, Smpd1) | 24% |
| mAb X | 7X (Pla2g15, Lpl, Lipa, Ppt1, Pld3, Plbd2, Smpd1) | 16% |
| mAb Y | 12X (Pla2g15, Lpl, Lipa, Ppt1, Pld3, Plbd2, Smpd1, Plaa, Iah1, Otub1, Lypla2, Pla2g12a) | 54% |
| mAb Z | 12X (Pla2g15, Lpl, Lipa, Ppt1, Pld3, Plbd2, Smpd1, Plaa, Iah1, Otub1, Lypla2, Pla2g12a) | 30% |

Figure 16

| Product | Genes Knocked Out (KO) in Parental mAb T Cells | Decrease by PS20 Degradation Assay (Relative to Control Cells without KO) |
|---|---|---|
| mAb T | 1X (*Pla2g15*) | 38% |
| | 2X (*Pla2g15, Lpl*) | 52% |
| | 3X (*Pla2g15, Lpl, Lipa*) | 70% |
| | 6X (*Pla2g15, Lpl, Lipa, Ppt1, Pld3, Plbd2*) | 94% |

```
                          SEQUENCE LISTING

<160> NUMBER OF SEQ ID NOS: 36

<210> SEQ ID NO 1
   <211> LENGTH: 6
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 1

Ser Ser Tyr Tyr Met Ala
   1               5

<210> SEQ ID NO 2
   <211> LENGTH: 5
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 2

Asp Ser Tyr Met Ser
   1               5

<210> SEQ ID NO 3
   <211> LENGTH: 17
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 3

Asp Met Tyr Pro Asp Asn Gly Asp Ser Ser Tyr Asn Gln Lys Phe Arg
   1               5                   10                  15

Glu

<210> SEQ ID NO 4
   <211> LENGTH: 8
   <212> TYPE: PRT
   <213> ORGANISM: Artificial Sequence
   <220> FEATURE:
   <223> OTHER INFORMATION: Description of Artificial Sequence: Synthetic
         peptide
```

```
<400> SEQUENCE: 4

Ala Pro Arg Trp Tyr Phe Ser Val
1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Asp Ile Ser Asn Tyr Leu Asn
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Thr Ser Arg Leu Arg Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Gly His Thr Leu Pro Pro Thr
1               5

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110
```

```
Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Tyr Leu Ile Glu
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ile Asn Pro Gly Ser Gly Asp Thr Tyr Tyr Ser Glu Lys Phe Lys
1               5                   10                  15

Gly

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Leu Asp Tyr
1               5
```

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ala Ser Gln Asp Ile Ser Ser Tyr Ile Val
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Gly Thr Asn Leu Glu Asp
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val His Tyr Ala Gln Phe Pro Tyr Thr
1               5

<210> SEQ ID NO 16
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 17

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 18
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210             215

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 20
<211> LENGTH: 694
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

```
Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Gly Gly Gly Gly Ser Gly Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
                260                 265                 270

Arg Gln Ala Pro Gly Lys Gly Leu Glu Trp Val Ser Arg Ile Arg Ser
            275                 280                 285

Lys Tyr Asn Asn Tyr Ala Thr Tyr Tyr Ala Asp Ser Val Lys Gly Arg
            290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
                340                 345                 350

Gly Thr Leu Val Thr Val Ser Ser Ala Ser Val Ala Ala Pro Ser Val
            355                 360                 365

Phe Ile Phe Pro Pro Ser Asp Glu Gln Leu Lys Ser Gly Thr Ala Ser
            370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
            435                 440                 445

Val Thr His Gln Gly Leu Ser Ser Pro Val Thr Lys Ser Phe Asn Arg
            450                 455                 460

Gly Glu Cys Asp Lys Thr His Thr Cys Pro Pro Cys Pro Ala Pro Glu
465                 470                 475                 480
```

```
Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
        595                 600                 605

Gln Val Ser Leu Trp Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly Lys
    690

<210> SEQ ID NO 21
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
            325                 330                 335

Glu Lys Thr Ile Ser Lys Ala Lys Gly Gln Pro Arg Glu Pro Gln Val
        340                 345                 350

Cys Thr Leu Pro Pro Ser Arg Asp Glu Leu Thr Lys Asn Gln Val Ser
    355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 22
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
```

```
            35                  40                  45
Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
            245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Gly Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
            435                 440                 445

Leu Ser Pro Gly Lys
            450
```

-continued

<210> SEQ ID NO 23
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro 355                 360                 365
Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460

<210> SEQ ID NO 24
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 213
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 25

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Ile Phe Thr Gly Ser Gly Ala Glu Tyr Lys Ala Glu Trp Ala Lys
1               5                   10                  15

Gly

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ala Gly Tyr Asp Tyr Pro Thr His Ala Met His Tyr
1               5                   10

<210> SEQ ID NO 28
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ala Ser Gln Gly Ile Ser Ser Ser Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Ser Glu Thr Glu Ser
1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Asn Thr Lys Val Gly Ser Ser Tyr Gly Asn Thr
1               5                   10

<210> SEQ ID NO 31
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser
        115                 120

<210> SEQ ID NO 32
<211> LENGTH: 110
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Gly Ala Ser Glu Thr Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys
            100                 105                 110

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ataacttcgt ataaagtctc ctatacgaag ttat                              34

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ataacttcgt atagaaaggt atatacgaag ttat                              34

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ataacttcgt atagcataca ttatacgaag ttat                              34

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 36

His His His His His His
1               5
```

MODIFIED MAMMALIAN CELLS

CROSS REFERENCE TO RELATED APPLICATIONS

This application claims the benefit of U.S. Provisional Application No. 63/000,464, filed Mar. 26, 2020, U.S. Provisional Application No. 63/128,419, filed Dec. 21, 2020, and U.S. Provisional Application No. 63/155,225, filed Mar. 1, 2021, the disclosures of each of which are incorporated herein by reference in its entirety.

SEQUENCE LISTINGS

The instant application contains a Sequence Listing which has been submitted electronically in ASCII format and is hereby incorporated by reference in its entirety. Said ASCII copy, created on Jun. 1, 2021, is named 00B206_1035_SL.txt and is 38,185 bytes in size. The Sequence Listing does not extend beyond the scope of the specification and thus does not contain new matter.

1. FIELD OF INVENTION

The present disclosure relates to modified mammalian cells, (e.g., Chinese Hamster Ovary (CHO) cells) that have reduced or eliminated activity of certain host cell proteins, e.g., host cell enzymes, including but not limited to, certain lipases, esterases, and/or hydrolases, methods for making such cells, and methods of using such cells in the production of a product of interest, e.g., a recombinant protein.

2. BACKGROUND

Mammalian cells, e.g., CHO cells, express many proteins that are not essential for cell growth, survival, and/or productivity. Expression of these host cell proteins, however, consumes considerable cellular energy and DNA/protein building blocks. Reducing or eliminating the expression of such proteins can render cell growth more efficient. Moreover, in contexts where the cell is used for production of a product of interest, e.g., a recombinant protein, some of these proteins can co-purify with the product of interest, leading to increased costs associated with additional purification processes and/or decreased shelf-life of the resulting product. For example, certain residual host cell proteins that co-purify with the product of interest can degrade polysorbate used as a surfactant in the final drug product, and lead to particle formation (Dixit et al., J Pharm Sci, 2016, Volume 105, Issue 5, Pages 1657-1666). Accordingly, there is a need in the art for methods, cells, and compositions for producing a product of interest, e.g., a recombinant protein, where the cells expressing the product of interest have reduced or eliminated activity, e.g., expression, of certain host cell proteins, e.g., enzymes, including but not limited to, certain lipases, esterases, and/or hydrolases, that are not essential for cell growth, survival, and/or productivity. For example, investigations to reduce hydrolytic activity from residual CHO host cell proteins that co-purify with mAbs and subsequently degrade polysorbate in the drug product led to the identification of lipoprotein lipase (LPL): CHO cell lines with LPL knocked out resulted in cell culture harvests with 41-57% less polysorbate degradation than their wild-type counterpart (Chiu et al., Biotechnol Bioeng, 2017, Volume 114, Issue 5, Pages 1006-1015). By reducing or eliminating the expression of such enzymes, the negative impact of the associated enzymatic activity (e.g., hydrolytic degradation of polysorbate in the drug product by residual hydrolases) may be mitigated. However, that investigation did not determine if the benefits observed for the LPL knock out at the cell culture harvest stage was maintained through downstream processing. It is important to test purified materials generated from knock out cell lines to demonstrate the benefits are achieved after purification and thus translate into benefits in the drug product.

3. SUMMARY

The present disclosure relates to modified mammalian cells, (e.g., Chinese Hamster Ovary (CHO) cells) that have reduced or eliminated activity of certain host cell proteins, e.g., host cell enzymes, including but not limited to, certain lipases, esterases, and/or hydrolases, methods for making such cells, and methods of using such cells in the production of a product of interest, e.g., a recombinant protein.

In certain embodiments, the present disclosure provides a recombinant host cell where the cell is modified to reduce or eliminate the activity of one or more enzyme relative to the activity of the enzyme in an unmodified cell. In certain embodiments, the one or more enzyme is selected from the group consisting of: Lipoprotein lipase (LPL); phospholipase B-domain containing 2 (PLBL2/PLBD2); Lipase A (Lysosomal acid lipase/cholesteryl ester hydrolase, Lipase) (LIPA); Phospholipase A-2-activating protein (PLAA); Phospholipase D3 (PLD3); Phospholipase A2 group XV (LPLA2); Phospholipase C beta 1 (PLCB1); Phospholipase C delta 1 (PLCD1); DDHD domain containing protein 1 (Fragment) (DDHD1); Lysophospholipase-like protein 1 (LYPLA1); Phospholipase A2 group XIIA (PLA2G12A); Peroxiredoxin 6 (PRDX6); Sphingomyelin phosphodiesterase (SMPD1); Palmitoyl-protein thioesterase 1 (PPT1); Isoamyl acetate hydrolyzing esterase 1 (putative) (IAH1); OTU deubiquitinase, ubiquitin aldehyde binding 1 (OTUB1); Lysophospholipase 2 (Acyl-protein thioesterase 2) (LYPLA2); Acyl-coenzyme A thioesterase 13 (ACOT13); Fatty acid synthase (FASN); Phospholipase A2 group VII (PLA2G7); Ubiquitin specific peptidase 5 (USP5); N-acyl-sphingosine amidohydrolase 1 (Acid ceramidase) (ASAH1); Lipase maturation factor 1 (LMF1); Apolipoprotein-CII (APOC2); Acylcarnitine hydrolase (HACH); Carboxylesterase 1F (CES1F) or Liver carboxylesterase B-1-like (CES-B1L); Lysophospholipase 1 (LYPLA1); Carboxylesterase 1 (CES1); Phospholipase A1 member A (PLA1A); and Sialic acid acetylesterase (SIAE).

In certain embodiments, the activity of: a) PPT1; b) LPLA2; LPL; and LIPA; c) LPLA2; LPL; LIPA; PPT1; PLBL2; PLD3; and SMPD1; d) LPLA2; LPL; LIPA; PPT1; PLBL2; PLD3; SMPD1; PLAA; IAH1; OTUB1; LYPLA2; and PLA2G12A; e) BAX; BAK; LPLA2; LPL; LIPA; PPT1; PLD3; and SMPD1; f) BAX; BAK; LPLA2; LPL; LIPA; PPT1; PLBL2; PLD3; SMPD1; CLU; PRDX1; PLAA; and ACOT13; g) LPLA2; LPL; and PPT1; h) LPLA2; LPL; LIPA; and PPT1; i) HACH; CES1F/CES-B1L; and LYPLA1; j) LPLA2; LPL; LIPA; PPT1; HACH; CES1F/CES-B1L; and LYPLA1; k) SMPD1; CES1; PLA1A; and SIAE; l) LPLA2; LPL; LIPA; PPT1; HACH; CES1F/CES-B1L; LYPLA1; SMPD1; CES1; PLA1A; and SIAE; m) LPLA2; LMF1; LIPA; PPT1; HACH; CES1F/CES-B1L; and LYPLA1; n) LPLA2; LMF1; APOC2; LIPA; PPT1; HACH; CES1F/CES-B1L; and LYPLA1; o) LMF1 and APOC2 in a recombinant host cell is reduced or eliminated.

In certain embodiments, the activity of the one or more enzyme in a recombinant host cell is reduced or eliminated by: (a) knocking down expression of the enzyme; (b) or knocking out expression of the enzyme; or (c) altering the nucleic acid sequence encoding the enzyme.

In certain embodiments, the present disclosure is directed to a recombinant host cell comprising one or more altered enzyme genes. In certain embodiments, the one or more altered enzyme genes have no detectable enzymatic activity. In certain embodiments, the recombinant host cell comprises a nucleic acid sequence encoding a product of interest. In certain embodiments, the nucleic acid sequence is integrated in the cellular genome of the mammalian cell at a targeted location. In certain embodiments, the recombinant host cell further comprises a nucleic acid encoding the product of interest that is randomly integrated in the cellular genome of the mammalian cell. In certain embodiments, the modified cell does not express any detectable LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides compositions comprising a recombinant host cell described in the present disclosure.

In certain embodiments, the present disclosure provides a method for reducing enzymatic activity in a cell, where the method comprises knocking down or knocking out the expression of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing enzymatic activity in a cell, where the method comprises modulating a cell culture process and/or media composition, wherein modulating a cell culture process and/or media composition results in reduced activity of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing enzymatic activity in a cell, wherein the method comprises selecting cells with reduced activity of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing enzymatic activity in a cell, wherein the method comprises altering the gene encoding one or more of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing or eliminating enzymatic activity in a cell, wherein the method comprises administering to the cell a genetic engineering system, wherein the genetic engineering system knocks down or knocks out the expression of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing or eliminating enzymatic activity in a cell, wherein the method comprises administering to the cell a genetic engineering system, wherein the genetic engineering system alters the nucleic acid sequence encoding one or more of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE so that the one or more of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; SIAE have reduced or eliminated enzymatic activity.

In certain embodiments, the present disclosure provides a method of producing a product of interest comprising culturing mammalian cells expressing the product of interest, wherein the mammalian cells express the product of interest and have reduced or eliminated activity of one or more of the following LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method of culturing a population of mammalian cells expressing a product of interest, wherein the mammalian cells have reduced or eliminated activity of one or more of the following LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a recombinant host cell comprising one or more altered enzyme genes. In certain embodiments, the one or more altered enzyme genes are altered by disruption of a coding region. In certain embodiments, the one or more enzyme genes alteration comprises a biallelic alteration. In certain embodiments, the one or more enzyme genes alteration comprises a deletion of 1 or more base pairs, 2 or more base pairs, 3 or more base pairs, 4 or more base pairs, 5 or more base pairs, 6 or more base pairs, 7 or more base pairs, 8 or more base pairs, 9 or more base pairs, 10 or more base pairs, 11 or more base pairs, 12 or more base pairs, 13 or more base pairs, 14 or more base pairs, 15 or more base pairs, 16 or more base pairs, 17 or more base pairs, 18 or more base pairs, 19 or more base pairs, or 20 or more base pairs. In certain embodiments, the one or more enzyme genes are LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain of the above described embodiments, the genetic engineering system is selected from the group consisting of a CRISPR/Cas system, a zinc-finger nuclease (ZFN) system, a transcription activator-like effector nuclease (TALEN) system and a combination thereof. In certain of the above described embodiments, the genetic engineering system is a CRISPR/Cas9 system.

In certain of the above described embodiments, the CRISPR/Cas9 system comprises: (a) a Cas9 molecule, and (b) one or more guide RNAs (gRNAs) comprising a targeting sequence that is complementary to a target sequence in a gene encoding LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain of the above described embodiments, the genetic engineering system comprises an RNA selected from the group consisting of: a short hairpin RNA (shRNA), a small interference RNA (siRNA), and a microRNA (miRNA), wherein the RNA is complementary to a portion of an mRNA expressed by one or more of the LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE genes. In certain of the above described embodiments, the genetic engineering system is a zinc-finger nuclease (ZFN) system or a transcription activator-like effector nuclease (TALEN) system.

In certain of the above described embodiments, the reduction or elimination of activity is of: a) PPT1; b) LPLA2; LPL; and LIPA; c) LPLA2; LPL; LIPA; PPT1; PLBL2; PLD3; and SMPD1; d) LPLA2; LPL; LIPA; PPT1; PLBL2; PLD3; SMPD1; PLAA; IAH1; OTUB1; LYPLA2; and PLA2G12A; e) BAX; BAK; LPLA2; LPL; LIPA; PPT1; PLD3; and SMPD1; f) BAX; BAK; LPLA2; LPL; LIPA; PPT1; PLBL2; PLD3; SMPD1; CLU; PRDX1; PLAA; and ACOT13 or g) LPLA2; LPL; and PPT1; h) LPLA2; LPL; LIPA; and PPT1; i) HACH; CES1F/CES-B1L; and LYPLA1; j) LPLA2; LPL; LIPA; PPT1; HACH; CES1F/CES-B1L; and LYPLA1; k) SMPD1; CES1; PLA1A; and SIAE; l) LPLA2; LPL; LIPA; PPT1; HACH; CES1F/CES-B1L; LYPLA1; SMPD1; CES1; PLA1A; and SIAE; m) LPLA2; LMF1; LIPA; PPT1; HACH; CES1F/CES-B1L; and LYPLA1; n) LPLA2; LMF1; APOC2; LIPA; PPT1; HACH; CES1F/CES-B1L; and LYPLA1; o) LMF1 and APOC2 in the mammalian cells.

In certain of the above described embodiments, the methods provided in the present disclosure further comprise purifying the product of interest, harvesting the product of interest, and/or formulating the product of interest.

In certain of the above described embodiments, the degradation of a polyoxyethylene sorbitan monolaurate is reduced. In certain of the above described embodiments, the degradation of polysorbate 20 (PS20 or Tween 20) is reduced. In certain of the above described embodiments, the degradation of polysorbate 80 (PS80 or Tween 80) is reduced.

In certain of the above described embodiments, the cell is a mammalian cell. In certain of the above described embodiments, the mammalian cell is a CHO cell.

In certain of the above described embodiments, the cell expresses a product of interest. In certain of the above described embodiments, the product of interest expressed by the mammalian cells is encoded by a nucleic acid sequence. In certain of the above described embodiments, the nucleic acid sequence is integrated in the cellular genome of the mammalian cells at a targeted location. In certain of the above described embodiments, the product of interest expressed by the cells is further encoded by a nucleic acid sequence that is randomly integrated in the cellular genome of the mammalian cells.

In certain of the above described embodiments, the product of interest comprises a protein, a viral particle or a viral vector. In certain of the above described embodiments, the product of interest comprises a recombinant protein. In certain of the above described embodiments, the product of interest comprises an antibody or an antigen-binding fragment thereof. In certain of the above described embodiments, the antibody is a multispecific antibody or an antigen-binding fragment thereof. In certain of the above described embodiments, the antibody consists of a single heavy chain sequence and a single light chain sequence or antigen-binding fragments thereof. In certain of the above described embodiments, the antibody is a chimeric antibody, a human antibody or a humanized antibody. In certain of the above described embodiments, the antibody is a monoclonal antibody.

In certain embodiments, the modified cell of the present disclosure does not express any detectable PPT1. In certain embodiments, the modified cell of the present disclosure does not express any detectable LPLA2, LPL, and LIPA. In certain embodiments, the modified cell of the present disclosure does not express any detectable LPLA2, LPL, LIPA, PPT1, PLBL2, PLD3, and SMPD1. In certain embodiments, the modified cell of the present disclosure does not express any detectable LPLA2, LPL, LIPA, PPT1, PLBL2, PLD3, SMPD1, PLAA, IAH1, OTUB1, LYPLA2, and PLA2G12A. In certain embodiments, the modified cell of the present disclosure does not express any detectable BAX, BAK, LPLA2, LPL, LIPA, PPT1, PLD3, and SMPD1. In certain embodiments, the modified cell of the present disclosure does not express any detectable BAX, BAK, LPLA2, LPL, LIPA, PPT1, PLBL2, PLD3, SMPD1, CLU, PRDX1, PLAA, and ACOT13. In certain embodiments, the modified cell of the present disclosure does not express any detectable LPLA2, LPL, and PPT1. In certain embodiments, the modified cell of the present disclosure does not express any detectable LPLA2, LPL, LIPA and PPT1. In certain embodiments, the modified cell of the present disclosure does not express any detectable HACH, CES1F/CES-B1L, and LYPLA1. In certain embodiments, the modified cell of the present disclosure does not express any detectable LPLA2, LPL, LIPA, PPT1, HACH, CES1F/CES-B1L, and LYPLA1. In certain embodiments, the modified cell of the present disclosure does not express any detectable SMPD1, CES1, PLA1A, and SIAE. In certain embodiments, the modified cell of the present disclosure does not express any detectable LPLA2, LPL, LIPA, PPT1, HACH, CES1F/CES-B1L, LYPLA1, SMPD1, CES1, PLA1A, and SIAE. In certain embodiments, the modified cell of the present disclosure does not express any detectable LPLA2, LMF1, LIPA, PPT1, HACH, CES1F/CES-B1L, and LYPLA1. In certain embodiments, the modified cell of the present disclosure does not express any detectable LPLA2, LMF1, APOC2, LIPA, PPT1, HACH, CES1F/CES-B1L, and LYPLA1. In certain embodiments, the modified cell of the present disclosure does not express any detectable LMF1 and APOC2.

In certain embodiments, the present disclosure provides a recombinant host cell, wherein the cell is modified to reduce or eliminate the activity of PPT1 enzymes relative to the activity of the enzymes in an unmodified cell. In certain embodiments, the present disclosure provides a recombinant host cell, wherein the cell is modified to reduce or eliminate the activity of LPLA2, LPL, and LIPA enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, PLBL2, PLD3, and SMPD1 enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, PLBL2, PLD3, SMPD1, PLAA, IAH1, OTUB1, LYPLA2, and PLA2G12A enzymes relative to the activity of the enzymes in an unmodified cell. In certain embodiments, the present disclosure provides a recombinant host cell, wherein the cell is modified to reduce or eliminate the activity of BAX, BAK, LPLA2, LPL, LIPA, PPT1, PLD3, and SMPD1 enzymes relative to the activity of the enzymes in an unmodified cell. In certain embodiments, the present disclosure provides a recombinant host cell, wherein the cell is modified to reduce or eliminate the activity of BAX, BAK, LPLA2, LPL, LIPA, PPT1, PLBL2, PLD3, SMPD1, CLU, PRDX1, PLAA, and ACOT13 enzymes relative to the activity of the enzymes in an unmodified cell. In certain embodiments, the present disclosure provides a recombinant host cell, wherein the cell is modified to reduce or eliminate the activity of LPLA2, LPL, and PPT1 enzymes relative to the activity of the enzymes in an unmodified cell. In certain embodiments, the present disclosure provides a recombinant host cell, wherein the cell is modified to reduce or eliminate the activity of LPLA2, LPL, LIPA and PPT1 enzymes relative to the activity of the enzymes in an unmodified cell. In certain embodiments, the present disclosure provides recombinant host cell, wherein the cell is modified to reduce or eliminate the activity of HACH, CES1F/CES-B1L, and LYPLA1 enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, HACH, CES1F/CES-B1L, and LYPLA1 enzymes relative to the activity of the enzymes in an unmodified cell. In certain embodiments, the present disclosure provides a recombinant host cell, wherein the cell is modified to reduce or eliminate the activity of SMPD1, CES1, PLA1A, and SIAE enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, HACH, CES1F/CES-B1L, LYPLA1, SMPD1, CES1, PLA1A, and SIAE enzymes relative to the activity of the enzymes in an unmodified cell. In certain embodiments, the present disclosure provides a recombinant host cell, wherein the cell is modified to reduce or eliminate the activity of LPLA2, LMF1, LIPA, PPT1, HACH, CES1F/CES-B1L, and LYPLA1 enzymes relative to the activity of the enzymes in an unmodified cell. In certain embodiments, the present disclosure provides a recombinant host cell, wherein the cell is modified to reduce or eliminate the activity of LPLA2, LMF1, APOC2, LIPA, PPT1, HACH, CES1F/CES-B1L and LYPLA1 enzymes relative to the activity of the enzymes in an unmodified cell. In certain embodiments, the present disclosure provides a recombinant host cell, wherein the cell is modified to reduce or eliminate the activity of LMF1 and APOC2 relative to their activity in an unmodified cell.

In certain embodiments, the present disclosure provides a method for reducing enzymatic activity in a cell, comprising knocking down or knocking out the expression of PPT1. In certain embodiments, the present disclosure provides a method for reducing enzymatic activity in a cell, comprising knocking down or knocking out the expression of LPLA2, LPL, and LIPA. In certain embodiments, the present disclosure provides a method for reducing enzymatic activity in a cell, comprising knocking down or knocking out the expression of LPLA2, LPL, LIPA, PPT1, PLBL2, PLD3, and SMPD1. In certain embodiments, the present disclosure provides a method for reducing enzymatic activity in a cell, comprising knocking down or knocking out the expression of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising knocking down or knocking out the expression of BAX, BAK, LPLA2, LPL, LIPA, PPT1, PLD3, and SMPD1. In certain embodiments, the present disclosure provides a method for reducing enzymatic activity in a cell, comprising knocking down or knocking out the expression of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising knocking down or knocking out the expression of LPLA2, LPL, and PPT1. In certain embodiments, the present disclosure provides a method for reducing enzymatic activity in a cell, comprising knocking down or knocking out the expression of LPLA2, LPL, LIPA and PPT1. In certain embodiments, the present disclosure provides a method for reducing enzymatic activity in a cell, comprising knocking down or knocking out the expression of HACH, CES1F/CES-B1L, and LYPLA1. In certain embodiments, the present disclosure provides a method for reducing enzymatic activity in a cell, comprising knocking down or knocking out the expression of LPLA2, LPL, LIPA, PPT1, HACH, CES1F/CES-B1L, and LYPLA1. In certain embodiments, the present disclosure provides a method for reducing enzymatic activity in a cell, comprising knocking down or knocking out the expression of SMPD1, CES1, PLA1A, and SIAE. In certain embodiments, the present disclosure provides a method for reducing enzymatic activity in a cell, comprising knocking down or knocking out the expression of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising knocking down or knocking out the expression of LPLA2, LMF1, LIPA, PPT1, HACH, CES1F/CES-B1L, and LYPLA1. In certain embodiments, the present disclosure provides a method for reducing enzymatic activity in a cell, comprising knocking down or knocking out the expression of LPLA2, LMF1, APOC2, LIPA, PPT1, HACH, CES1F/CES-B1L, and LYPLA1. In certain embodiments, the present disclosure provides a method for reducing enzymatic activity in a cell, comprising knocking down or knocking out the expression of LMF1 and APOC2.

In certain embodiments, the present disclosure provides a method for reducing enzymatic activity in a cell, comprising modulating a cell culture process and/or media composition, wherein modulating a cell culture process and/or media composition results in reduced activity of PPT1. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, and LIPA. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, PLBL2, PLD3, and SMPD1. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising modulating a cell culture process and/or media composition, wherein modulating a cell culture process and/or media composition results in reduced activity of BAX, BAK, LPLA2, LPL, LIPA, PPT1, PLD3, and SMPD1. In certain embodiments, the present disclosure provides a method for reducing enzymatic activity in a cell, comprising modulating a cell culture process and/or media composition, wherein modulating a cell culture process and/or media composition results in reduced activity of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, and PPT1. In certain embodiments, the present disclosure provides a method for reducing enzymatic activity in a cell, comprising modulating a cell culture process and/or media composition, wherein modulating a cell culture process and/or media composition results in reduced activity of LPLA2; LPL; LIPA and PPT1. In certain embodiments, the present disclosure provides a method for reducing enzymatic activity in a cell, comprising modulating a cell culture process and/or media composition, wherein modulating a cell culture process and/or media composition results in reduced activity of HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of SMPD1, CES1, PLA1A, and SIAE. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising modulating a cell culture process and/or media composition, wherein modulating a cell culture process and/or media composition results in reduced activity of LPLA2, LMF1, LIPA, PPT1, HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of LPLA2, LMF1, APOC2, LIPA, PPT1, HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of LMF1 and APOC2.

In certain embodiments, the present disclosure provides a method for reducing enzymatic activity in a cell, comprising selecting cells with reduced activity of PPT1. In certain embodiments, the present disclosure provides a method for reducing enzymatic activity in a cell, comprising selecting cells with reduced activity of LPLA2, LPL, and LIPA. In certain embodiments, the present disclosure provides a method for reducing enzymatic activity in a cell, comprising selecting cells with reduced activity of LPLA2, LPL, LIPA, PPT1, PLBL2, PLD3, and SMPD1. In certain embodiments, the present disclosure provides a method for reducing enzymatic activity in a cell, comprising selecting cells with reduced activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising selecting cells with reduced activity of BAX, BAK, LPLA2, LPL, LIPA, PPT1, PLD3, and SMPD1. In certain embodiments, the present disclosure provides a method for reducing enzymatic activity in a cell, comprising selecting cells with reduced activity of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising selecting cells with reduced activity of LPLA2, LPL, and PPT1. In certain embodiments, the present disclosure provides a method for reducing enzymatic activity in a cell, comprising selecting cells with reduced activity of LPLA2, LPL, LIPA and PPT1. In certain embodiments, the present disclosure provides a method for reducing enzymatic activity in a cell, comprising selecting cells with reduced activity of HACH, CES1F/CES-B1L, and LYPLA1. In certain embodiments, the present disclosure provides a method for reducing enzymatic activity in a cell, comprising selecting cells with reduced activity of LPLA2, LPL, LIPA, PPT1, HACH, CES1F/CES-B1L, and LYPLA1. In certain embodiments, the present disclosure provides a method for reducing enzymatic activity in a cell, comprising selecting cells with reduced activity of SMPD1, CES1, PLA1A, and SIAE. In certain embodiments, the present disclosure provides a method for reducing enzymatic activity in a cell, comprising selecting cells with reduced activity of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising selecting cells with reduced activity of LPLA2, LMF1, LIPA, PPT1, HACH, CES1F/CES-B1L, and LYPLA1. In certain embodiments, the present disclosure provides a method for reducing enzymatic activity in a cell, comprising selecting cells with reduced activity of LPLA2, LMF1, APOC2, LIPA, PPT1, HACH, CES1F/CES-B1L, and LYPLA1. In certain embodiments, the present disclosure provides a method for reducing enzymatic activity in a cell, comprising selecting cells with reduced activity of LMF1 and APOC2.

In certain embodiments, the present disclosure provides a method for reducing enzymatic activity in a cell, comprising altering the gene encoding PPT1. In certain embodiments, the present disclosure provides a method for reducing enzymatic activity in a cell, comprising altering the gene encoding one or more of LPLA2, LPL, and LIPA. In certain embodiments, the present disclosure provides a method for reducing enzymatic activity in a cell, comprising altering the gene encoding one or more of LPLA2, LPL, LIPA, PPT1, PLBL2, PLD3, and SMPD1. In certain embodiments, the present disclosure provides a method for reducing enzymatic activity in a cell, comprising altering the gene encoding one or more of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising altering the gene encoding one or more of BAX, BAK, LPLA2, LPL, LIPA, PPT1, PLD3, and SMPD1. In certain embodiments, the present disclosure provides a method for reducing enzymatic activity in a cell, comprising altering the gene encoding one or more of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising altering the gene encoding one or more of LPLA2, LPL, and PPT1. In certain embodiments, the present disclosure provides a method for reducing enzymatic activity in a cell, comprising altering the gene encoding one or more of LPLA2, LPL, LIPA and PPT1. In certain embodiments, the present disclosure provides a method for reducing enzymatic activity in a cell, comprising altering the gene encoding one or more of HACH, CES1F/CES-B1L, and LYPLA1. In certain embodiments, the present disclosure provides a method for reducing enzymatic activity in a cell, comprising altering the gene encoding one or more of LPLA2, LPL, LIPA, PPT1, HACH, CES1F/CES-B1L, and LYPLA1. In certain embodiments, the present disclosure provides a method for reducing enzymatic activity in a cell, comprising altering the gene encoding one or more of SMPD1, CES1, PLA1A, and SIAE. In certain embodiments, the present disclosure provides a method for reducing enzymatic activity in a cell, comprising altering the gene encoding one or more of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising altering the gene encoding one or more of LPLA2, LMF1, LIPA, PPT1, HACH, CES1F/CES-B1L, and LYPLA1. In certain embodiments, the present disclosure provides a method for reducing enzymatic activity in a cell, comprising altering the gene encoding one or more of LPLA2, LMF1, APOC2, LIPA, PPT1, HACH, CES1F/CES-B1L, and LYPLA1. In certain embodiments, the present disclosure provides a method for reducing enzymatic activity in a cell, comprising altering the gene encoding one or more of LMF1 and APOC2.

In certain embodiments, the present disclosure provides a method for reducing or eliminating enzymatic activity in a cell, comprising administering to the cell a genetic engineering system, wherein the genetic engineering system knocks down or knocks out the expression of PPT1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, and LIPA. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, PLBL2, PLD3, and SMPD1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing or eliminating enzymatic activity in a cell, comprising administering to the cell a genetic engineering system, wherein the genetic engineering system knocks down or knocks out the expression of BAX, BAK, LPLA2, LPL, LIPA, PPT1, PLD3, and SMPD1. In certain embodiments, the present disclosure provides a method for reducing or eliminating enzymatic activity in a cell, comprising administering to the cell a genetic engineering system, wherein the genetic engineering system knocks down or knocks out the expression of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, and PPT1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA and PPT1. In certain embodiments, the present disclosure provides a method for reducing or eliminating enzymatic activity in a cell, comprising administering to the cell a genetic engineering system, wherein the genetic engineering system knocks down or knocks out the expression of HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of SMPD1, CES1, PLA1A, and SIAE. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, HACH, CES1F/CES-B1L, LYPLA1, SMPD1, CES1, PLA1A, and SIAE. In certain embodiments, the present disclosure provides a method for reducing or eliminating enzymatic activity in a cell, comprising administering to the cell a genetic engineering system, wherein the genetic engineering system knocks down or knocks out the expression of LPLA2, LMF1, LIPA, PPT1, HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LMF1, APOC2, LIPA, PPT1, HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of LMF1 and APOC2.

In certain embodiments, the present disclosure provides a method for reducing or eliminating enzymatic activity in a cell, comprising administering to the cell a genetic engineering system, wherein the genetic engineering system alters the nucleic acid sequence encoding PPT1 so that the PPT1 has reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, and LIPA so that the LPLA2, LPL, and LIPA have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, PLBL2, PLD3, and SMPD1 so that the LPLA2, LPL, LIPA, PPT1, PLBL2, PLD3, and SMPD1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, PLBL2, PLD3, SMPD1, PLAA, IAH1, OTUB1, LYPLA2, and PLA2G12A so that the LPLA2, LPL, LIPA, PPT1, PLBL2, PLD3, SMPD1, PLAA, IAH1, OTUB1, LYPLA2, and PLA2G12A have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding BAX, BAK, LPLA2, LPL, LIPA, PPT1, PLD3, and SMPD1 so that the BAX, BAK, LPLA2, LPL, LIPA, PPT1, PLD3, and SMPD1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding BAX, BAK, LPLA2, LPL, LIPA, PPT1, PLBL2, PLD3, SMPD1, CLU, PRDX1, PLAA, and ACOT13 so that the BAX, BAK, LPLA2, LPL, LIPA, PPT1, PLBL2, PLD3, SMPD1, CLU, PRDX1, PLAA, and ACOT13 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, and PPT1 so that the LPLA2, LPL, and PPT1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA and PPT1 so that the LPLA2, LPL, LIPA and PPT1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding HACH, CES1F/CES-B1L, and LYPLA1 so that the HACH, CES1F/CES-B1L, and LYPLA1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, HACH, CES1F/CES-B1L, and LYPLA1 so that the LPLA2, LPL, LIPA, PPT1, HACH, CES1F/CES-B1L, and LYPLA1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding SMPD1, CES1, PLA1A, and SIAE and PPT1 so that the SMPD1, CES1, PLA1A, and SIAE have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, HACH, CES1F/CES-B1L, LYPLA1, SMPD1, CES1, PLA1A, and SIAE so that the LPLA2, LPL, LIPA, PPT1, HACH, CES1F/CES-B1L, LYPLA1, SMPD1, CES1, PLA1A, and SIAE have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LMF1, LIPA, PPT1, HACH, CES1F/CES-B1L, and LYPLA1 so that the LPLA2, LMF1, LIPA, PPT1, HACH, CES1F/CES-B1L, and LYPLA1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LMF1, APOC2, LIPA, PPT1, HACH, CES1F/CES-B1L, and LYPLA1 so that the LPLA2, LMF1, APOC2, LIPA, PPT1, HACH, CES1F/CES-B1L, and LYPLA1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LMF1 and APOC2 so that the LMF1 and APOC2 have reduced or eliminated activity.

In certain embodiments, the present disclosure provides a method of producing a product of interest comprising culturing mammalian cells expressing the product of interest, wherein the mammalian cells express the product of interest and have reduced or eliminated activity of PPT1. In certain embodiments, the present disclosure provides a method of producing a product of interest comprising culturing mammalian cells expressing the product of interest, wherein the mammalian cells express the product of interest and have reduced or eliminated activity of LPLA2, LPL, and LIPA. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, PLBL2, PLD3, and SMPD1. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method of producing a product of interest comprising culturing mammalian cells expressing the product of interest, wherein the mammalian cells express the product of interest and have reduced or eliminated activity of BAX, BAK, LPLA2, LPL, LIPA, PPT1, PLD3, and SMPD1. In certain embodiments, the present disclosure provides a method of producing a product of interest comprising culturing mammalian cells expressing the product of interest, wherein the mammalian cells express the product of interest and have reduced or eliminated activity of BAX, BAK, LPLA2, LPL, LIPA, PPT1, PLBL2, PLD3, SMPD1, CLU, PRDX1, PLAA, and ACOT13. In certain embodiments, the present disclosure provides a method of producing a product of interest comprising culturing mammalian cells expressing the product of interest, wherein the mammalian cells express the product of interest and have reduced or eliminated activity of LPLA2, LPL, and PPT1. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA and PPT1. In certain embodiments, the present disclosure provides a method of producing a product of interest comprising culturing mammalian cells expressing the product of interest, wherein the mammalian cells express the product of interest and have reduced or eliminated activity of HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of SMPD1, CES1, PLA1A, and SIAE. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, HACH, CES1F/CES-B1L, LYPLA1, SMPD1, CES1, PLA1A, and SIAE. In certain embodiments, the present disclosure provides a method of producing a product of interest comprising culturing mammalian cells expressing the product of interest, wherein the mammalian cells express the product of interest and have reduced or eliminated activity of LPLA2, LMF1, LIPA, PPT1, HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of LPLA2, LMF1, APOC2, LIPA, PPT1, HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of LMF1 and APOC2.

In certain embodiments, the present disclosure provides a method of culturing a population of mammalian cells expressing a product of interest, wherein the mammalian cells have reduced or eliminated activity of PPT1. In certain embodiments, the present disclosure provides a method of culturing a population of mammalian cells expressing a product of interest, wherein the mammalian cells have reduced or eliminated activity of LPLA2, LPL, and LIPA. In certain embodiments, the present disclosure provides a method of culturing a population of mammalian cells expressing a product of interest, wherein the mammalian cells have reduced or eliminated activity of LPLA2, LPL, LIPA, PPT1, PLBL2, PLD3, and SMPD1. In certain embodiments, the present disclosure provides a method of culturing a population of mammalian cells expressing a product of interest, wherein the mammalian cells have reduced or eliminated activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method of culturing a population of mammalian cells expressing a product of interest, wherein the mammalian cells have reduced or eliminated activity of BAX, BAK, LPLA2, LPL, LIPA, PPT1, PLD3, and SMPD1. In certain embodiments, the present disclosure provides a method of culturing a population of mammalian cells expressing a product of interest, wherein the mammalian cells have reduced or eliminated activity of BAX, BAK, LPLA2, LPL, LIPA, PPT1, PLBL2, PLD3, SMPD1, CLU, PRDX1, PLAA, and ACOT13. In certain embodiments, the present disclosure provides a method of culturing a population of mammalian cells expressing a product of interest, wherein the mammalian cells have reduced or eliminated activity of LPLA2, LPL, and PPT1. In certain embodiments, the present disclosure provides a method of culturing a population of mammalian cells expressing a product of interest, wherein the mammalian cells have reduced or eliminated activity of LPLA2, LPL, LIPA and PPT1. In certain embodiments, the present disclosure provides a method of culturing a population of mammalian cells expressing a product of interest, wherein the mammalian cells have reduced or eliminated activity of HACH, CES1F/CES-B1L, and LYPLA1. In certain embodiments, the present disclosure provides a method of culturing a population of mammalian cells expressing a product of interest, wherein the mammalian cells have reduced or eliminated activity of LPLA2, LPL, LIPA, PPT1, HACH, CES1F/CES-B1L, and LYPLA1. In certain embodiments, the present disclosure provides a method of culturing a population of mammalian cells expressing a product of interest, wherein the mammalian cells have reduced or eliminated activity of SMPD1, CES1, PLA1A, and SIAE. In certain embodiments, the present disclosure provides a method of culturing a population of mammalian cells expressing a product of interest, wherein the mammalian cells have reduced or eliminated activity of LPLA2, LPL, LIPA, PPT1, HACH, CES1F/CES-B1L, LYPLA1, SMPD1, CES1, PLA1A, and SIAE. In certain embodiments, the present disclosure provides a method of culturing a population of mammalian cells expressing a product of interest, wherein the mammalian cells have reduced or eliminated activity of LPLA2, LMF1, LIPA, PPT1, HACH, CES1F/CES-B1L, and LYPLA1. In certain embodiments, the present disclosure provides a method of culturing a population of mammalian cells expressing a product of interest, wherein the mammalian cells have reduced or eliminated activity of LPLA2, LMF1, APOC2, LIPA, PPT1, HACH, CES1F/CES-B1L, and LYPLA1. In certain embodiments, the present disclosure provides a method of culturing a population of mammalian cells expressing a product of interest, wherein the mammalian cells have reduced or eliminated activity of LMF1 and APOC2.

4. BRIEF DESCRIPTION OF THE DRAWINGS

FIG. 1. A table showing enzymes found in enriched samples taken from various stages in the purification process of three different monoclonal antibodies.

FIG. 2. A multiplexed Knock Out (KO) approach used for the generation of blank CHO host cells.

FIG. 3. A table showing the genes that have been modulated or knocked out in each blank CHO hosts.

Figures 4A, 4B, 4C:
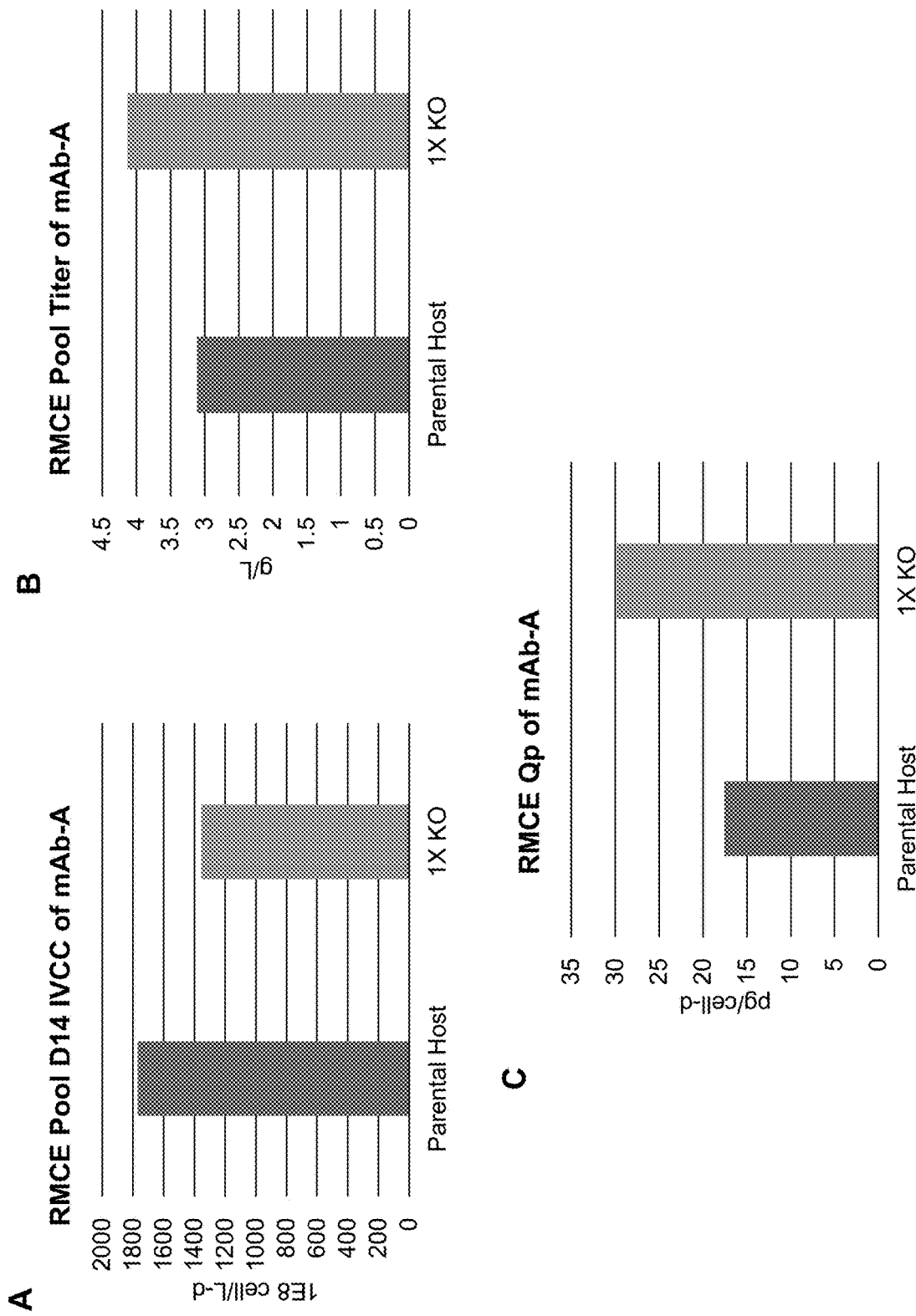

FIGS. 4A-4C. PLBL2 KO cells have similar or better titers compared to the Parental Host cells. Growth rate, as expressed by the integral of viable cell concentration (IVCC), is depicted in FIG. 4A. MAb-A producing pools derived from PLBL2-KO host cell lines had comparable or higher titer compared to the Parental Host cells, as depicted in FIG. 4B due to higher specific productivity (Qp) as depicted in FIG. 4C.

Figures 5A, 5B, 5C:
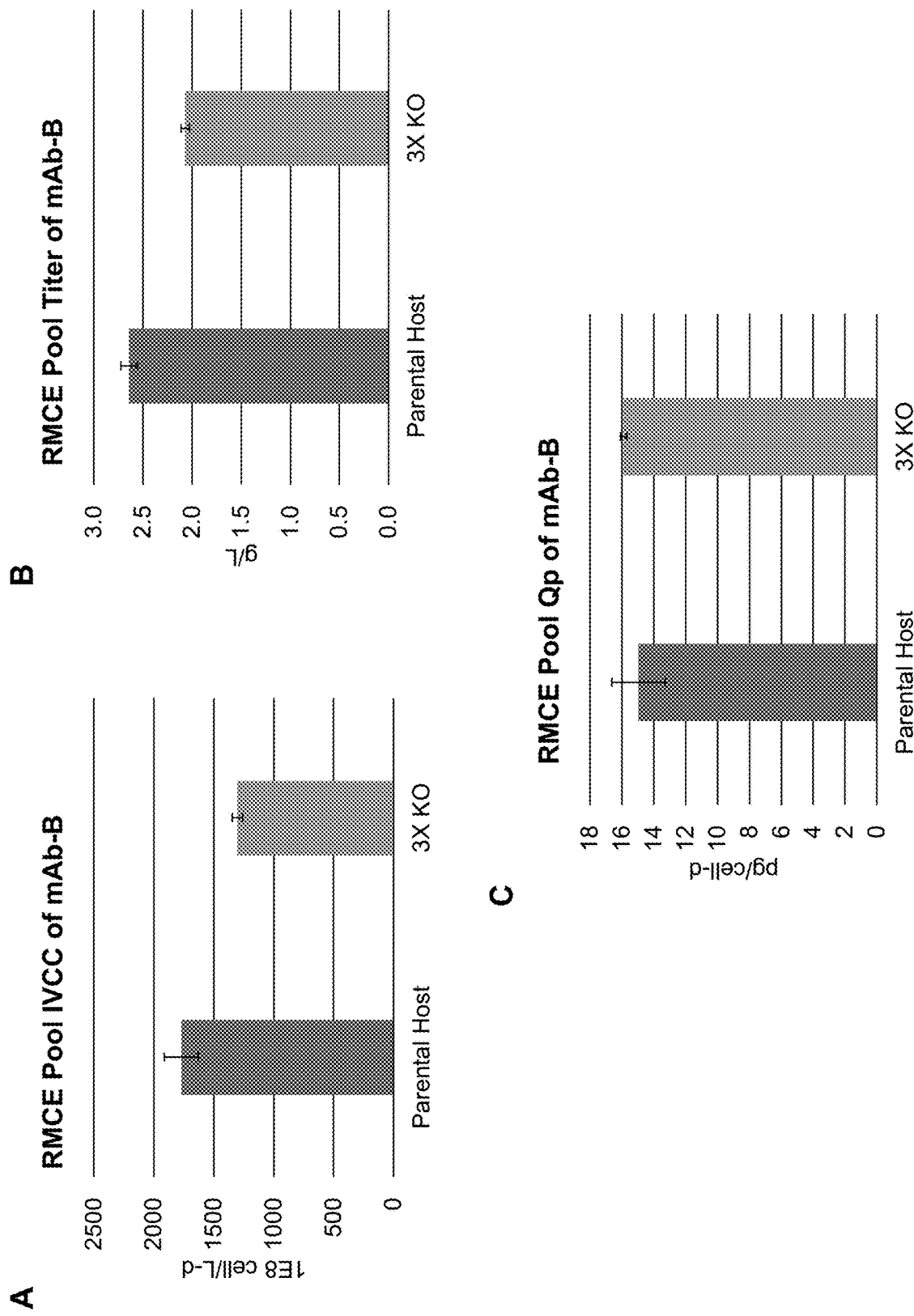

FIGS. 5A-5C. 3× KO cells have similar or better specific productivity (Qp) compared to the Parental Host cells. Growth rate is depicted in FIG. 5A. MAb-B producing pools derived from 3× KO host cell lines are depicted in FIG. 5B. Specific productivity (Qp) of mAb-B depicted in FIG. 5C.

Figures 6A, 6B, 6C:
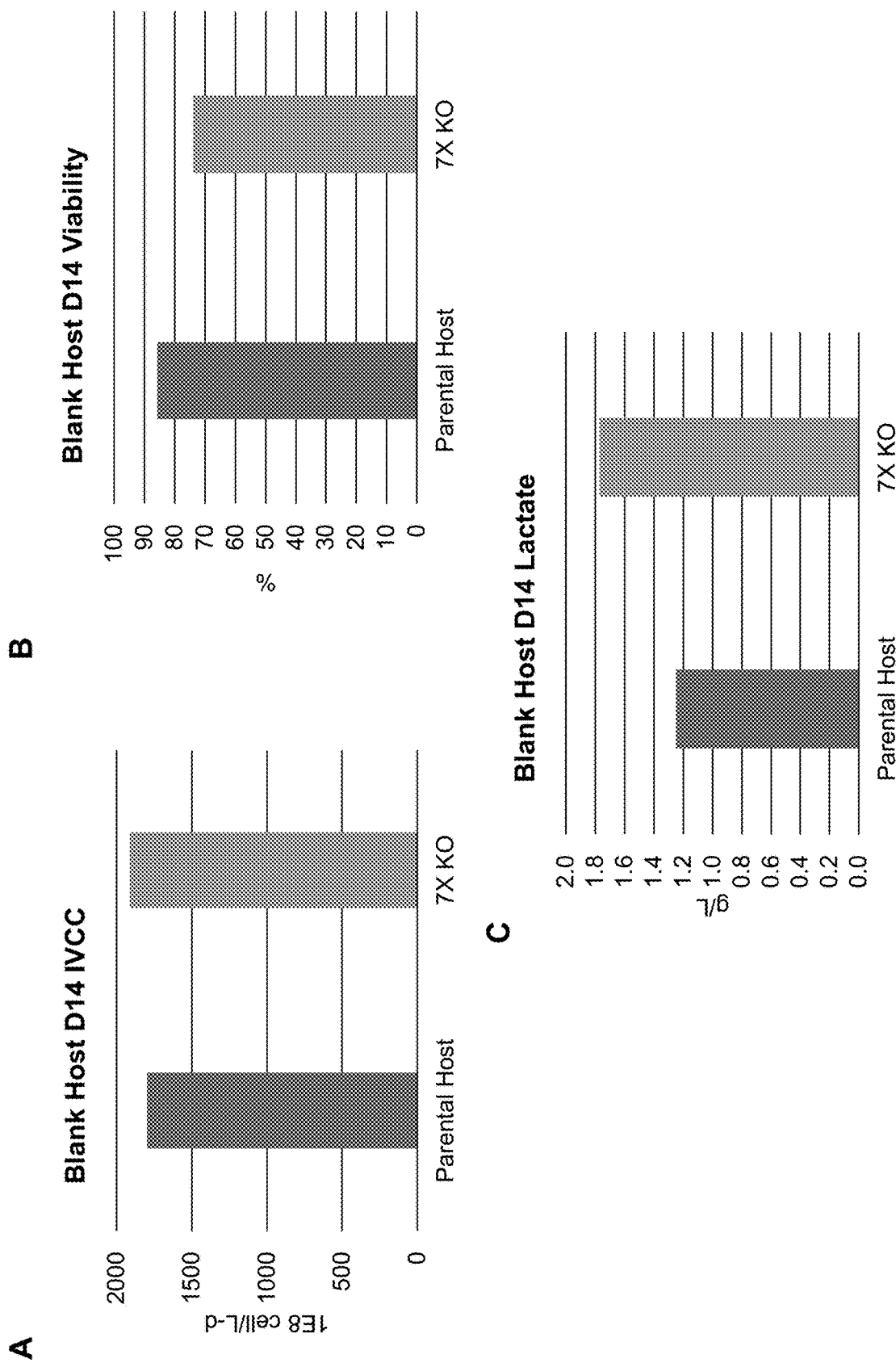

FIGS. 6A-6C. 7× KO blank host performance. Cell growth, as expressed by the integral of viable cell concentration (IVCC), is depicted in FIG. 6A. Viability and lactate accumulation are depicted in FIGS. 6B and 6C, respectively.

Figures 7A, 7B, 7C:
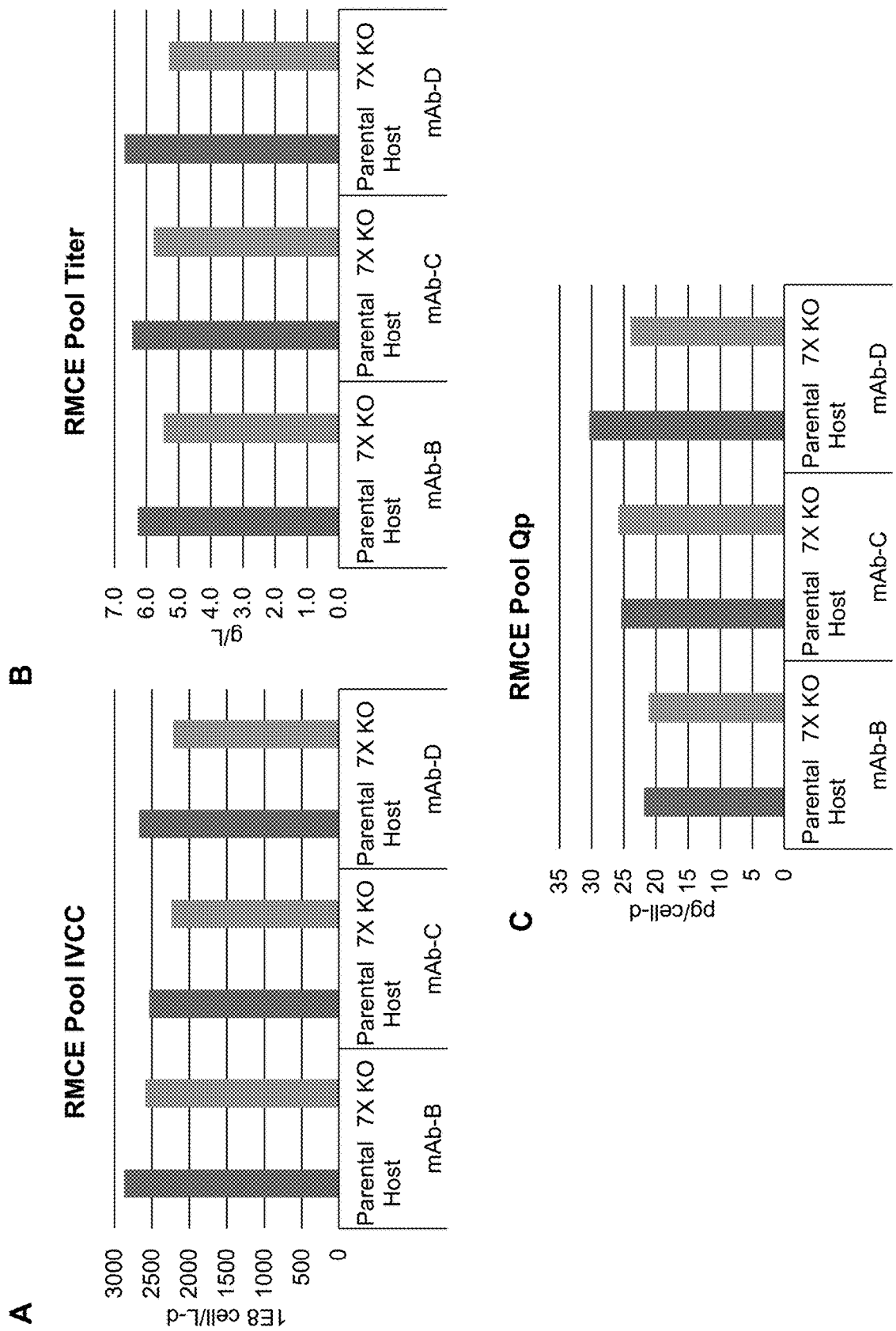

FIGS. 7A-7C. Production of three different antibodies by 7× KO host cells. Growth of 7× KO host cells expressing three different mAbs, as expressed by IVCC, is depicted in FIG. 7A. Titer of three different mAbs expressed by 7× KO host cells is depicted in FIG. 7B. Specific productivity (Qp) of mAb-B, mAb-C and mAb-D is depicted in FIG. 7C.

Figure 8A:
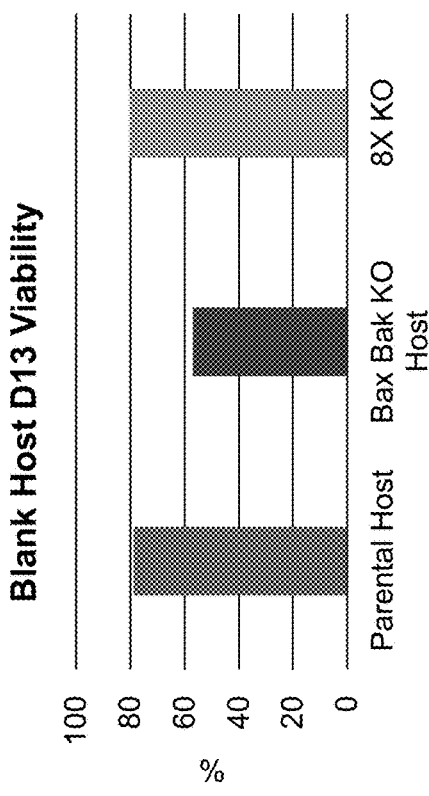
Figure 8B:
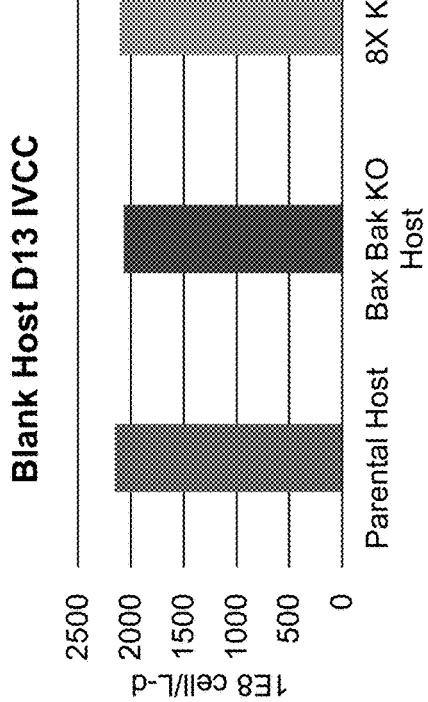
Figure 8C:
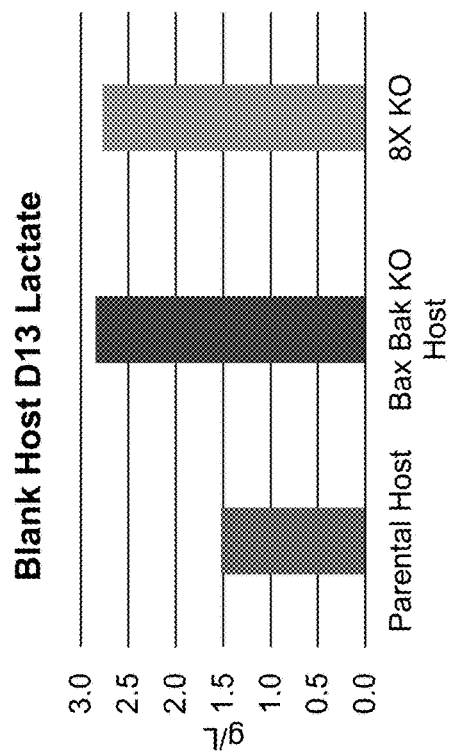

FIGS. 8A-8C. 8× KO and Bax Bak KO blank host performance. Cell growth, as expressed by the integral of viable cell concentration (IVCC), is depicted in FIG. 8A. Viability and lactate accumulation are depicted in FIGS. 8B and 8C, respectively.

Figures 9A, 9B, 9C:
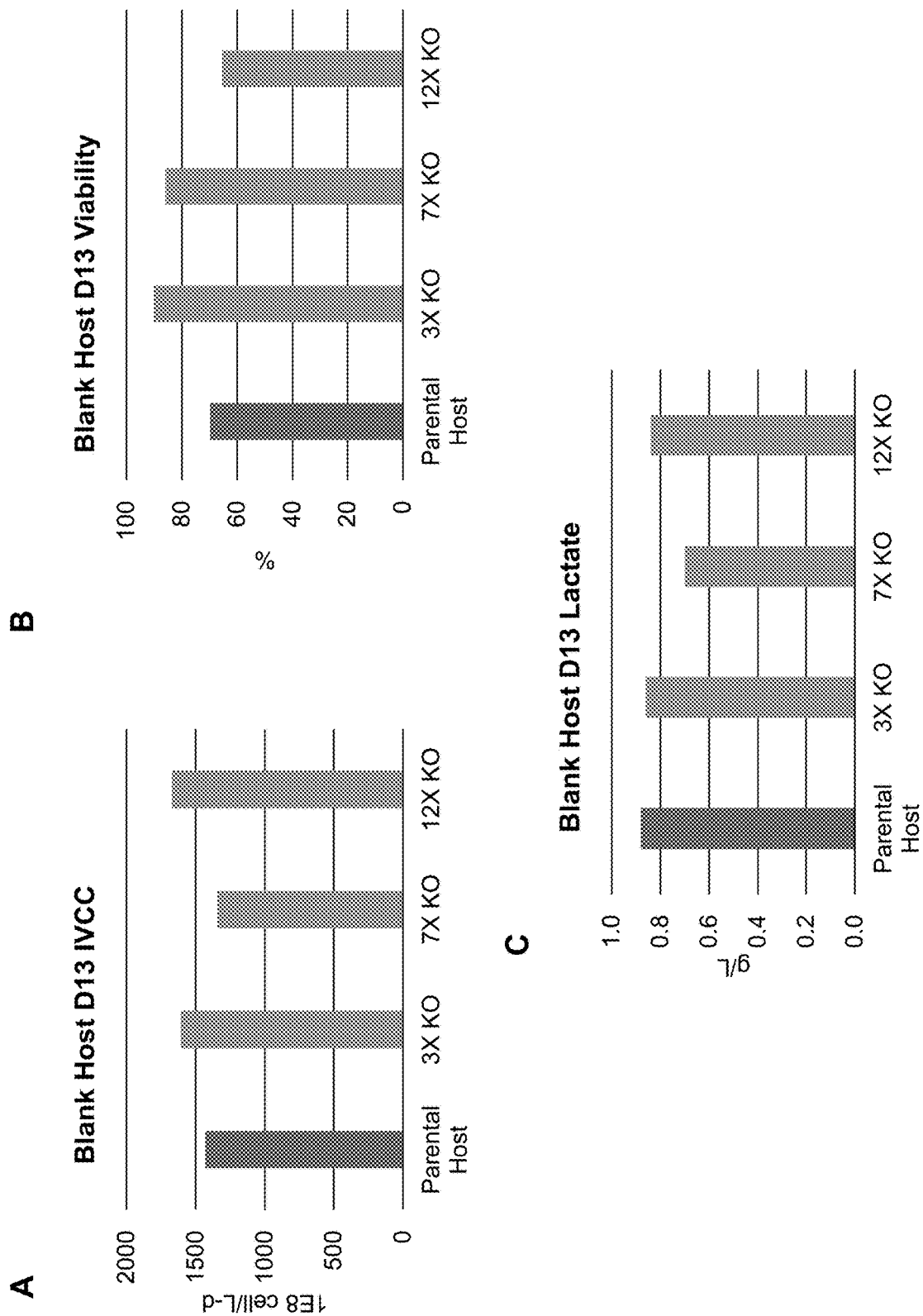

FIGS. 9A-9C. 3×, 7× and 12× KO blank host performance. Cell growth, as expressed by the integral of viable cell concentration (IVCC), is depicted in FIG. 9A. Viability and lactate accumulation are depicted in FIGS. 9B and 9C, respectively.

Figures 10A, 10B, 10C:
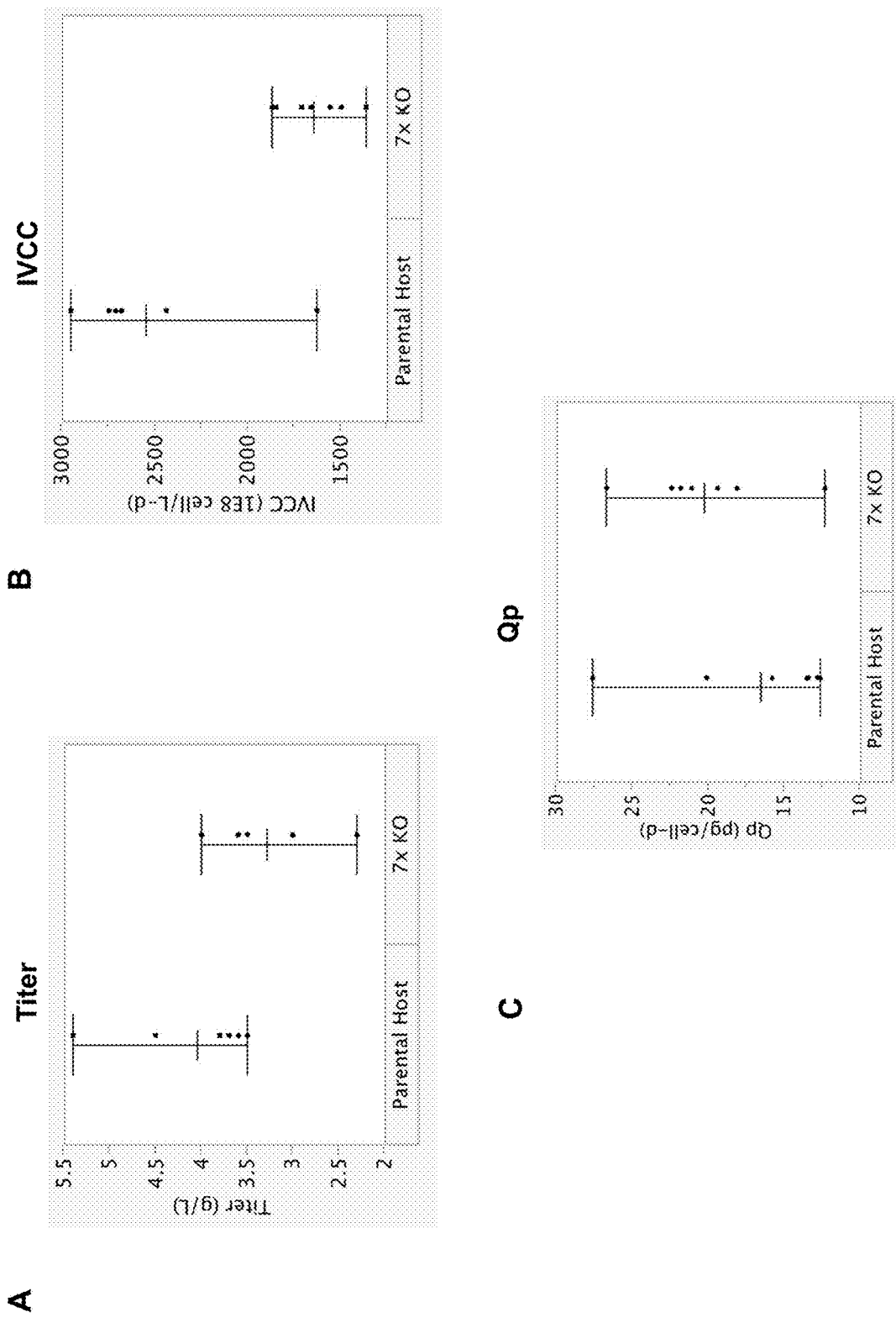

FIGS. 10A-10C. Production of mAb-2 by 7× KO host cell clones. Average D10 titer is depicted in FIG. 10A. Average D10 IVCCs is depicted in FIG. 10B. Average D10 Qp is depicted in FIG. 10C.

Figures 11A, 11B, 11C:
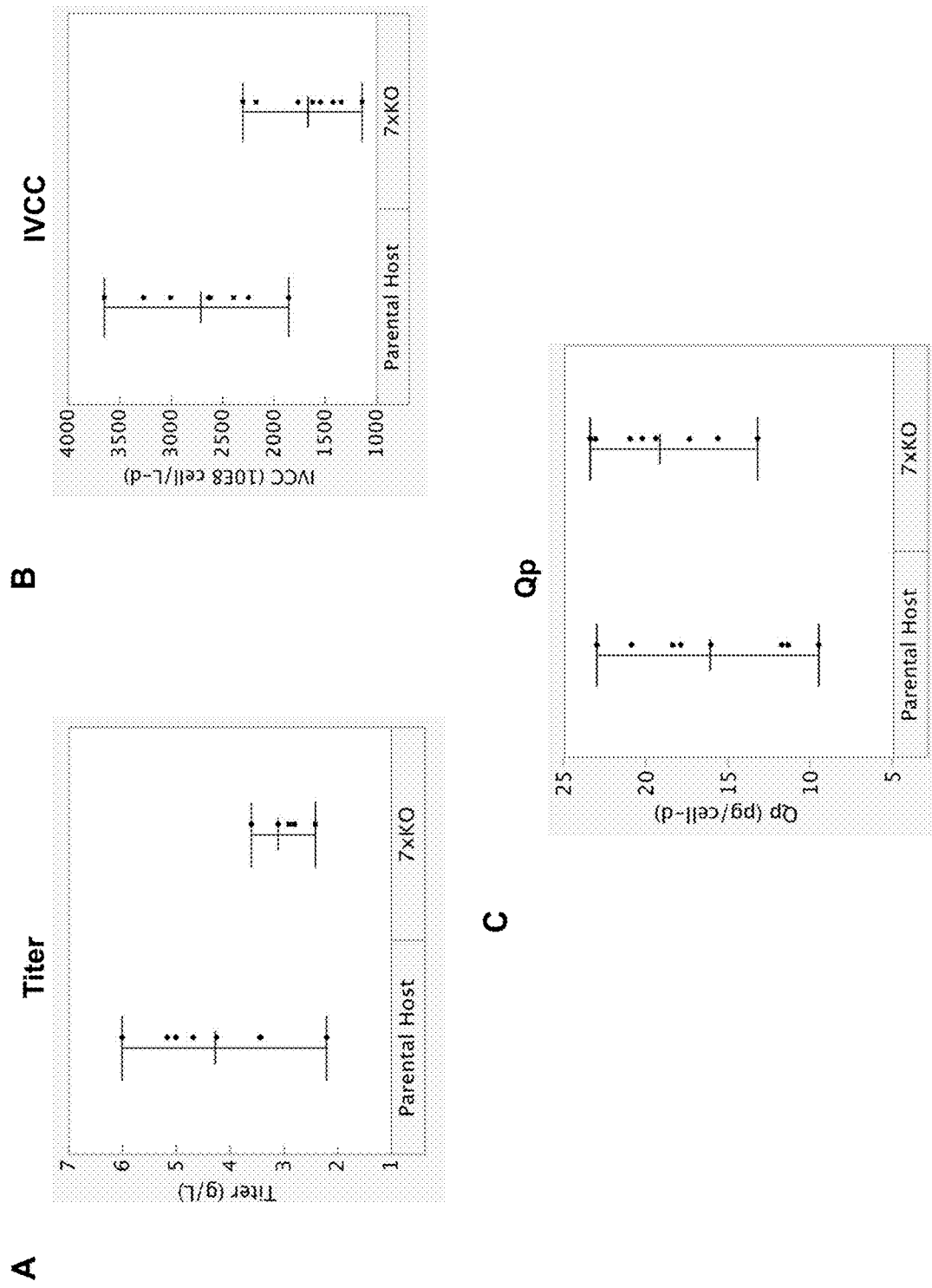

FIGS. 11A-11C. Production of mAb-1 by 7× KO host cell clones. Titer is depicted in FIG. 11A. IVCC is depicted in FIG. 11B. Qp is depicted in FIG. 11C.

Figure 12:
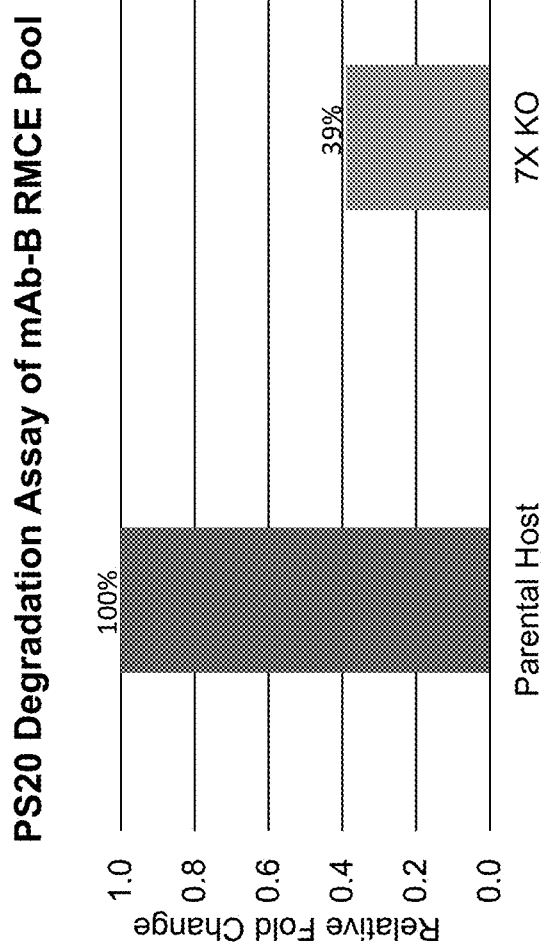
Figures 13A, 13B, 13C, 13D, 13E, 13F, 13G, 13H, 13I, 13J, 13K:
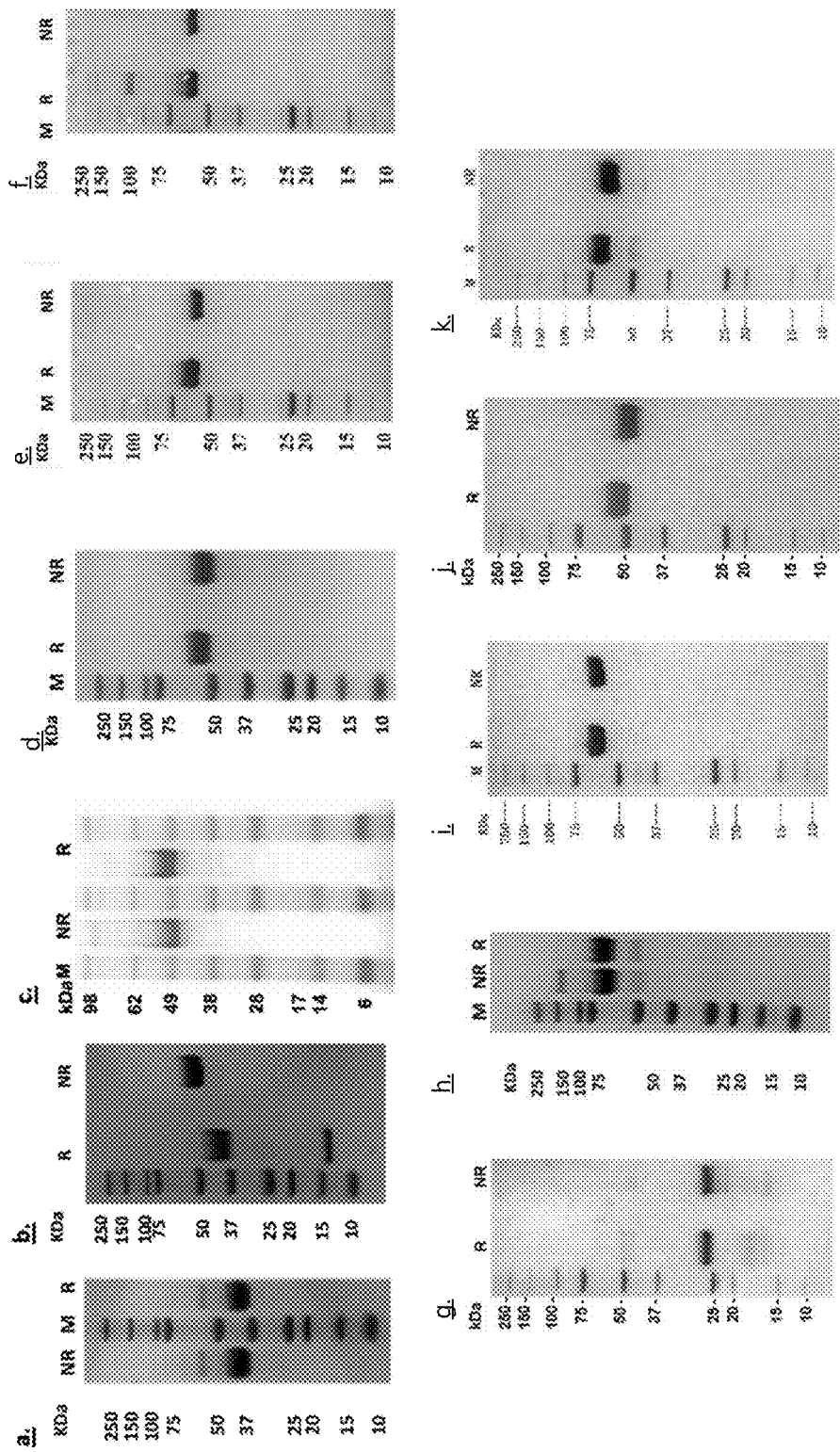

FIG. 12. PS20 degradation. Low PS20 degradation was observed in 7× KO mAb-B producing RMCE Pool.

FIGS. 13A-13K. SDS PAGE for purified enzymes. a. PPT1; b. ASAH1; c. LIPA; d. LPLA1; e. HACH; f. CESB1L; g. LYPLA1; h. SMPD1; i. CES1; j. PLA1A; k. SIAE FIGS. 14A-14C. a. Percentage of initial PS20 concentration, measured by mixed-mode HPLC with ELSD, in solutions of mAb 2 at 30 mg/mL following the addition of recombinantly purified hydrolase enzymes (PPT1, rhLPL, ASAH1, LIPA); b. Percentage of initial PS20 concentration, measured by mixed-mode HPLC with ELSD, in solutions of formulation buffer following the addition of recombinantly purified hydrolase enzymes (HACH, LYPLA1, CES-B1L, LPLA2); c. Percentage of initial PS20 concentration, measured by mixed-mode HPLC with ELSD, in solutions of formulation buffer following the addition of recombinantly purified hydrolase enzymes (PLA1A, SIAE, CES1, SMPD1).

FIG. 15. Effect of lipase/esterase KO on polysorbate degradation in purified mAb samples. Enzymatic activity towards polysorbate degradation in purified samples was assessed by the PS20 degradation assay. Within each mAb, the decrease in PS20 degradation was assessed by comparing the purified materials produced by KO cells to the control cells (i.e., no KO performed). All the KO mAb producing cells were generated by transfecting the CHO blank KO host (either 7× KO or 12× KO, as shown in FIG. 3) with the corresponding mAb gene.

FIG. 16. Effect of lipase/esterase KO on polysorbate degradation in purified mAb T samples. Enzymatic activity towards polysorbate degradation in purified mAb T samples was assessed by the PS20 degradation assay. The decrease in PS20 degradation was assessed by comparing the purified materials produced by KO cells to the control cells (i.e., no KO performed). All the KO cells (1×, 2×, 3× and 6×) were generated by sequentially knocking out lipase/esterase genes in the parental mAb T cell line.

5. DETAILED DESCRIPTION

For clarity, but not by way of limitation, the detailed description of the presently disclosed subject matter is divided into the following subsections:

5.1 Definitions;
5.2 Modulating Enzyme Activity;
5.3 Cells Comprising Gene-Specific Modifications;
5.4 Cell Culture Methods; and
5.5 Products.

5.1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the present disclosure and how to make and use them.

As used herein, the use of the word "a" or "an" when used in conjunction with the term "comprising" in the claims and/or the specification can mean "one," but it is also consistent with the meaning of "one or more," "at least one" and "one or more than one."

The terms "comprise(s)," "include(s)," "having," "has," "can," "contain(s)" and variants thereof, as used herein, are intended to be open-ended transitional phrases, terms or words that do not preclude the possibility of additional acts or structures. The present disclosure also contemplates other embodiments "comprising," "consisting of" and "consisting essentially of," the embodiments or elements presented herein, whether explicitly set forth or not.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value.

Alternatively, particularly with respect to biological systems or processes, the term can mean within an order of magnitude, preferably within 5-fold, and more preferably within 2-fold, of a value.

The terms "cell culture medium" and "culture medium" refer to a nutrient solution used for growing mammalian cells that typically provides at least one component from one or more of the following categories:
1) an energy source, usually in the form of a carbohydrate such as glucose;
2) all essential amino acids, and usually the basic set of twenty amino acids plus cysteine;
3) vitamins and/or other organic compounds required at low concentrations;
4) free fatty acids; and
5) trace elements, where trace elements are defined as inorganic compounds or naturally occurring elements that are typically required at very low concentrations, usually in the micromolar range.

The nutrient solution can optionally be supplemented with one or more components from any of the following categories:
1) hormones and other growth factors as, for example, insulin, transferrin, and epidermal growth factor;
2) salts and buffers as, for example, calcium, magnesium, and phosphate;
3) nucleosides and bases such as, for example, adenosine, thymidine, and hypoxanthine; and
4) protein and tissue hydrolysates.

"Culturing" a cell refers to contacting a cell with a cell culture medium under conditions suitable to the survival and/or growth and/or proliferation of the cell.

"Batch culture" refers to a culture in which all components for cell culturing (including the cells and all culture nutrients) are supplied to the culturing bioreactor at the start of the culturing process.

"Fed-batch cell culture," as used herein refers to a batch culture wherein the cells and culture medium are supplied to the culturing bioreactor initially, and additional culture nutrients are fed, continuously or in discrete increments, to the culture during the culturing process, with or without periodic cell and/or product harvest before termination of culture.

"Perfusion culture," sometimes referred to as continuous culture, is a culture by which the cells are restrained in the culture by, e.g., filtration, encapsulation, anchoring to microcarriers, etc., and the culture medium is continuously, stepwise or intermittently introduced (or any combination of these) and removed from the culturing bioreactor.

As used herein, the term "cell," refers to animal cells, mammalian cells, cultured cells, host cells, recombinant cells and recombinant host cells. Such cells are generally cell lines obtained or derived from mammalian tissues which are able to grow and survive when placed in media containing appropriate nutrients and/or growth factors.

The terms "host cell," "host cell line" and "host cell culture" are used interchangeably and refer to cells into which exogenous nucleic acid may be or has been introduced, including the progeny of such cells. Host cells include "transformants" and "transformed cells," which include the primary transformed cell and progeny derived therefrom without regard to the number of passages. Progeny does not need to be completely identical in nucleic acid content to a parent cell, but can contain mutations. Mutant progeny that have the same function or biological activity as screened or selected for in the originally transformed cell are included herein.

The term "mammalian host cell" or "mammalian cell" refers to cell lines derived from mammals that are capable of growth and survival when placed in either monolayer culture or in suspension culture in a medium containing the appropriate nutrients and growth factors. The necessary growth factors for a particular cell line are readily determined empirically without undue experimentation, as described for example in Mammalian Cell Culture (Mather, J. P. ed., Plenum Press, N.Y. 1984), and Barnes and Sato, (1980) Cell, 22:649. Typically, the cells are capable of expressing and secreting large quantities of a particular protein, e.g., glycoprotein, of interest into the culture medium. Examples of suitable mammalian host cells within the context of the present disclosure can include Chinese hamster ovary cells/−DHFR (CHO, Urlaub and Chasin, Proc. Natl. Acad. Sci. USA, 77:4216 1980); dp12.CHO cells (EP 307,247 published 15 Mar. 1989); CHO-K1 (ATCC, CCL-61); monkey kidney CV1 line transformed by SV40 (COS-7, ATCC CRL 1651); human embryonic kidney line (293 or 293 cells subcloned for growth in suspension culture, Graham et al., J. Gen Virol., 36:59 1977); baby hamster kidney cells (BHK, ATCC CCL 10); mouse sertoli cells (TM4, Mather, Biol. Reprod., 23:243-251 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 1982); MRC 5 cells; FS4 cells; and a human hepatoma line (Hep G2). In certain embodiments, the mammalian cells include Chinese hamster ovary cells/−DHFR (CHO, Urlaub and Chasin, Proc. Natl. Acad. Sci. USA, 77:4216 1980); dp12.CHO cells (EP 307, 247 published 15 Mar. 1989).

"Growth phase" of the cell culture refers to the period of exponential cell growth (the log phase) where cells are generally rapidly dividing. The duration of time for which the cells are maintained at growth phase can vary based on the cell-type, the rate of growth of cells and/or the culture conditions, for example. In certain embodiments, during this phase, cells are cultured for a period of time, usually between 1-4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. In certain embodiments, during the growth phase, cells are cultured in nutrient medium containing the necessary additives generally at about 30°-40° C. in a humidified, controlled atmosphere, such that optimal growth is achieved for the particular cell line. In certain embodiments, cells are maintained in the growth phase for a period of about between one and four days, usually between two to three days.

"Production phase" of the cell culture refers to the period of time during which cell growth is/has plateaued. The logarithmic cell growth typically decreases before or during this phase and protein production takes over. During the production phase, logarithmic cell growth has ended, and protein production is primary. During this period of time the medium is generally supplemented to support continued protein production and to achieve the desired glycoprotein product. Fed-batch and/or perfusion cell culture processes supplement the cell culture medium or provide fresh medium during this phase to achieve and/or maintain desired cell density, viability and/or recombinant protein product titer. A production phase can be conducted at large scale.

The term "activity" as used herein with respect to activity of a protein refers to any activity of a protein including, but not limited to, enzymatic activity, ligand binding, drug transport, ion transport, protein localization, receptor binding, and/or structural activity. Such activity can be modulated, e.g., reduced or eliminated, by reducing or eliminating the expression of the protein, thereby reducing or eliminating the presence of the protein. Such activity can also be modulated, e.g., reduced or eliminated, by altering the nucleic acid sequence encoding the protein such that the resulting modified protein exhibits reduced or eliminated activity relative to a wild type protein.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

As used herein, "polypeptide" refers generally to peptides and proteins having more than about ten amino acids. The polypeptides can be homologous to the host cell, or preferably, can be exogenous, meaning that they are heterologous, i.e., foreign, to the host cell being utilized, such as a human protein produced by a Chinese hamster ovary cell, or a yeast polypeptide produced by a mammalian cell. In certain embodiments, mammalian polypeptides (polypeptides that were originally derived from a mammalian organism) are used, more preferably those which are directly secreted into the medium.

The term "protein" is meant to refer to a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD. Examples of proteins encompassed within the definition herein include host cell proteins as well as all mammalian proteins, in particular, therapeutic and diagnostic proteins, such as therapeutic and diagnostic antibodies, and, in general proteins that contain one or more disulfide bonds, including multi-chain polypeptides comprising one or more inter- and/or intrachain disulfide bonds.

The term "antibody" is used herein in the broadest sense and encompasses various antibody structures including, but not limited to, monoclonal antibodies, polyclonal antibodies, monospecific antibodies (e.g., antibodies consisting of a single heavy chain sequence and a single light chain sequence, including multimers of such pairings), multispecific antibodies (e.g., bispecific antibodies) and antibody fragments so long as they exhibit the desired antigen-binding activity.

An "antibody fragment," "antigen-binding portion" of an antibody (or simply "antibody portion") or "antigen-binding fragment" of an antibody, as used herein, refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG and IgM, and several of these can be further divided into subclasses (isotypes), e.g., IgG$_1$, IgG$_2$, IgG$_3$, IgG$_4$, IgA$_1$, and IgA$_2$. In certain embodiments, the antibody is of the IgG$_1$ isotype. In certain embodiments, the antibody is of the IgG$_2$ isotype. The heavy chain constant domains that correspond to the different classes of immunoglobulins are called α, δ, ε, γ and μ, respectively. The light chain of an antibody can be assigned to one of two types, called kappa (κ) and lambda (λ), based on the amino acid sequence of its constant domain.

The term "titer" as used herein refers to the total amount of recombinantly expressed antibody produced by a cell culture divided by a given amount of medium volume. Titer is typically expressed in units of milligrams of antibody per milliliter or liter of medium (mg/ml or mg/L). In certain embodiments, titer is expressed in grams of antibody per liter of medium (g/L). Titer can be expressed or assessed in terms of a relative measurement, such as a percentage increase in titer as compared obtaining the protein product under different culture conditions.

The term "nucleic acid," "nucleic acid molecule" or "polynucleotide" includes any compound and/or substance that comprises a polymer of nucleotides. Each nucleotide is composed of a base, specifically a purine- or pyrimidine base (i.e., cytosine (C), guanine (G), adenine (A), thymine (T) or uracil (U)), a sugar (i.e., deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including, e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule can be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the disclosure in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see, e.g., Stadler et al, Nature Medicine 2017, published online 12 Jun. 2017, doi:10.1038/nm.4356 or EP 2 101 823 B1).

As used herein, the term "vector" refers to a nucleic acid molecule capable of transporting another nucleic acid to which it has been linked.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally can comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:
(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991)); and
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

An "immunoconjugate" is an antibody conjugated to one or more heterologous molecule(s), including but not limited to a cytotoxic agent.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the presently disclosed subject matter can be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). (See, e.g., Kindt et al. *Kuby Immunology*, 6$^{th}$ ed., W.H. Freeman and Co., page 91 (2007).) A single VH or VL domain can be sufficient to confer antigen-binding specificity. Furthermore, antibodies that bind a particular antigen can be isolated using a VH or VL domain from an antibody that binds the antigen to screen a library of complementary VL or VH domains, respectively. See, e.g., Portolano et al., *J. Immunol.* 150:880-887 (1993); Clarkson et al., Nature 352:624-628 (1991).

As used herein, the term "cell density" refers to the number of cells in a given volume of medium. In certain embodiments, a high cell density is desirable in that it can lead to higher protein productivity. Cell density can be monitored by any technique known in the art, including, but not limited to, extracting samples from a culture and analyzing the cells under a microscope, using a commercially available cell counting device or by using a commercially available suitable probe introduced into the bioreactor itself (or into a loop through which the medium and suspended cells are passed and then returned to the bioreactor).

As used herein, the term "recombinant cell" refers to cells which have some genetic modification from the original parent cells from which they are derived. Such genetic modification can be the result of an introduction of a heterologous gene for expression of the gene product, e.g., a recombinant protein.

As used herein, the term "recombinant protein" refers generally to peptides and proteins, including antibodies. Such recombinant proteins are "heterologous," i.e., foreign to the host cell being utilized, such as an antibody produced by CHO cells.

The term "PS20" refers to polysorbate 20 or Tween 20. The term "PS80" refers to polysorbate 80 or Tween 80. PS20 and PS80 are polysorbate surfactants with a fatty acid ester moiety and a long polyoxyethylene chain.

5.2. Modulating Enzyme Activity

In certain embodiments, the present disclosure relates to methods for modulating the activity of one or more host cell proteins, e.g., an enzyme activity, including but not limited to, a lipase, esterase, or hydrolase. For example, but not by way of limitation, methods for modulating enzyme activity, including but not limited to lipase, esterase, and/or hydrolase proteins, in a host cell include reducing or eliminating the activity of the corresponding polypeptide. In certain embodiments, a recombinant host cell is modified to reduce or eliminate the activity of one or more host cell protein relative to the activity of the protein in an unmodified cell. In certain embodiments, the activity of Lipoprotein lipase (LPL); Phospholipase B-domain containing (PLBL2/PLBD2); Lipase A (Lysosomal acid lipase/cholesteryl ester hydrolase, Lipase) (LIPA); Phospholipase A-2-activating protein (PLAA); Phospholipase D3 (PLD3); Phospholipase A2 group (LPLA2); Phospholipase C beta 1 (PLCB1); Phospholipase C delta 1 (PLCD1); DDHD domain containing protein 1 (Fragment) (DDHD1); Lysophospholipase-like protein 1 (LYPLA1); Phospholipase A2 group XIIA (PLA2G12A); Peroxiredoxin 6 (PRDX6); Sphingomyelin phosphodiesterase (SMPD1); Palmitoyl-protein thioesterase 1 (PPT1); Isoamyl acetate hydrolyzing esterase 1 (IAH1); OTU deubiquitinase, ubiquitin aldehyde binding 1 (OTUB1); Lysophospholipase 2 (Acyl-protein thioesterase 2) (LYPLA2); Acyl-coenzyme A thioesterase 13 (ACOT13); Fatty acid synthase (FASN); Phospholipase A2 group VII (PLA2G7); Ubiquitin specific peptidase 5 (USP5); N-acyl-sphingosine amidohydrolase 1 (Acid ceramidase) (ASAH1); Lipase maturation factor 1 (LMF1); Apolipoprotein-CII (APOC2); Acylcarnitine hydrolase (HACH); Carboxylesterase 1F (CES1F) or Liver carboxylesterase B-1-like (CES-B1L); Lysophospholipase 1 (LYPLA1); Carboxylesterase 1 (CES1); Phospholipase A1 member A (PLA1A); and Sialic acid acetylesterase (SIAE) is reduced or eliminated.

In certain embodiments, the activity of PPT1 is reduced or eliminated. In certain embodiments, the activity of LPLA2; LPL; and LIPA is reduced or eliminated. In certain embodiments, the activity of LPLA2; LPL; LIPA; PPT1; PLBL2; PLD3; and SMPD1 is reduced or eliminated. In certain embodiments, the activity of LPLA2; LPL; LIPA; PPT1; PLBL2; PLD3; SMPD1; PLAA; IAH1; OTUB1; LYPLA2; and PLA2G12A is reduced or eliminated. In certain embodiments, the activity of BAX; BAK; LPLA2; LPL; LIPA; PPT1; PLD3; and SPD1 is reduced or eliminated. In certain embodiments, the activity of BAX; BAK; LPLA2; LPL; LIPA; PPT1; PLBL2; PLD3; SPD1; CLU; PRDX1; PLAA; and ACOT13 is reduced or eliminated. In certain embodiments, the activity of LPLA2; LPL; and PPT1 is reduced or eliminated. In certain embodiments, the activity of LPLA2; LPL; LIPA; and PPT1 is reduced or eliminated. In certain embodiments, the activity of HACH; CES1F/CES-B1L; and LYPLA1 is reduced or eliminated. In certain embodiments, the activity of LPLA2; LPL; LIPA; PPT1; HACH; CES1F/CES-B1L; and LYPLA1 is reduced or eliminated. In certain embodiments, the activity of SMPD1; CES1; PLA1A; and SIAE is reduced or eliminated. In certain embodiments, the activity of LPLA2; LPL; LIPA; PPT1; HACH; CES1F/CES-B1L; LYPLA1; SMPD1; CES1; PLA1A; and SIAE is reduced or eliminated. In certain embodiments, the activity of LPLA2; LMF1; LIPA; PPT1; HACH; CES1F/CES-B1L; and LYPLA1 is reduced or eliminated. In certain embodiments, the activity of LPLA2; LMF1; APOC2; LIPA; PPT1; HACH; CES1F/CES-B1L; and LYPLA1 is reduced or eliminated. In certain embodiments, the activity of LMF1 and APOC2 is reduced or eliminated.

In certain embodiments, the reference cells are cells where the activity of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, is not modulated, e.g., reduced or eliminated. In certain embodiments, a reference cell is a cell that comprises at least one or both wild-type alleles of the gene(s) coding for a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE. For example, but not by way of limitation, a reference cell is a cell that has both wild-type alleles of the gene(s) coding for a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE. In certain embodiments, the reference cells are WT CHO cells.

In certain embodiments, the activity of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to reduce or eliminate the activity of the polypeptide is less than about 90%, less than about 80%, less than about 70%, less than about 60%, less than about 50%, less than about 40%, less than about 30%, less than about 20%, less than about 10%, less than about 5%, less than about 4%, less than about 3%, less than about 2% or less than about 1% of the corresponding polypeptide activity of a reference cell, e.g., a WT CHO cell. In certain embodiments, the activity of a polypeptide in a cell that has been modified to reduce or eliminate the activity of the polypeptide is less than about 90%, less than about 80%, less than about 70%, less than about 60%, less than about 50%, less than about 40%, less than about 30%, less than about 20%, less than about 10%, less than about 5%, less than about 4%, less than about 3%, less than about 2%, or less than about 1% of the corresponding polypeptide activity of a reference cell, e.g., a WT CHO cell.

In certain embodiments, the activity of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to reduce or eliminate the activity of the polypeptide is at least about 90%, at least about 80%, at least about 70%, at least about 60%, at least about 50%, at least about 40%, at least about 30%, at least about 20%, at least about 10%, at least about 5%, at least about 4%, at least about 3%, at least about 2% or at least about 1% of the corresponding polypeptide activity of a reference cell, e.g., a WT CHO cell.

In certain embodiments, the activity of a polypeptide in a cell that has been modified to reduce or eliminate the activity of the polypeptide is at least about 90%, at least about 80%, at least about 70%, at least about 60%, at least about 50%, at least about 40%, at least about 30%, at least about 20%, at least about 10%, at least about 5%, at least about 4%, at least about 3%, at least about 2%, or at least about 1% of the corresponding polypeptide activity of a reference cell, e.g., a WT CHO cell.

In certain embodiments, the activity of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to reduce or eliminate the activity of the polypeptide is no more than about 90%, no more than about 80%, no more than about 70%, no more than about 60%, no more than about 50%, no more than about 40%, no more than about 30%, no more than about 20%, no more than about 10%, no more than about 5%, no more than about 4%, no more than about 3%, no more than about 2% or no more than about 1% of the corresponding polypeptide activity of a reference cell, e.g., a WT CHO cell. In certain embodiments, the activity of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to reduce or eliminate the activity of the polypeptide is no more than about 40% of the corresponding polypeptide activity of a reference cell, e.g., a WT CHO cell. In certain embodiments, the activity of a polypeptide in a cell that has been modified to reduce or eliminate the activity of the polypeptide is no more than about 90%, no more than about 80%, no more than about 70%, no more than about 60%, no more than about 50%, no more than about 40%, no more than about 30%, no more than about 20%, no more than about 10%, no more than about 5%, no more than about 4%, no more than about 3%, no more than about 2% or no more than about 1% of the corresponding polypeptide activity of a reference cell, e.g., a WT CHO cell.

In certain embodiments, the activity of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to reduce or eliminate the activity of the polypeptide is between about 1% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 1% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 1% and about 70%, between about 10% and about 70%, between about 20% and about 70%, between about 30% and about 70%, between about 40% and about 70%, between about 50% and about 70%, between about 60% and about 70%, between about 65% and about 70%, between about 1% and about 60%, between about 10% and about 60%, between about 20% and about 60%, between about 30% and about 60%, between about 40% and about 60%, between about 50% and about 60%, between about 55% and about 60%, between about 1% and about 50%, between about 10% and about 50%, between about 20% and about 50%, between about 30% and about 50%, between about 40% and about 50%, between about 45% and about 50%, between about 1% and about 40%, between about 10% and about 40%, between about 20% and about 40%, between about 30% and about 40%, between about 35% and about 40%, between about 1% and about 30%, between about 10% and about 30%, between about 20% and about 30%, between about 25% and about 30%, between about 1% and about 20%, between about 5% and about 20%, between about 10% and about 20%, between about 15% and about 20%, between about 1% and about 10%, between about 5% and about 10%, between about 5% and about 20%, between about 5% and about 30%, between about 5% and about 40% of the corresponding polypeptide activity of a reference cell, e.g., a WT CHO cell. In certain embodiments, the activity of a polypeptide in a cell that has been modified to reduce or eliminate the activity of the polypeptide is between about 1% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 1% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 1% and about 70%, between about 10% and about 70%, between about 20% and about 70%, between about 30% and about 70%, between about 40% and about 70%, between about 50% and about 70%, between about 60% and about 70%, between about 65% and about 70%, between about 1% and about 60%, between about 10% and about 60%, between about 20% and about 60%, between about 30% and about 60%, between about 40% and about 60%, between about 50% and about 60%, between about 55% and about 60%, between about 1% and about 50%, between about 10% and about 50%, between about 20% and about 50%, between about 30% and about 50%, between about 40% and about 50%, between about 45% and about 50%, between about 1% and about 40%, between about 10% and about 40%, between about 20% and about 40%, between about 30% and about 40%, between about 35% and about 40%, between about 1% and about 30%, between about 10% and about 30%, between about 20% and about 30%, between about 25% and about 30%, between about 1% and about 20%, between about 5% and about 20%, between about 10% and about 20%, between about 15% and about 20%, between about 1% and about 10%, between about 5% and about 10%, between about 5% and about 20%, between about 5% and about 30%, between about 5% and about 40% of the corresponding polypeptide activity of a reference cell, e.g., a WT CHO cell.

In certain embodiments, the activity of a polypeptide, e.g., a BAX; BAK; LPL; PLBL2/PLBD2; LIPA; PLAA; PLD3;

LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to reduce or eliminate the activity of the polypeptide is between about 5% and about 40% of the corresponding polypeptide activity of a reference cell, e.g., a WT CHO cell. In certain embodiments, the activity of a polypeptide in a cell that has been modified to reduce or eliminate the activity of the polypeptide is between about 5% and about 40% of the corresponding polypeptide activity of a reference cell, e.g., a WT CHO cell. The activity of the polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in different reference cells (e.g., cells that comprise at least one or both wild-type alleles of the corresponding gene) can vary.

In certain embodiments, a genetic engineering system is employed to modulate (e.g., reduce or eliminate) the activity of a particular polypeptide (e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE activity). Various genetic engineering systems known in the art can be used for the methods disclosed herein. Non-limiting examples of such systems include the CRISPR/Cas system, the zinc-finger nuclease (ZFN) system, the transcription activator-like effector nuclease (TALEN) system and the use of other tools for protein knockdown by gene silencing, such as small interfering RNAs (siRNAs), short hairpin RNA (shRNA), and microRNA (miRNA). Any CRISPR/Cas systems known in the art, including traditional, enhanced or modified Cas systems, as well as other bacterial based genome excising tools such as Cpf-1 can be used with the methods disclosed herein.

In certain embodiments, a portion of a gene, e.g., a gene coding for a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, is modified to modulate, e.g., reduce or eliminate the activity of the corresponding polypeptide. In certain embodiments, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or at least about 90% of the gene is modified. In certain embodiments, no more than about 2%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, no more than about 85% or no more than about 90% of the gene is modified. In certain embodiments, between about 2% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 2% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 2% and about 70%, between about 10% and about 70%, between about 20% and about 70%, between about 30% and about 70%, between about 40% and about 70%, between about 50% and about 70%, between about 60% and about 70%, between about 65% and about 70%, between about 2% and about 60%, between about 10% and about 60%, between about 20% and about 60%, between about 30% and about 60%, between about 40% and about 60%, between about 50% and about 60%, between about 55% and about 60%, between about 2% and about 50%, between about 10% and about 50%, between about 20% and about 50%, between about 30% and about 50%, between about 40% and about 50%, between about 45% and about 50%, between about 2% and about 40%, between about 10% and about 40%, between about 20% and about 40%, between about 30% and about 40%, between about 35% and about 40%, between about 2% and about 30%, between about 10% and about 30%, between about 20% and about 30%, between about 25% and about 30%, between about 2% and about 20%, between about 5% and about 20%, between about 10% and about 20%, between about 15% and about 20%, between about 2% and about 10%, between about 5% and about 10%, or between about 2% and about 5% of the gene is modified.

In certain embodiments, the present disclosure relates to methods for modulating the activity of one or more genes in a host cell, e.g., a gene encoding an enzyme, including but not limited to, a lipase, esterase, or hydrolase. For example, but not by way of limitation, methods for modulating the activity of one or more enzyme genes, including but not limited to, lipase, esterase, and/or hydrolase genes in a host cell include knocking out or knocking down the corresponding polypeptide expression in the cell. In certain embodiments, the expression of LPL; PLBL2/PLBD2; LIPA; PLAA; PLD3; (LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE is knocked down or knocked out. In certain embodiments, the expression of PLBL2 is knocked down or knocked out. In certain embodiments, the expression of LPLA2; LPL; and LIPA is knocked down or knocked out. In certain embodiments, the expression of LPLA2; LPL; LIPA; PPT1; PLBL2; PLD3; and SMPD1 is knocked down or knocked out. In certain embodiments, the expression of LPLA2; LPL; LIPA; PPT1; PLBL2; PLD3; SMPD1; PLAA; IAH1; OTUB1; LYPLA2; and PLA2G12A is knocked down or knocked out. In certain embodiments, the expression of BAX; BAK; LPLA2; LPL; LIPA; PPT1; PLD3; and SMPD1 is knocked down or knocked out. In certain embodiments, the expression of BAX; BAK; LPLA2; LPL; LIPA; PPT1; PLBL2; PLD3; SMPD1; CLU; PRDX1; PLAA; and ACOT13 is knocked down or knocked out. In certain embodiments, the expression of LPLA2; LPL; and PPT1 is knocked down or knocked out. In certain embodiments, the expression of LPLA2; LPL; LIPA; and PPT1 is knocked down or knocked out. In certain embodiments, the expression of HACH; CES1F/CES-B1L; and LYPLA1 is knocked down or knocked out. In certain embodiments, the expression of LPLA2; LPL; LIPA; PPT1; HACH; CES1F/CES-B1L; and LYPLA1 is knocked down or knocked out. In certain embodiments, the expression of SMPD1; CES1; PLA1A; and SIAE is knocked down or knocked out. In certain embodiments, the expression of LPLA2; LPL; LIPA; PPT1; HACH; CES1F/CES-B1L; LYPLA1; SMPD1; CES1; PLA1A; and SIAE is knocked down or knocked out. In certain embodiments, the expression of LPLA2; LMF1; LIPA; PPT1; HACH; CES1F/CES-B1L; and LYPLA1 is knocked down or knocked out. In certain embodiments, the expression of LPLA2; LMF1; APOC2; LIPA; PPT1; HACH; CES1F/CES-B1L; and LYPLA1 is knocked down or knocked out. In certain embodiments, the expression of LMF1 and APOC2 is knocked down or knocked out. As used herein, knocked out expression refers to the elimination of the expression of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in the cell as compared to a reference cell. As used herein, knocked down expression refers to a reduction in the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in the cell as compared to a reference cell.

In certain embodiments, the reference cells are cells where the expression of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, is not modulated, e.g., reduced. In certain embodiments, a reference cell is a cell that comprises at least one or both wild-type alleles of the gene(s) coding for a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE. For example, but not by way of limitation, a reference cell is a cell that has both wild-type alleles of the gene(s) coding for a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE. In certain embodiments, the reference cells are WT CHO cells.

In certain embodiments, the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to knock down expression of the polypeptide is less than about 90%, less than about 80%, less than about 70%, less than about 60%, less than about 50%, less than about 40%, less than about 30%, less than about 20%, less than about 10%, less than about 5%, less than about 4%, less than about 3%, less than about 2% or less than about 1% of the corresponding polypeptide expression of a reference cell, e.g., a WT CHO cell. In certain embodiments, the expression of a polypeptide in a cell that has been modified to knock down expression of the polypeptide is less than about 90%, less than about 80%, less than about 70%, less than about 60%, less than about 50%, less than about 40%, less than about 30%, less than about 20%, less than about 10%, less than about 5%, less than about 4%, less than about 3%, less than about 2%, or less than about 1% of the corresponding polypeptide expression of a reference cell, e.g., a WT CHO cell.

In certain embodiments, the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to knock down expression of the polypeptide is at least about 90%, at least about 80%, at least about 70%, at least about 60%, at least about 50%, at least about 40%, at least about 30%, at least about 20%, at least about 10%, at least about 5%, at least about 4%, at least about 3%, at least about 2% or at least about 1% of the corresponding polypeptide expression of a reference cell, e.g., a WT CHO cell. In certain embodiments, the expression of a polypeptide in a cell that has been modified to knock down expression of the polypeptide is at least about 90%, at least about 80%, at least about 70%, at least about 60%, at least about 50%, at least about 40%, at least about 30%, at least about 20%, at least about 10%, at least about 5%, at least about 4%, at least about 3%, at least about 2%, or at least about 1% of the corresponding polypeptide expression of a reference cell, e.g., a WT CHO cell. In certain embodiments, the expression of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to knock down expression of the polypeptide is no more than about 90%, no more than about 80%, no more than about 70%, no more than about 60%, no more than about 50%, no more than about 40%, no more than about 30%, no more than about 20%, no more than about 10%, no more than about 5%, no more than about 4%, no more than about 3%, no more than about 2% or no more than about 1% of the corresponding polypeptide expression of a reference cell, e.g., a WT CHO cell. In certain embodiments, the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to knock down expression of the polypeptide is no more than about 40% of the corresponding polypeptide expression of a reference cell, e.g., a WT CHO cell. In certain embodiments, the expression of a polypeptide in a cell that has been modified to knock down expression of the polypeptide is no more than about 90%, no more than about 80%, no more than about 70%, no more than about 60%, no more than about 50%, no more than about 40%, no more than about 30%, no more than about 20%, no more than about 10%, no more than about 5%, no more than about 4%, no more than about 3%, no more than about 2% or no more than about 1% of the corresponding polypeptide expression of a reference cell, e.g., a WT CHO cell.

In certain embodiments, the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a cell that has been modified to knock down expression of the polypeptide is between about 1% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 1% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 1% and about 70%, between about 10% and about 70%, between about 20% and about 70%, between about 30% and about 70%, between about 40% and about 70%, between about 50% and about 70%, between about 60% and about 70%, between about 65% and about 70%, between about 1% and about 60%, between about 10% and about 60%, between about 20% and about 60%, between about 30% and about 60%, between about 40% and about 60%, between about 50% and about 60%, between about 55% and about 60%, between about 1% and about 50%, between about 10% and about 50%, between about 20% and about 50%, between about 30% and about 50%, between about 40% and about 50%, between about 45% and about 50%, between about 1% and about 40%, between about 10% and about 40%, between about 20% and about 40%, between about 30% and about 40%, between about 40% and about 40%, between about 35% and about 40%, between about 1% and about 30%, between about 10% and about 30%, between about 20% and about 30%, between about 25% and about 30%, between about 1% and about 20%, between about 5% and about 20%, between about 10% and about 20%, between about 15% and about 20%, between about 1% and about 10%, between about 5% and about 10%, between about 5% and about 20%, between about 5% and about 30%, between about 5% and about 40% of the corresponding polypeptide expression of a reference cell, e.g., a WT CHO cell. In certain embodiments, the expression of a polypeptide in a cell that has been modified to knock down expression of the polypeptide is between about 1% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 1% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 1% and about 70%, between about 10% and about 70%, between about 20% and about 70%, between about 30% and about 70%, between about 40% and about 70%, between about 50% and about 70%, between about 60% and about 70%, between about 65% and about 70%, between about 1% and about 60%, between about 10% and about 60%, between about 20% and about 60%, between about 30% and about 60%, between about 40% and about 60%, between about 50% and about 60%, between about 55% and about 60%, between about 1% and about 50%, between about 10% and about 50%, between about 20% and about 50%, between about 30% and about 50%, between about 40% and about 50%, between about 45% and about 50%, between about 1% and about 40%, between about 10% and about 40%, between about 20% and about 40%, between about 30% and about 40%, between about 35% and about 40%, between about 1% and about 30%, between about 10% and about 30%, between about 20% and about 30%, between about 25% and about 30%, between about 1% and about 20%, between about 5% and about 20%, between about 10% and about 20%, between about 15% and about 20%, between about 1% and about 10%, between about 5% and about 10%, between about 5% and about 20%, between about 5% and about 30%, between about 5% and about 40% of the corresponding polypeptide expression of a reference cell, e.g., a WT CHO cell.

In certain embodiments, the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; HACH; CES1F/CES-B1L; LYPLA1; CES1; PLA1A; and/or SIAE polypeptide, in a cell that has been modified to knock down expression of the polypeptide is between about 5% and about 40% of the corresponding polypeptide expression of a reference cell, e.g., a WT CHO cell. In certain embodiments, the expression of a polypeptide in a cell that has been modified to knock down expression of the polypeptide is between about 5% and about 40% of the corresponding polypeptide expression of a reference cell, e.g., a WT CHO cell. The expression level of the polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in different reference cells (e.g., cells that comprise at least one or both wild-type alleles of the corresponding gene) can vary.

In certain embodiments, a genetic engineering system is employed to modulate (e.g., knock down or knock out) the expression of a particular polypeptide (e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE expression). Various genetic engineering systems known in the art can be used for the methods disclosed herein. Non-limiting examples of such systems include the CRISPR/Cas system, the zinc-finger nuclease (ZFN) system, the transcription activator-like effector nuclease (TALEN) system and the use of other tools for protein knockdown by gene silencing, such as small interfering RNAs (siRNAs), short hairpin RNA (shRNA), and microRNA (miRNA). Any CRISPR/Cas systems known in the art, including traditional, enhanced or modified Cas systems, as well as other bacterial based genome excising tools such as Cpf-1 can be used with the methods disclosed herein.

In certain embodiments, a portion of a gene, e.g., a gene coding for a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, is deleted to modulate, e.g., knock down or knock out, expression of the corresponding polypeptide. In certain embodiments, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or at least about 90% of the gene is deleted. In certain embodiments, no more than about 2%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, no more than about 85% or no more than about 90% of the gene is deleted. In certain embodiments, between about 2% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 2% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 2% and about 70%, between about 10% and about 70%, between about 20% and about 70%, between about 30% and about 70%, between about 40% and about 70%, between about 50% and about 70%, between about 60% and about 70%, between about 65% and about 70%, between about 2% and about 60%, between about 10% and about 60%, between about 20% and about 60%, between about 30% and about 60%, between about 40% and about 60%, between about 50% and about 60%, between about 55% and about 60%, between about 2% and about 50%, between about 10% and about 50%, between about 20% and about 50%, between about 30% and about 50%, between about 40% and about 50%, between about 45% and about 50%, between about 2% and about 40%, between about 10% and about 40%, between about 20% and about 40%, between about 30% and about 40%, between about 35% and about 40%, between about 2% and about 30%, between about 10% and about 30%, between about 20% and about 30%, between about 25% and about 30%, between about 2% and about 20%, between about 5% and about 20%, between about 10% and about 20%, between about 15% and about 20%, between about 2% and about 10%, between about 5% and about 10%, or between about 2% and about 5% of the gene is deleted.

In certain embodiments, at least one exon of a gene encoding a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide is at least partially deleted. "Partially deleted," as used herein, refers to at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, no more than about 2%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, no more than about 85%, no more than about 90%, no more than about 95%, between about 2% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 2% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 2% and about 70%, between about 10% and about 70%, between about 20% and about 70%, between about 30% and about 70%, between about 40% and about 70%, between about 50% and about 70%, between about 60% and about 70%, between about 65% and about 70%, between about 2% and about 60%, between about 10% and about 60%, between about 20% and about 60%, between about 30% and about 60%, between about 40% and about 60%, between about 50% and about 60%, between about 55% and about 60%, between about 2% and about 50%, between about 10% and about 50%, between about 20% and about 50%, between about 30% and about 50%, between about 40% and about 50%, between about 45% and about 50%, between about 2% and about 40%, between about 10% and about 40%, between about 20% and about 40%, between about 30% and about 40%, between about 35% and about 40%, between about 2% and about 30%, between about 10% and about 30%, between about 20% and about 30%, between about 25% and about 30%, between about 2% and about 20%, between about 5% and about 20%, between about 10% and about 20%, between about 15% and about 20%, between about 2% and about 10%, between about 5% and about 10%, or between about 2% and about 5% of a region, e.g., of the exon, is deleted.

In certain non-limiting embodiments, a CRISPR/Cas9 system is employed to modulate the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide. A clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), and trans-activating crRNA (tracrRNA, binds to crRNA and forms an active complex with Cas9). The terms "guide RNA" and "gRNA" refer to any nucleic acid that promotes the specific association (or "targeting") of an RNA-guided nuclease such as a Cas9 to a target sequence such as a genomic or episomal sequence in a cell. gRNAs can be unimolecular (comprising a single RNA molecule, and referred to alternatively as chimeric) or modular (comprising more than one, and typically two, separate RNA molecules, such as a crRNA and a tracrRNA, which are usually associated with one another, for instance by duplexing).

CRISPR/Cas9 strategies can employ a vector to transfect the mammalian cell. The guide RNA (gRNA) can be designed for each application as this is the sequence that Cas9 uses to identify and directly bind to the target DNA in a cell. Multiple crRNAs and the tracrRNA can be packaged together to form a single-guide RNA (sgRNA). The sgRNA can be joined together with the Cas9 gene and made into a vector in order to be transfected into cells.

In certain embodiments, the CRISPR/Cas9 system for use in modulating expression of one or more polypeptides, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, comprises a Cas9 molecule and one or more gRNAs comprising a targeting domain that is complementary to a target sequence of the gene encoding the polypeptide of interest. In certain embodiments, the target gene is a region of the gene coding for the polypeptide of interest, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide. The target sequence can be any exon or intron region within the gene.

In certain embodiments, the gRNAs are administered to the cell in a single vector and the Cas9 molecule is administered to the cell in a second vector. In certain embodiments, the gRNAs and the Cas9 molecule are administered to the cell in a single vector. Alternatively, each of the gRNAs and Cas9 molecule can be administered by separate vectors. In certain embodiments, the CRISPR/Cas9 system can be delivered to the cell as a ribonucleoprotein complex (RNP) that comprises a Cas9 protein complexed with one or more gRNAs, e.g., delivered by electroporation (see, e.g., DeWitt et al., Methods 121-122:9-15 (2017) for additional methods of delivering RNPs to a cell). In certain embodiments, administering the CRISPR/Cas9 system to the cell results in the knock out or knock down of the expression of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide.

In certain embodiments, the genetic engineering system is a ZFN system for modulating the expression of a particular polypeptide in a mammalian cell, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; HACH; CES1F/CES-B1L; LYPLA1; CES1; PLA1A; and/or SIAE polypeptide. The ZFN can act as restriction enzyme, which is generated by combining a zinc finger DNA-binding domain with a DNA-cleavage domain. A zinc finger domain can be engineered to target specific DNA sequences which allows the zinc-finger nuclease to target desired sequences within genomes. The DNA-binding domains of individual ZFNs typically contain a plurality of individual zinc finger repeats and can each recognize a plurality of base pairs. The most common method to generate a new zinc-finger domain is to combine smaller zinc-finger "modules" of known specificity. The most common cleavage domain in ZFNs is the non-specific cleavage domain from the type IIs restriction endonuclease FokI. ZFN modulates the expression of proteins by producing double-strand breaks (DSBs) in the target DNA sequence, which will, in the absence of a homologous template, be repaired by non-homologous end-joining (NHEJ). Such repair can result in deletion or insertion of base-pairs, producing frame-shift and preventing the production of the harmful protein (Durai et al., *Nucleic Acids Res.;* 33 (18): 5978-90 (2005)). Multiple pairs of ZFNs can also be used to completely remove entire large segments of genomic sequence (Lee et al., *Genome Res.;* 20 (1): 81-9 (2010)).

In certain embodiments, the genetic engineering system is a TALEN system for modulating the expression of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in a mammalian cell. TALENs are restriction enzymes that can be engineered to cut specific sequences of DNA. TALEN systems operate on a similar principle as ZFNs. TALENs are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome (Boch et al., Nature Biotechnology; 29(2):135-6 (2011)). In certain embodiments, the target gene encodes a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the expression of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, can be knocked down using oligonucleotides that have complementary sequences to corresponding nucleic acids (e.g., mRNA).

Non-limiting examples of such oligonucleotides include small interference RNA (siRNA), short hairpin RNA (shRNA), and micro RNA (miRNA). In certain embodiments, such oligonucleotides can be homologous to at least a portion of a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE nucleic acid sequence, wherein the homology of the portion relative to the corresponding nucleic acid sequence is at least about 75 or at least about 80 or at least about 85 or at least about 90 or at least about 95 or at least about 98 percent. In certain non-limiting embodiments, the complementary portion can constitute at least 10 nucleotides or at least 15 nucleotides or at least 20 nucleotides or at least 25 nucleotides or at least 30 nucleotides and the antisense nucleic acid, shRNA, mRNA or siRNA molecules can be up to 15 or up to 20 or up to 25 or up to 30 or up to 35 or up to 40 or up to 45 or up to 50 or up to 75 or up to 100 nucleotides in length. Antisense nucleic acid, shRNA, mRNA or siRNA molecules can comprise DNA or atypical or non-naturally occurring residues, for example, but not limited to, phosphorothioate residues.

The genetic engineering system disclosed herein can be delivered into the mammalian cell using a viral vector, e.g., retroviral vectors such as gamma-retroviral vectors, and lentiviral vectors. Combinations of retroviral vector and an appropriate packaging line are suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD 114 or GALV envelope and any other known in the art. Possible methods of transduction also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89:1817.

Other transducing viral vectors can be used to modify the mammalian cell disclosed herein. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for genetic engineering of the mammalian cell disclosed herein. For example, a nucleic acid molecule can be introduced into the mammalian cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation and protoplast fusion. Liposomes can also be potentially beneficial for delivery of nucleic acid molecules into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically.

5.3 Cells Comprising Gene-Specific Modifications

In one aspect, the present disclosure relates to cells or compositions comprising one or more cells, e.g., mammalian cells, having reduced or eliminated activity of one or more polypeptides, for example one or more enzymes, e.g., one more lipase, sterase, and/or hydrolase. In certain embodiments, the cell has reduced or eliminated activity of BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE. In certain embodiments, the cell has reduced or eliminated activity of PLBL2. In certain embodiments, the cell has reduced or eliminated activity of LPLA2; LPL; and LIPA. In certain embodiments, the cell has reduced or eliminated activity of LPLA2; LPL; LIPA; PPT1; PLBL2; PLD3; and SMPD1. In certain embodiments, the cell has reduced or eliminated activity of LPLA2; LPL; LIPA; PPT1; PLBL2; PLD3; SMPD1; PLAA; IAH1; OTUB1; LYPLA2; and PLA2G12A. In certain embodiments, the cell has reduced or eliminated activity of BAX; BAK; LPLA2; LPL; LIPA; PPT1; PLD3; and SMPD1. In certain embodiments, the cell has reduced or eliminated activity of BAX; BAK; LPLA2; LPL; LIPA; PPT1; PLBL2; PLD3; SMPD1; CLU; PRDX1; PLAA; and ACOT13. In certain embodiments, the cell has reduced or eliminated activity of LPLA2; LPL; and PPT1. In certain embodiments, the cell has reduced or eliminated activity of PPT1. In certain embodiments, the cell has reduced or eliminated activity of LPLA2; LPL; LIPA; and PPT1. In certain embodiments, the cell has reduced or eliminated activity of HACH; CES1F/CES-B1L; and LYPLA1. In certain embodiments, the cell has reduced or eliminated activity of LPLA2; LPL; LIPA; PPT1; HACH; CES1F/CES-B1L; and LYPLA1. In certain embodiments, the cell has reduced or eliminated activity of SMPD1; CES1; PLA1A; and SIAE. In certain embodiments, the cell has reduced or eliminated activity of LPLA2; LPL; LIPA; PPT1; HACH; CES1F/CES-B1L; LYPLA1; SMPD1; CES1; PLA1A; and SIAE. In certain embodiments, the cell has reduced or eliminated activity of LPLA2; LMF1; LIPA; PPT1; HACH; CES1F/CES-B1L; and LYPLA1. In certain embodiments, the cell has reduced or eliminated activity of LPLA2; LMF1; APOC2; LIPA; PPT1; HACH; CES1F/CES-B1L; and LYPLA1. In certain embodiments, the cell has reduced or eliminated activity of LMF1 and APOC2.

As used herein, eliminated activity refers to the elimination of the activity of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/ CES-B1L; LYPLA1; CES1; PLA1A; and/or SIAE polypeptide, in the cell as compared to a reference cell. As used herein, reduced activity refers to a reduction in the activity of a polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, in the cell as compared to a reference cell.

Non-limiting examples of cells useful in connection with the subject matter of the present disclosure include CHO cells (e.g., DHFR CHO cells), dp12.CHO cells, CHO-K1 (ATCC, CCL-61), monkey kidney CV1 line transformed by SV40 (e.g., COS-7 ATCC CRL-1651), human embryonic kidney line (e.g., 293 or 293 cells subcloned for growth in suspension culture), baby hamster kidney cells (e.g., BHK, ATCC CCL 10), mouse sertoli cells (e.g. TM4), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor (e.g., MNT 060562, ATCC CCL51), TRI cells, MRC 5 cells, FS4 cells, human hepatoma line (e.g., Hep G2), myeloma cell lines (e.g., Y0, NS0 and Sp2/0). In certain embodiments, the cells are CHO cells. Additional non-limiting examples of CHO host cells include CHO K1SV cells, CHO DG44 cells, a CHO DUKXB-11 cells, CHOK1S cells and CHO KIM cells.

In certain embodiments, the cells disclosed herein express a product of interest. In certain embodiments, the product of interest is a recombinant protein. In certain embodiments, the product of interest is a monoclonal antibody. Additional non-limiting examples of products of interest are provided in Section 5.5.

In certain embodiments, the cells disclosed herein can be used for production of commercially useful amounts of the product of interest. In certain embodiments, the cells disclosed herein facilitate the production of commercially useful amounts of a product of interest, at least in part, via inducing a reduced level of degradation of components of the production process, relative to a reference cells, e.g., WT CHO cells. In certain embodiments, the components of the production process are lipid-containing components. In certain embodiments, the lipid-containing components are detergents. In certain embodiments, the detergent is a polysorbate-containing component. In certain embodiments, the polysorbate-containing component is PS20 (polysorbate 20 or Tween 20). In certain embodiments, the polysorbate-containing component is PS80 (polysorbate 80 or Tween 80). In certain embodiments, cells of the present disclosure can reduce degradation of a component of the production process, e.g., PS20, to less than about 90%, less than about 80%, less than about 70%, less than about 60%, less than about 50%, less than about 40%, less than about 30%, less than about 20%, less than about 10%, less than about 5%, less than about 4%, less than about 3%, less than about 2% or less than about 1% of the corresponding PS20 degradation observed with a reference cell, e.g., a WT CHO cell.

In certain embodiments, the cells disclosed herein can comprise a nucleic acid that encodes a product of interest. In certain embodiments, the nucleic acid can be present in one or more vectors, e.g., expression vectors. One type of vector is a "plasmid," which refers to a circular double stranded DNA loop into which additional DNA segments can be ligated. Another type of vector is a viral vector, where additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). Additional non-limiting examples of expression vectors for use in the present disclosure include viral vectors (e.g., replication defective retroviruses, adenoviruses and adeno-associated viruses) that serve equivalent functions.

In certain embodiments, the nucleic acid encoding a product of interest can be introduced into a host cell, disclosed herein. In certain embodiments, the introduction of a nucleic acid into a cell can be carried out by any method known in the art including, but not limited to, transfection, electroporation, microinjection, infection with a viral or bacteriophage vector containing the nucleic acid sequences, cell fusion, chromosome-mediated gene transfer, microcell-mediated gene transfer, spheroplast fusion, etc. In certain embodiments, the host cell is eukaryotic, e.g., a Chinese Hamster Ovary (CHO) cell or lymphoid cell (e.g., Y0, NS0, Sp20 cell).

In certain embodiments, the nucleic acid encoding a product of interest can be randomly integrated into a host cell genome ("Random Integration" or "RI"). For example, but not by way of limitation, a nucleic acid encoding a product of interest can be randomly integrated into the genome of a cell that has been modulated to have reduced or eliminated activity of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/ CES-B1L; LYPLA1; CES1; PLA1A; and/or SIAE polypeptide.

In certain embodiments, the nucleic acid encoding a product of interest can be integrated into a host cell genome in a targeted manner ("Targeted Integration" or "TI"). For example, but not by way of limitation, a nucleic acid encoding a product of interest can be integrated into the genome of a cell that has been modulated to have reduced or eliminated activity of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN;

PLA2G7; USP5; ASAH1; LMF1; APOC2; HACH; CES1F/ CES-B1L; LYPLA1; CES1; PLA1A; and/or SIAE polypeptide, in a targeted manner. An "integration site" comprises a nucleic acid sequence within a host cell genome into which an exogenous nucleotide sequence is inserted. In certain embodiments, an integration site is between two adjacent nucleotides on the host cell genome. In certain embodiments, an integration site includes a stretch of nucleotide sequences. In certain embodiments, the integration site is located within a specific locus of the genome of the CHO host cell. In certain embodiments, the integration site is within an endogenous gene of the CHO host cell. Any integration site known in the art can be regulated and used with the subject matter disclosed herein. The targeted integration can be mediated by methods and systems known in the art. For example, but not by way of limitation, methods and systems disclosed in International Application No. PCT/US18/067070, filed Dec. 21, 2018, the content of which is incorporated herein by its entirely, can be used for targeted integration.

In certain embodiments, the nucleic acid encoding a product of interest can be integrated into a host cell genome using transposase-based integration. Transposase-based integration techniques are disclosed, for example, in Trubitsyna et al., Nucleic Acids Res. 45(10):e89 (2017), Li et al., PNAS 110(25):E2279-E2287 (2013) and WO 2004/009792, which are incorporated by reference herein in their entireties.

In certain embodiments, the nucleic acid encoding a product of interest can be randomly integrated into a host cell genome ("Random Integration" or "RI"). In certain embodiments, the random integration can be mediated by any method or systems known in the art. In certain embodiments, the random integration is mediated by MaxCyte STX® electroporation system.

In certain embodiments, targeted integration can be combined with random integration. In certain embodiments, the targeted integration can be followed by random integration. In certain embodiments, random integration can be followed by targeted integration. For example, but not by way of limitation, a nucleic acid encoding a product of interest can be randomly integrated into the genome of a cell that has been modulated to have reduced or eliminated activity of a particular polypeptide, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide, and a nucleic acid encoding the same product of interest can be integrated in the genome of the cell in a targeted manner.

In certain embodiments, the host cells disclosed herein comprise one or more altered enzyme genes. In certain embodiments, the alteration to the enzyme gene reduces or eliminates the activity of the enzyme. In certain embodiments, the host cells disclosed herein comprise one or more altered LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE genes. In certain embodiments, the subsequent transcript of an altered LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE gene codes for a protein having reduced or eliminated activity. In certain embodiments, the one or more altered enzyme genes are altered by disruption of a coding region. In certain embodiments, the genes alteration comprises a biallelic alteration. In certain embodiments, the enzyme genes alteration comprises a deletion of 1 or more base pairs, 2 or more base pairs, 3 or more base pairs, 4 or more base pairs, 5 or more base pairs, 6 or more base pairs, 7 or more base pairs, 8 or more base pairs, 9 or more base pairs, 10 or more base pairs, 11 or more base pairs, 12 or more base pairs, 13 or more base pairs, 14 or more base pairs, 15 or more base pairs, 16 or more base pairs, 17 or more base pairs, 18 or more base pairs, 19 or more base pairs, or 20 or more base pairs.

5.4. Cell Culturing Methods

In one aspect, the present disclosure provides a method for producing a product of interest comprising culturing a cell disclosed herein. Suitable culture conditions for mammalian cells known in the art can be used for culturing the cells herein (J. Immunol. Methods (1983) 56:221-234) or can be easily determined by the skilled artisan (see, for example, Animal Cell Culture: A Practical Approach 2nd Ed., Rickwood, D. and Hames, B. D., eds. Oxford University Press, New York (1992)).

Mammalian cell culture can be prepared in a medium suitable for the particular cell being cultured. Commercially available media such as Ham's F10 (Sigma), Minimal Essential Medium (MEM, Sigma), RPMI-1640 (Sigma) and Dulbecco's Modified Eagle's Medium (DMEM, Sigma) are exemplary nutrient solutions. In addition, any of the media described in Ham and Wallace, (1979) Meth. Enz., 58:44; Barnes and Sato, (1980) Anal. Biochem., 102:255; U.S. Pat. Nos. 4,767,704; 4,657,866; 4,927,762; 5,122,469 or U.S. Pat. No. 4,560,655; International Publication Nos. WO 90/03430; and WO 87/00195; the disclosures of all of which are incorporated herein by reference, can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin (gentamicin), trace elements (defined as inorganic compounds usually present at final concentrations in the micromolar range) lipids (such as linoleic or other fatty acids) and their suitable carriers, and glucose or an equivalent energy source. Any other necessary supplements can also be included at appropriate concentrations that would be known to those skilled in the art.

In certain embodiments, the mammalian cell that has been modified to reduce and/or eliminate the activity of a particular polypeptide is a CHO cell, e.g., a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE polypeptide. Any suitable medium can be used to culture the CHO cell. In certain embodiments, a suitable medium for culturing the CHO cell can contain a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346-349) (the formulation of medium as described in U.S. Pat. No. 5,122,469 are particularly appropriate) with modified concentrations of some components such as amino acids, salts, sugar, and vitamins, and optionally containing glycine, hypoxanthine, and thymidine; recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements.

In certain embodiments, the mammalian cell that has been modified to reduce and/or eliminate the activity of a particular polypeptide, e.g. a BAX; BAK; LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; HACH; CES1F/CES-B1L; LYPLA1; CES1; PLA1A; and/or SIAE polypeptide, is a cell that expresses a recombinant protein. The recombinant protein can be produced by growing cells which express the products of interest under a variety of cell culture conditions. For instance, cell culture procedures for the large or small-scale production of proteins are potentially useful within the context of the present disclosure. Procedures including, but not limited to, a fluidized bed bioreactor, hollow fiber bioreactor, roller bottle culture, shake flask culture, or stirred tank bioreactor system can be used, in the latter two systems, with or without microcarriers, and operated alternatively in a batch, fed-batch, or continuous mode.

In certain embodiments, the cell culture of the present disclosure is performed in a stirred tank bioreactor system and a fed batch culture procedure is employed. In the fed batch culture, the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel).

In certain embodiments, the cells of the culture can be propagated according to any scheme or routine that can be suitable for the specific host cell and the specific production plan contemplated. Therefore, the present disclosure contemplates a single step or multiple step culture procedure. In a single step culture, the host cells are inoculated into a culture environment and the processes of the instant disclosure are employed during a single production phase of the cell culture. Alternatively, a multi-stage culture is envisioned. In the multi-stage culture cells can be cultivated in a number of steps or phases. For instance, cells can be grown in a first step or growth phase culture wherein cells, possibly removed from storage, are inoculated into a medium suitable for promoting growth and high viability. The cells can be maintained in the growth phase for a suitable period of time by the addition of fresh medium to the host cell culture.

In certain embodiments, fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30° to 38° C. and a suitable $dO_2$ is between 5-90% of air saturation.

At a particular stage the cells can be used to inoculate a production phase or step of the cell culture. Alternatively, as described above the production phase or step can be continuous with the inoculation or growth phase or step.

In certain embodiments, the culturing methods described in the present disclosure can further include harvesting the product from the cell culture, e.g., from the production phase of the cell culture. In certain embodiments, the product produced by the cell culture methods of the present disclosure can be harvested from the third bioreactor, e.g., production bioreactor. For example, but not by way of limitation, the disclosed methods can include harvesting the product at the completion of the production phase of the cell culture. Alternatively or additionally, the product can be harvested prior to the completion of the production phase. In certain embodiments, the product can be harvested from the cell culture once a particular cell density has been achieved. For example, but not by way of limitation, the cell density can be from about $2.0 \times 10^7$ cells/mL to about $5.0 \times 10^7$ cells/mL prior to harvesting.

In certain embodiments, harvesting the product from the cell culture can include one or more of centrifugation, filtration, acoustic wave separation, flocculation and cell removal technologies.

In certain embodiments, the product of interest can be secreted from the host cells or can be a membrane-bound, cytosolic or nuclear protein. In certain embodiments, soluble forms of the polypeptide can be purified from the conditioned cell culture media and membrane-bound forms of the polypeptide can be purified by preparing a total membrane fraction from the expressing cells and extracting the membranes with a nonionic detergent such as TRITON® X-100 (EMD Biosciences, San Diego, Calif). In certain embodiments, cytosolic or nuclear proteins can be prepared by lysing the host cells (e.g., by mechanical force, sonication and/or detergent), removing the cell membrane fraction by centrifugation and retaining the supernatant.

5.5 Products

The cells and/or methods of the present disclosure can be used to produce any product of interest that can be expressed by the cells disclosed herein. In certain embodiments, the cells and/or methods of the present disclosure can be used for the production of polypeptides, e.g., mammalian polypeptides. In certain embodiments, the methods of the present disclosure can be used for the production of viral particles. In certain embodiments, the methods of the present disclosure can be used for the production of viral vectors. Non-limiting examples of such polypeptides include hormones, receptors, fusion proteins, regulatory factors, growth factors, complement system factors, enzymes, clotting factors, anti-clotting factors, kinases, cytokines, CD proteins, interleukins, therapeutic proteins, diagnostic proteins and antibodies. The cells and/or methods of the present disclosure are not specific to the molecule, e.g., antibody, that is being produced.

In certain embodiments, the methods of the present disclosure can be used for the production of antibodies, including therapeutic and diagnostic antibodies or antigen-binding fragments thereof. In certain embodiments, the antibody produced by cell and methods of the present disclosure can be, but are not limited to, monospecific antibodies (e.g., antibodies consisting of a single heavy chain sequence and a single light chain sequence, including multimers of such pairings), multispecific antibodies and antigen-binding fragments thereof. For example, but not by way of limitation, the multispecific antibody can be a bispecific antibody, a biepitopic antibody, a T-cell-dependent bispecific antibody (TDB), a Dual Acting FAb (DAF) or antigen-binding fragments thereof.

5.5.1 Multispecific Antibodies

In certain aspects, an antibody produced by cells and methods provided herein is a multispecific antibody, e.g., a bispecific antibody. "Multispecific antibodies" are monoclonal antibodies that have binding specificities for at least two different sites, i.e., different epitopes on different antigens (i.e., bispecific) or different epitopes on the same antigen (i.e., biepitopic). In certain aspects, the multispecific antibody has three or more binding specificities. Multispecific antibodies can be prepared as full length antibodies or antibody fragments as described herein.

Techniques for making multispecific antibodies include, but are not limited to, recombinant co-expression of two immunoglobulin heavy chain-light chain pairs having different specificities (see Milstein and Cuello, Nature 305: 537 (1983)) and "knob-in-hole" engineering (see, e.g., U.S. Pat. No. 5,731,168, and Atwell et al., J. Mol. Biol. 270:26 (1997)). Multispecific antibodies can also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992) and WO 2011/034605); using the common light chain technology for circumventing the light chain mispairing problem (see, e.g., WO 98/50431); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991).

Engineered antibodies with three or more antigen binding sites, including for example, "Octopus antibodies", or DVD-Ig are also included herein (see, e.g., WO 2001/77342 and WO 2008/024715). Other non-limiting examples of multispecific antibodies with three or more antigen binding sites can be found in WO 2010/115589, WO 2010/112193, WO 2010/136172, WO 2010/145792 and WO 2013/026831. The bispecific antibody or antigen binding fragment thereof also includes a "Dual Acting FAb" or "DAF" (see, e.g., US 2008/0069820 and WO 2015/095539).

Multispecific antibodies can also be provided in an asymmetric form with a domain crossover in one or more binding arms of the same antigen specificity, i.e., by exchanging the VH/VL domains (see, e.g., WO 2009/080252 and WO 2015/150447), the CH1/CL domains (see, e.g., WO 2009/080253) or the complete Fab arms (see, e.g., WO 2009/080251, WO 2016/016299, also see Schaefer et al, PNAS, 108 (2011) 1187-1191, and Klein at al., MAbs 8 (2016) 1010-20). In certain embodiments, the multispecific antibody comprises a cross-Fab fragment. The term "cross-Fab fragment" or "xFab fragment" or "crossover Fab fragment" refers to a Fab fragment, wherein either the variable regions or the constant regions of the heavy and light chain are exchanged. A cross-Fab fragment comprises a polypeptide chain composed of the light chain variable region (VL) and the heavy chain constant region 1 (CH1), and a polypeptide chain composed of the heavy chain variable region (VH) and the light chain constant region (CL). Asymmetrical Fab arms can also be engineered by introducing charged or non-charged amino acid mutations into domain interfaces to direct correct Fab pairing. See, e.g., WO 2016/172485.

Various further molecular formats for multispecific antibodies are known in the art and are included herein (see, e.g., Spiess et al., Mol. Immunol. 67 (2015) 95-106).

In certain embodiments, particular type of multispecific antibodies, also included herein, are bispecific antibodies designed to simultaneously bind to a surface antigen on a target cell, e.g., a tumor cell, and to an activating, invariant component of the T cell receptor (TCR) complex, such as CD3, for retargeting of T cells to kill target cells.

Additional non-limiting examples of bispecific antibody formats that can be useful for this purpose include, but are not limited to, the so-called "BiTE" (bispecific T cell engager) molecules wherein two scFv molecules are fused by a flexible linker (see, e.g., WO 2004/106381, WO 2005/061547, WO 2007/042261, and WO 2008/119567, Nagorsen and Bauerle, Exp Cell Res 317, 1255-1260 (2011)); diabodies (Holliger et al., Prot. Eng. 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat. Rev. 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

5.5.2 Antibody Fragments

In certain aspects, an antibody produced by the cells and methods provided herein is an antibody fragment. For example, but not by way of limitation, the antibody fragment is a Fab, Fab', Fab'-SH or F(ab')$_2$ fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an F(ab')$_2$ fragment that has two antigen-binding sites (two Fab fragments) and a part of the Fc region. For discussion of Fab and F(ab')$_2$ fragments comprising salvage receptor binding epitope residues and having increased in vivo half-life, see U.S. Pat. No. 5,869,046.

In certain embodiments, the antibody fragment is a diabody, a triabody or a tetrabody. "Diabodies" are antibody fragments with two antigen-binding sites that can be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab fragment. A "single chain Fab fragment" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab fragments are stabilized via the natural disulfide bond between the CL domain and the CH1 domain. In addition, these single chain Fab fragments might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody.

5.5.3 Chimeric and Humanized Antibodies

In certain aspects, an antibody produced by the cells and methods provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain aspects, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In certain embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that can be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

5.5.4 Human Antibodies

In certain aspects, an antibody produced by the cells and methods provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals can be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

5.5.5 Target Molecules

Non-limiting examples of molecules that can be targeted by an antibody produced by the cells and methods disclosed herein include soluble serum proteins and their receptors and other membrane bound proteins (e.g., adhesins). In certain embodiments, an antibody produced by the cells and methods disclosed herein is capable of binding to one, two or more cytokines, cytokine-related proteins, and cytokine receptors selected from the group consisting of 8MPI, 8MP2, 8MP38 (GDFIO), 8MP4, 8MP6, 8MP8, CSFI (M-CSF), CSF2 (GM-CSF), CSF3 (G-CSF), EPO, FGF1 (αFGF), FGF2 (βFGF), FGF3 (int-2), FGF4 (HST), FGF5, FGF6 (HST-2), FGF7 (KGF), FGF9, FGF1 0, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFN81, IFNG, IFNWI, FEL1, FEL1 (EPSELON), FEL1 (ZETA), IL 1A, IL 1B, IL2, IL3, IL4, IL5, IL6, IL7, IL8, IL9, IL10, IL 11, IL 12A, IL 13, IL 13, IL 14, IL 15, IL 16, IL 17, IL 17B, IL 18, IL 19, IL20, IL22, IL23, IL24, IL25, IL26, IL27, IL28A, IL28B, IL29, IL30, PDGFA, PDGFB, TGFA, TGFB1, TGFB2, TGFBb3, LTA (TNF-β), LTB, TNF (TNF-α), TNFSF4 (OX40 ligand), TNFSF5 (CD40 ligand), TNFSF6 (FasL), TNFSF7 (CD27 ligand), TNFSF8 (CD30 ligand), TNFSF9 (4-1 BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL 11 RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.k In certain embodiments, an antibody produced by cells and methods disclosed herein is capable of binding to a chemokine, chemokine receptor, or a chemokine-related protein selected from the group consisting of CCLI (1-309), CCL2 (MCP-1/MCAF), CCL3 (MIP-Iα), CCL4 (MIP-Iβ), CCL5 (RANTES), CCL7 (MCP-3), CCL8 (mcp-2), CCL11 (eotaxin), CCL 13 (MCP-4), CCL 15 (MIP-Iδ), CCL 16 (HCC-4), CCL 17 (TARC), CCL 18 (PARC), CCL 19 (MDP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCLI (GROI), CXCL2 (GR02), CXCL3 (GR03), CXCL5 (ENA-78), CXCL6 (GCP-2), CXCL9 (MIG), CXCL 10 (IP 10), CXCL 11 (1-TAC), CXCL 12 (SDFI), CXCL 13, CXCL 14, CXCL 16, PF4 (CXCL4), PPBP (CXCL7), CX3CL 1 (SCYDI), SCYEI, XCLI (lymphotactin), XCL2 (SCM-Iβ), BLRI (MDR15), CCBP2 (D6/JAB61), CCRI (CKRI/HM145), CCR2 (mcp-IRB IRA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Rα), IL8RB (IL8Rβ), LTB4R (GPR16), TCP10, CKLFSF2, CKLFSF3, CKLFSF4, CKLFSF5, CKLFSF6, CKLFSF7, CKLFSF8, BDNF, C5, C5R1, CSF3, GRCC10 (C10), EPO, FY (DARC), GDF5, HDF1, HDF1α, DL8, PRL, RGS3, RGS13, SDF2, SLIT2, TLR2, TLR4, TREM1, TREM2, and VHL.

In certain embodiments, an antibody produced by methods disclosed herein (e.g., a multispecific antibody such as a bispecific antibody) is capable of binding to one or more target molecules selected from the following: 0772P (CA125, MUC16) (i.e., ovarian cancer antigen), ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AHIR2; amyloid beta; ANGPTL; ANGPT2; ANGPTL3; ANGPTL4; ANPEP; APC; APOC1; AR; ASLG659; ASPHD1 (aspartate beta-hydroxylase domain containing 1; LOC253982); AZGP1 (zinc-a-glycoprotein); B7.1; B7.2; BAD; BAFF-R (B cell-activating factor receptor, BLyS receptor 3, BR3; BAG1; BAI1; BCL2; BCL6; BDNF; BLNK; BLRI (MDR15); BMP1; BMP2; BMP3B (GDF10); BMP4; BMP6; BMP8; BMPR1A; BMPR1B (bone morphogenic protein receptor-type IB); BMPR2; BPAG1 (plectin); BRCA1; Brevican; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP1δ); CCL16 (HCC-4); CCL17 (TARC); CCL18 (PARC); CCL19 (MIP-3β); CCL2 (MCP-1); MCAF; CCL20 (MIP-3α); CCL21 (MTP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Iα); CCL4 (MDP-Iβ); CCL5(RANTES); CCL7 (MCP-3); CCL8 (mcp-2); CCNA1; CCNA2; CCND1; CCNE1; CCNE2; CCR1 (CKRI/HM145); CCR2 (mcp-IRP/RA); CCR3 (CKR/CMKBR3); CCR4; CCR5 (CMKBR5/ChemR13); CCR6 (CMKBR6/CKR-L3/STRL22/DRY6); CCR7 (CKBR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD22 (B-cell receptor CD22-B isoform); CD24; CD28; CD3; CD37; CD38; CD3E; CD3G; CD3Z; CD4; CD40; CD40L; CD44; CD45RB; CD52; CD69; CD72; CD74; CD79A (CD79a, immunoglobulin-associated alpha, a B cell-specific protein); CD79B; CDS; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21/WAF1/Cip1); CDKN1B (p27/Kip1); CDKN1C; CDKN2A (P16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLL-1 (CLEC12A, MICL, and DCAL2); CLN3; CLU (clusterin); CMKLR1; CMKOR1 (RDC1); CNR1; COL 18A1; COL1A1; COL4A3; COL6A1; complement factor D; CR2; CRP; CRIPTO (CR, CR1, CRGF, CRIPTO, TDGF1, teratocarcinoma-derived growth factor); CSFI (M-CSF); CSF2 (GM-CSF); CSF3 (GCSF); CTLA4; CTNNB1 (b-catenin); CTSB (cathepsin B); CX3CL1 (SCYDI); CX3CR1 (V28); CXCL1 (GRO1); CXCL10 (IP-10); CXCL 11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR5 (Burkitt's lymphoma receptor 1, a G protein-coupled receptor); CXCR6 (TYMSTR/STRL33/Bonzo); CYB5; CYC1; CYSLTR1; DAB2IP; DES; DKFZp451J0118; DNCLI; DPP4; E16 (LAT1, SLC7A5); E2F1; ECGF1; EDG1; EFNA1; EFNA3; EFNB2; EGF; EGFR; ELAC2; ENG; ENO1; ENO2; ENO3; EPHB4; EphB2R; EPO; ERBB2 (Her-2); EREG; ERK8; ESR1; ESR2; ETBR (Endothelin type B receptor); F3 (TF); FADD; FasL; FASN; FCER1A; FCER2; FCGR3A; FcRH1 (Fc receptor-like protein 1); FcRH2 (IFGP4, IRTA4, SPAP1A (SH2 domain containing phosphatase anchor protein 1a), SPAP1B, SPAP1C); FGF; FGF1 (αFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR; FGFR3; FIGF (VEGFD); FEL1 (EPSILON); FIL1 (ZETA); FLJ12584; FLJ25530; FLRTI (fibronectin); FLT1; FOS; FOSL1 (FRA-1); FY (DARC); GABRP (GABAa); GAGEB1; GAGEC1; GALNAC4S-6ST; GATA3; GDF5; GDNF-Ra1 (GDNF family receptor alpha 1; GFRA1; GDNFR; GDNFRA; RETL1; TRNR1; RETL1; GDNFR-alpha1; GFR-ALPHA-1); GEDA; GFI1; GGT1; GM-CSF; GNASI; GNRHI; GPR2 (CCR10); GPR19 (G protein-coupled receptor 19; Mm.4787); GPR31; GPR44; GPR54 (KISS1 receptor; KISSIR; GPR54; HOT7T175; AXOR12); GPR81 (FKSG80); GPR172A (G protein-coupled receptor 172A; GPCR41; FLJ11856; D15Ertd747e); GRCCIO (C10); GRP; GSN (Gelsolin); GSTP1; HAVCR2; HDAC4; HDAC5; HDAC7A; HDAC9; HGF; HIF1A; HOP1; histamine and histamine receptors; HLA-A; HLA-DOB (Beta subunit of MHC class II molecule (Ia antigen); HLA-DRA; HM74; HMOXI; HUMCYT2A; ICEBERG; ICOSL; 1D2; IFN-α; IFNA1; IFNA2; IFNA4; IFNA5; IFNA6; IFNA7; IFNB1; IFNgamma; DFNW1; IGBP1; IGF1; IGF1R; IGF2; IGFBP2; IGFBP3; IGFBP6; IL-1; IL10; IL10RA; IL10RB; IL11; IL1 IRA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; ILIF10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; ILIRN; IL2; IL20; IL20Ra; IL21R; IL22; IL-22c; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); influenza A; influenza B; EL7; EL7R; EL8; IL8RA; DL8RB; IL8RB; DL9; DL9R; DLK; INHA; INHBA; INSL3; INSL4; IRAK1; IRTA2 (Immunoglobulin superfamily receptor translocation associated 2); ERAK2; ITGA1; ITGA2; ITGA3; ITGA6 (a6 integrin); ITGAV; ITGB3; ITGB4 (b4 integrin); a407 and aEP7 integrin heterodimers; JAG1; JAK1; JAK3; JUN; K6HF; KAI1; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); LGR5 (leucine-rich repeat-containing G protein-coupled receptor 5; GPR49, GPR67); Lingo-p75; Lingo-Troy; LPS; LTA (TNF-b); LTB; LTB4R (GPR16); LTB4R2; LTBR; LY64 (Lymphocyte antigen 64 (RP105), type I membrane protein of the leucine rich repeat (LRR) family); Ly6E (lymphocyte antigen 6 complex, locus E; Ly67, RIG-E, SCA-2, TSA-1); Ly6G6D (lymphocyte antigen 6 complex, locus G6D; Ly6-D, MEGT1); LY6K (lymphocyte antigen 6 complex, locus K; LY6K; HSJ001348; FLJ35226); MACMARCKS; MAG or OMgp; MAP2K7 (c-Jun); MDK; MDP; MIB1; midkine; MEF; MIP-2; MKI67; (Ki-67); MMP2; MMP9; MPF (MPF, MSLN, SMR, megakaryocyte potentiating factor, mesothelin); MS4A1; MSG783 (RNF124, hypothetical protein FLJ20315); MSMB; MT3 (metallothionectin-111); MTSS1; MUC1 (mucin); MYC; MY088; Napi3b (also known as NaPi2b) (NAPI-3B, NPTIIb, SLC34A2, solute carrier family 34 (sodium phosphate), member 2, type II sodium-dependent phosphate transporter 3b); NCA; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NR0B1; NR0B2; NR1D1; NR1D2; NR1H2; NR1H3; NR1H4; NR112; NR113; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZI; OPRD1; OX40; P2RX7; P2X5 (Purinergic receptor P2X ligand-gated ion channel 5); PAP; PART1; PATE; PAWR; PCA3; PCNA; PD-L1; PD-L2; PD-1; POGFA; POGFB; PECAM1; PF4 (CXCL4); PGF; PGR; phosphacan; PIAS2; PIK3CG; PLAU (uPA); PLG; PLXDC1; PMEL17 (silver homolog; SILV; D12S53E; PMEL17; SI; SIL); PPBP (CXCL7); PPID; PRI; PRKCQ; PRKDI; PRL; PROC; PROK2; PSAP; PSCA hlg (2700050C12Rik, C530008016Rik, RIKEN cDNA 2700050C12, RIKEN cDNA 2700050C12 gene); PTAFR; PTEN; PTGS2 (COX-2); PTN; RAC2 (p21 Rac2); RARB; RET (ret proto-oncogene; MEN2A; HSCR1; MEN2B; MTC1; PTC; CDHF12; Hs.168114; RET51; RET-ELE1); RGSI; RGS13; RGS3; RNF110 (ZNF144); ROBO2; S100A2; SCGB1D2 (lipophilin B); SCGB2A1 (mammaglobin2); SCGB2A2 (mammaglobin 1); SCYEI (endothelial Monocyte-activating cytokine); SDF2; Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B); SERPINA1; SERPINA3; SERPINB5 (maspin); SERPINE1 (PAI-1); SERPDMF1; SHBG; SLA2; SLC2A2; SLC33A1; SLC43A1; SLIT2; SPP1; SPRR1B (Spr1); ST6GAL1; STAB1; STAT6; STEAP (six transmembrane epithelial antigen of prostate); STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein); TB4R2; TBX21; TCPIO; TOGFI; TEK; TENB2 (putative transmembrane proteoglycan); TGFA; TGFBI; TGFBIII; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor; TLR1; TLR2; TLR3; TLR4; TLR5; TLR6; TLR7; TLR8; TLR9; TLR10; TMEFF1 (transmembrane protein with EGF-like and two follistatin-like domains 1; Tomoregulin-1); TMEM46 (shisa homolog 2); TNF; TNF-a; TNFAEP2 (B94); TNFAIP3;

TNFRSFIIA; TNFRSFIA; TNFRSFIB; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSFS (CD30 ligand); TNFSF9 (4-1 BB ligand); TOLLIP; Toll-like receptors; TOP2A (topoisomerase Ea); TP53; TPM1; TPM2; TRADD; TMEM118 (ring finger protein, transmembrane 2; RNFT2; FLJ14627); TRAF1; TRAF2; TRAF3; TRAF4; TRAF5; TRAF6; TREM1; TREM2; TrpM4 (BR22450, FLJ20041, TRPM4, TRPM4B, transient receptor potential cation channel, subfamily M, member 4); TRPC6; TSLP; TWEAK; Tyrosinase (TYR; OCAIA; OCAIA; tyrosinase; SHEP3); VEGF; VEGFB; VEGFC; versican; VHL C5; VLA-4; XCL1 (lymphotactin); XCL2 (SCM-1b); XCRI(GPR5/CCXCRI); YY1; and ZFPM2.

In certain embodiments, an antibody produced by the cells and methods disclosed herein is capable of binding to CD proteins such as CD3, CD4, CD5, CD16, CD19, CD20, CD21 (CR2 (Complement receptor 2) or C3DR (C3d/Epstein Barr virus receptor) or Hs.73792); CD33; CD34; CD64; CD72 (B-cell differentiation antigen CD72, Lyb-2); CD79b (CD79B, CD790, IGb (immunoglobulin-associated beta), B29); CD200 members of the ErbB receptor family such as the EGF receptor, HER2, HER3, or HER4 receptor; cell adhesion molecules such as LFA-1, Mac1, p150.95, VLA-4, ICAM-1, VCAM, alpha4/beta7 integrin, and alphav/beta3 integrin including either alpha or beta subunits thereof (e.g., anti-CD11a, anti-CD18, or anti-CD11b antibodies); growth factors such as VEGF-A, VEGF-C; tissue factor (TF); alpha interferon (alphaIFN); TNFalpha, an interleukin, such as IL-1 beta, IL-3, IL-4, IL-5, IL-6, IL-8, IL-9, IL-13, IL 17 AF, IL-1S, IL-13R alpha1, IL13R alpha2, IL-4R, IL-5R, IL-9R, IgE; blood group antigens; flk2/flt3 receptor; obesity (OB) receptor; mpl receptor; CTLA-4; RANKL, RANK, RSV F protein, protein C etc.

In certain embodiments, the cells and methods provided herein can be used to produce an antibody (or a multispecific antibody, such as a bispecific antibody) that specifically binds to complement protein C5 (e.g., an anti-C5 agonist antibody that specifically binds to human C5). In certain embodiments, the anti-C5 antibody comprises 1, 2, 3, 4, 5 or 6 CDRs selected from (a) a heavy chain variable region CDR1 comprising the amino acid sequence of SSYYMA (SEQ ID NO:1); (b) a heavy chain variable region CDR2 comprising the amino acid sequence of AIFTGSGAEYKAEWAKG (SEQ ID NO:26); (c) a heavy chain variable region CDR3 comprising the amino acid sequence of DAGYDYPTHAMHY (SEQ ID NO: 27); (d) a light chain variable region CDR1 comprising the amino acid sequence of RASQGISSSLA (SEQ ID NO: 28); (e) a light chain variable region CDR2 comprising the amino acid sequence of GASETES (SEQ ID NO: 29); and (f) a light chain variable region CDR3 comprising the amino acid sequence of QNTKVGSSYGNT (SEQ ID NO: 30). For example, in certain embodiments, the anti-C5 antibody comprises a heavy chain variable domain (VH) sequence comprising one, two or three CDRs selected from: (a) a heavy chain variable region CDR1 comprising the amino acid sequence of (SSYYMA (SEQ ID NO: 1); (b) a heavy chain variable region CDR2 comprising the amino acid sequence of AIFTGSGAEYKAEWAKG (SEQ ID NO: 26); (c) a heavy chain variable region CDR3 comprising the amino acid sequence of DAGYDYPTHAMHY (SEQ ID NO: 27); and/or a light chain variable domain (VL) sequence comprising one, two or three CDRs selected from (d) a light chain variable region CDR1 comprising the amino acid sequence of RASQGISSSLA (SEQ ID NO: 28); (e) a light chain variable region CDR2 comprising the amino acid sequence of GASETES (SEQ ID NO: 29); and (f) a light chain variable region CDR3 comprising the amino acid sequence of QNTKVGSSYGNT (SEQ ID NO: 30). The sequences of CDR1, CDR2 and CDR3 of the heavy chain variable region and CDR1, CDR2 and CDR3 of the light chain variable region above are disclosed in US 2016/0176954 as SEQ ID NO: 117, SEQ ID NO: 118, SEQ ID NO: 121, SEQ ID NO: 122, SEQ ID NO: 123, and SEQ ID NO: 125, respectively. (See Tables 7 and 8 in US 2016/0176954.)

In certain embodiments, the anti-C5 antibody comprises the VH and VL sequences

```
                                               (SEQ ID NO: 31)
QVQLVESGGG LVQPGRSLRL SCAASGFTVH SSYYMAWVRQ

APGKGLEWVG AIFTGSGAEY KAEWAKGRVT ISKDTSKNQV

VLTMTNMDPV DTATYYCASD AGYDYPTHAM HYWGQGTLVT

VSS
and
                                               (SEQ ID NO: 32)
DIQMTQSPSS LSASVGDRVT ITCRASQGIS SSLAWYQQKP

GKAPKLLIYG ASETESGVPS RFSGSGSGTD FTLTISSLQP

EDFATYYCQN TKVGSSYGNT FGGGTK VEIK,
``` respectively, including post-translational modifications of those sequences. The VH and VL sequences above are disclosed in US 2016/0176954 as SEQ ID NO: 106 and SEQ ID NO: 111, respectively. (See Tables 7 and 8 in US 2016/0176954.) In certain embodiments, the anti-C5 antibody is 305L015 (see US 2016/0176954).

In certain embodiments, an antibody produced by methods disclosed herein is capable of binding to OX40 (e.g., an anti-OX40 agonist antibody that specifically binds to human OX40). In certain embodiments, the anti-OX40 antibody comprises 1, 2, 3, 4, 5 or 6 CDRs selected from (a) a heavy chain variable region CDR1 comprising the amino acid sequence of DSYMS (SEQ ID NO: 2); (b) a heavy chain variable region CDR2 comprising the amino acid sequence of DMYPDNGDSSYNQKFRE (SEQ ID NO: 3); (c) a heavy chain variable region CDR3 comprising the amino acid sequence of APRWYFSV (SEQ ID NO: 4); (d) a light chain variable region CDR1 comprising the amino acid sequence of RASQDISNYLN (SEQ ID NO: 5); (e) a light chain variable region CDR2 comprising the amino acid sequence of YTSRLRS (SEQ ID NO: 6); and (f) a light chain variable region CDR3 comprising the amino acid sequence of QQGHTLPPT (SEQ ID NO: 7). For example, in certain embodiments, the anti-OX40 antibody comprises a heavy chain variable domain (VH) sequence comprising one, two or three CDRs selected from: (a) a heavy chain variable region CDR1 comprising the amino acid sequence of DSYMS (SEQ ID NO: 2); (b) a heavy chain variable region CDR2 comprising the amino acid sequence of DMYPDNGDSSYNQKFRE (SEQ ID NO: 3); and (c) a heavy chain variable region CDR3 comprising the amino acid sequence of APRWYFSV (SEQ ID NO: 4) and/or a light chain variable domain (VL) sequence comprising one, two or three CDRs selected from (a) a light chain variable region CDR1 comprising the amino acid sequence of RASQDISNYLN (SEQ ID NO: 5); (b) a light chain variable region CDR2 comprising the amino acid sequence of YTSRLRS (SEQ ID NO: 6); and (c) a light chain variable region CDR3 comprising the amino acid sequence of QQGHTLPPT (SEQ ID NO: 7). In certain embodiments, the anti-OX40 antibody comprises the VH and VL sequences

```
                                          (SEQ ID NO: 8)
EVQLVQSGAE VKKPGASVKV SCKASGYTFT DSYMSWVRQA

PGQGLEWIGD MYPDNGDSSY NQKFRERVTI TRDTSTSTAY

LELSSLRSED TAVYYCVLAP RWYFSVWGQG TLVTVSS
and
                                          (SEQ ID NO: 9)
DIQMTQSPSS LSASVGDRVT ITCRASQDIS NYLNWYQQKP

GKAPKLLIYY TSRLRSGVPS RFSGSGSGTD FTLTISSLQP

EDFATYYCQQ GHTLPPTFGQ GTKVEIK,
``` respectively, including post-translational modifications of those sequences.

In certain embodiments, the anti-OX40 antibody comprises 1, 2, 3, 4, 5 or 6 CDRs selected from (a) a heavy chain variable region CDR1 comprising the amino acid sequence of NYLIE (SEQ ID NO: 10); (b) a heavy chain variable region CDR2 comprising the amino acid sequence of VINPGSGDTYYSEKFKG (SEQ ID NO: 11); (c) a heavy chain variable region CDR3 comprising the amino acid sequence of DRLDY (SEQ ID NO: 12); (d) a light chain variable region CDR1 comprising the amino acid sequence of HASQDISSYIV (SEQ ID NO: 13); (e) a light chain variable region CDR2 comprising the amino acid sequence of HGTNLED (SEQ ID NO: 14); and (f) a light chain variable region CDR3 comprising the amino acid sequence of VHYAQFPYT (SEQ ID NO: 15). For example, in certain embodiments, the anti-OX40 antibody comprises a heavy chain variable domain (VH) sequence comprising one, two or three CDRs selected from: (a) a heavy chain variable region CDR1 comprising the amino acid sequence of NYLIE (SEQ ID NO: 10); (b) a heavy chain variable region CDR2 comprising the amino acid sequence of VINPGSGDTYYSEKFKG (SEQ ID NO: 11); and (c) a heavy chain variable region CDR3 comprising the amino acid sequence of DRLDY (SEQ ID NO: 12) and/or a light chain variable domain (VL) sequence comprising one, two or three CDRs selected from (a) a light chain variable region CDR1 comprising the amino acid sequence of HASQDISSYIV (SEQ ID NO: 13); (b) a light chain variable region CDR2 comprising the amino acid sequence of HGTNLED (SEQ ID NO: 14); and (c) a light chain variable region CDR3 comprising the amino acid sequence of VHYAQFPYT (SEQ ID NO: 15). In certain embodiments, the anti-OX40 antibody comprises the VH and VL sequences

```
                                         (SEQ ID NO: 16)
EVQLVQSGAE VKKPGASVKV SCKASGYAFT NYLIEWVRQA

PGQGLEWIGV INPGSGDTYY SEKFKGRVTI TRDTSTSTAY

LELSSLRSED TAVYYCARDR LDYWGQGTLV TVSS
and
                                         (SEQ ID NO: 17)
DIQMTQSPSS LSASVGDRVT ITCHASQDIS SYIVWYQQKP

GKAPKLLIYH GTNLEDGVPS RFSGSGSGTD FTLTISSLQP

EDFATYYCVH YAQFPYTFGQ GTKVEIK,
``` respectively, including post-translational modifications of those sequences.

Further details regarding anti-OX40 antibodies are provided in WO 2015/153513, which is incorporated herein by reference in its entirety.

In certain embodiments, an antibody produced by the cells and methods disclosed herein is capable of binding to influenza virus B hemagglutinin, i.e., "fluB" (e.g., an antibody that binds hemagglutinin from the Yamagata lineage of influenza B viruses, binds hemagglutinin from the Victoria lineage of influenza B viruses, binds hemagglutinin from ancestral lineages of influenza B virus, or binds hemagglutinin from the Yamagata lineage, the Victoria lineage, and ancestral lineages of influenza B virus, in vitro and/or in vivo). Further details regarding anti-FluB antibodies are described in WO 2015/148806, which is incorporated herein by reference in its entirety.

In certain embodiments, an antibody produced by the cells and methods disclosed herein is capable of binding to low density lipoprotein receptor-related protein (LRP)-1 or LRP-8 or transferrin receptor, and at least one target selected from the group consisting of beta-secretase (BACE1 or BACE2), alpha-secretase, gamma-secretase, tau-secretase, amyloid precursor protein (APP), death receptor 6 (DR6), amyloid beta peptide, alpha-synuclein, Parkin, Huntingtin, p75 NTR, CD40 and caspase-6.

In certain embodiments, an antibody produced by the cells and methods disclosed herein is a human IgG2 antibody against CD40. In certain embodiments, the anti-CD40 antibody is RG7876.

In certain embodiments, the cells and methods of the present disclosure can be used to product a polypeptide. For example, but not by way of limitation, the polypeptide is a targeted immunocytokine. In certain embodiments, the targeted immunocytokine is a CEA-IL2v immunocytokine. In certain embodiments, the CEA-IL2v immunocytokine is RG7813. In certain embodiments, the targeted immunocytokine is a FAP-IL2v immunocytokine. In certain embodiments, the FAP-IL2v immunocytokine is RG7461.

In certain embodiments, the multispecific antibody (such as a bispecific antibody) produced by the cells or methods provided herein is capable of binding to CEA and at least one additional target molecule. In certain embodiments, the multispecific antibody (such as a bispecific antibody) produced according to methods provided herein is capable of binding to a tumor targeted cytokine and at least one additional target molecule. In certain embodiments, the multispecific antibody (such as a bispecific antibody) produced according to methods provided herein is fused to IL2v (i.e., an interleukin 2 variant) and binds an IL1-based immunocytokine and at least one additional target molecule. In certain embodiments, the multispecific antibody (such as a bispecific antibody) produced according to methods provided herein is a T-cell bispecific antibody (i.e., a bispecific T-cell engager or BiTE).

In certain embodiments, the multispecific antibody (such as a bispecific antibody) produced according to methods provided herein is capable of binding to at least two target molecules selected from: IL-1 alpha and IL-1 beta, IL-12 and IL-1S; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-~; IL-13 and LHR agonist; IL-12 and TWEAK, IL-13 and CL25; IL-13 and SPRR2a; IL-13 and SPRR2b; IL-13 and ADAMS, IL-13 and PED2, IL17A and IL17F, CEA and CD3, CD3 and CD19, CD138 and CD20; CD138 and CD40; CD19 and CD20; CD20 and CD3; CD3S and CD13S; CD3S and CD20; CD3S and CD40; CD40 and CD20; CD-S and TL-6; CD20 and BR3, TNF alpha and TGF-beta, TNF alpha and IL-1 beta; TNF alpha and IL-2, TNF alpha and TL-3, TNF alpha and TL-4, TNF alpha and TL-5, TNF alpha and TL6, TNF alpha and IL8, TNF alpha and TL-9, TNF alpha and IL-10, TNF alpha and IL-11, TNF alpha and IL-12, TNF alpha and IL-13, TNF alpha and IL-14, TNF alpha and IL-15, TNF alpha and IL-16, TNF alpha and IL-17, TNF alpha and IL-18, TNF alpha and IL-19, TNF alpha and IL-20, TNF alpha and IL-23, TNF alpha and IFN alpha, TNF alpha and CD4, TNF alpha and VEGF, TNF alpha and MIF, TNF alpha and ICAM-1, TNF alpha and PGE4, TNF alpha and PEG2, TNF alpha and RANK ligand, TNF alpha and Te38, TNF alpha and BAFF, TNF alpha and CD22, TNF alpha and CTLA-4, TNF alpha and GP130, TNF a and IL-12p40, VEGF and Angiopoietin, VEGF and HER2, VEGF-A and HER2, VEGF-A and PDGF, HER1 and HER2, VEGFA and ANG2, VEGF-A and VEGF-C, VEGF-C and VEGF-D, HER2 and DR5, VEGF and IL-8, VEGF and MET, VEGFR and MET receptor, EGFR and MET, VEGFR and EGFR, HER2 and CD64, HER2 and CD3, HER2 and CD16, HER2 and HER3; EGFR (HER1) and HER2, EGFR and HER3, EGFR and HER4, IL-14 and IL-13, IL-13 and CD40L, IL4 and CD40L, TNFR1 and IL-1 R, TNFR1 and IL-6R and TNFR1 and IL-18R, EpCAM and CD3, MAPG and CD28, EGFR and CD64, CSPGs and RGM A; CTLA-4 and BTN02; IGF1 and IGF2; IGF1/2 and Erb2B; MAG and RGM A; NgR and RGM A; NogoA and RGM A; OMGp and RGM A; POL-1 and CTLA-4; and RGM A and RGM B.

In certain embodiments, the multispecific antibody (such as a bispecific antibody) produced according to methods provided herein is an anti-CEA/anti-CD3 bispecific antibody. In certain embodiments, the anti-CEA/anti-CD3 bispecific antibody is RG7802. In certain embodiments, the anti-CEA/anti-CD3 bispecific antibody comprises the amino acid sequences set forth in SEQ ID NOs: 18-21 are provided below:

```
                                                    (SEQ ID NO: 18)
DIQMTQSPSS LSASVGDRVT ITCKASAAVG TYVAWYQQKP GKAPKLLIYS ASYRKRGVPS

RFSGSGSGTD FTLTISSLQP EDFATYYCHQ YYTYPLFTFG QGTKLEIKRT VAAPSVFIFP

PSDEQLKSGT ASVVCLLNNE YPREAKVQWK VDNALQSGNS QESVTEQDSK DSTYSLSSTL

TLSKADYEKH KVYACEVTHQ GLSSPVTKSF NRGEC (SEQ ID NO: 19)
QAVVTQEPSL TVSPGGTVTL TCGSSTGAVT TSNYANWVQE KPGQAFRGLI GGTNKRAPGT

PARESGSLLG GKAALTLSGA QPEDEAEYYC ALWYSNLWVF GGGTKLTVLS SASTKGPSVE

PLAPSSKSTS GGTAALGCLV KDYFPEPVTV SWNSGALTSG VHTFPAVLQS SGLYSLSSVV

TVPSSSLGTQ TYICNVNHKP SNTKVDKKVE PKSC (SEQ ID NO: 20)
QVQLVQSGAE VKKPGASVKV SCKASGYTFT EFGMNWVRQA PGQGLEWMGW INTKTGEATY

VEEFKGRVTF TTDTSTSTAY MELRSLRSDD TAVYYCARWD FAYYVEAMDY WGQGTTVTVS

SASTKGPSVF PLAPSSKSTS GGTAALGCLV KDYFPEPVTV SWNSGALTSG VHTFPAVLQS

SGLYSLSSVV TVPSSSLGTQ TYICNVNHKP SNTKVDKKVE PKSCDGGGGS GGGGSEVQLL

ESGGGLVQPG GSLRLSCAAS GFTESTYAMN WVRQAPGKGL EWVSRIRSKY NNYATYYADS

VKGRFTISRD DSKNTLYLQM NSLRAEDTAV YYCVRHGNFG NSYVSWFAYW GQGTLVTVSS

ASVAAPSVFI FPPSDEQLKS GTASVVCLLN NFYPREAKVQ WKVDNALQSG NSQESVTEQD

SKDSTYSLSS TLTLSKADYE KHKVYACEVT HQGLSSPVTK SENRGECDKT HTCPPCPAPE

AAGGPSVELF PPKPKDTLMI SRTPEVTCVV VDVSHEDPEV KENWYVDGVE VHNAKTKPRE

EQYNSTYRVV SVLTVLHQDW LNGKEYKCKV SNKALGAPIE KTISKAKGQP REPQVYTLPP

CRDELTKNQV SLWCLVKGFY PSDIAVEWES NGQPENNYKT TPPVLDSDGS FFLYSKLTVD

KSRWQQGNVF SCSVMHEALH NHYTQKSLSL SPGK (SEQ ID NO: 21)
QVQLVQSGAE VKKPGASVKV SCKASGYTFT EFGMNWVRQA PGQGLEWMG WINTKTGEATY

VEEFKGRVTF TTDTSTSTAY MELRSLRSDD TAVYYCARWD FAYYVEAMD YWGQGTTVTVS

SASTKGPSVF PLAPSSKSTS GGTAALGCLV KDYFPEPVTV SWNSGALTS GVHTEPAVLQS

SGLYSLSSVV TVPSSSLGTQ TYICNVNHKP SNTKVDKKVE PKSCDKTHT CPPCPAPEAAG
```

```
GPSVELFPPK PKDTLMISRT PEVTCVVVDV SHEDPEVKEN WYVDGVEVH NAKTKPREEQY

NSTYRVVSVL TVLHQDWING KEYKCKVSNK ALGAPIEKTI SKAKGQPRE PQVCTLPPSRD

ELTKNQVSLS CAVKGFYPSD IAVEWESNGQ PENNYKTTPP VLDSDGSFF LVSKLTVDKSR

WQQGNVESCS VMHEALHNHY TQKSLSLSPG K
```

Further details regarding anti-CEA/anti-CD3 bispecific antibodies are provided in WO 2014/121712, which is incorporated herein by reference in its entirety.

In certain embodiments, a multispecific antibody (such as a bispecific antibody) produced by the cells and methods disclosed herein is an anti-VEGF/anti-angiopoietin bispecific antibody. In certain embodiments, the anti-VEGF/anti-angiopoietin bispecific antibody bispecific antibody is a Crossmab. In certain embodiments, the anti-VEGF/anti-angiopoietin bispecific antibody is RG7716. In certain embodiments, the anti-CEA/anti-CD3 bispecific antibody comprises the amino acid sequences set forth in SEQ ID NOs: 22-25 are provided below:

```
                                              (SEQ ID NO: 22)
EVQLVESGGG LVQPGGSLRL SCAASGYDFT HYGMNWVRQA PGKGLEWVGW INTYTGEPTY

AADFKRRFTF SLDTSKSTAY LQMNSLRAED TAVYYCAKYP YYYGTSHWYF DVWGQGTLVT

VSSASTKGPS VFPLAPSSKS TSGGTAALGC LVKDYFPEPV TVSWNSGALT SGVHTFPAVL

QSSGLYSLSS VVTVPSSSLG TQTYICNVNH KPSNTKVDKK VEPKSCDKTH TCPPCPAPEA

AGGPSVFLFP PKPKDTLMAS RTPEVTCVVV DVSHEDPEVK FNWYVDGVEV HNAKTKPREE

QYNSTYRVVS VLTVLAQDWL NGKEYKCKVS NKALGAPIEK TISKAKGQPR EPQVYTLPPC

RDELTKNQVS LWCLVKGFYP SDIAVEWESN GQPENNYKTT PPVLDSDGSF FLYSKLTVDK

SRWQQGNVFS CSVMHEALHN AYTQKSLSLS PGK (SEQ ID NO: 23)
QVQLVQSGAE VKKPGASVKV SCKASGYTFT GYYMHWVRQA PGQGLEWMGW INPNSGGTNY

AQKFQGRVTM TRDTSISTAY MELSRLRSDD TAVYYCARSP NPYYYDSSGY YYPGAFDIWG

QGTMVTVSSA SVAAPSVFIF PPSDEQLKSG TASVVCLLNN FYPREAKVQW KVDNALQSGN

SQESVTEQDS KDSTYSLSST LTLSKADYEK HKVYACEVTH QGLSSPVTKS ENRGECDKTH

TCPPCPAPEA AGGPSVELFP PKPKDTLMAS RTPEVTCVVV DVSHEDPEVK FNWYVDGVEV

HNAKTKPREE QYNSTYRVVS VLTVLAQDWL NGKEYKCKVS NKALGAPIEK TISKAKGQPR

EPQVCTLPPS RDELTKNQVS LSCAVKGFYP SDIAVEWESN GQPENNYKTT PPVLDSDGSF

FLVSKLTVDK SRWQQGNVES CSVMHEALHN AYTQKSLSLS PGK (SEQ ID NO: 24)
DIQLTQSPSS LSASVGDRVT ITCSASQDIS NYLNWYQQKP GKAPKVLIYF TSSLHSGVPS

RFSGSGSGTD FTLTISSLQP EDFATYYCQQ YSTVPWTFGQ GTKVEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSEN RGEC (SEQ ID NO: 25)
SYVLTQPPSV SVAPGQTARI TCGGNNIGSK SVHWYQQKPG QAPVLVVYDD SDRPSGIPER

FSGSNSGNTA TLTISRVEAG DEADYYCQVW DSSSDHWVFG GGTKLTVLSS ASTKGPSVEP

LAPSSKSTSG GTAALGCLVK DYFPEPVTVS WNSGALTSGV HTFPAVLQSS GLYSLSSVVT

VPSSSLGTQT YICNVNHKPS NTKVDKKVEP KSC
```

In certain embodiments, the multispecific antibody (such as a bispecific antibody) produced by methods disclosed herein is an anti-Ang2/anti-VEGF bispecific antibody. In certain embodiments, the anti-Ang2/anti-VEGF bispecific antibody is RG7221. In certain embodiments, the anti-Ang2/anti-VEGF bispecific antibody is CAS Number 1448221-05-3.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or can be cells which have been transformed by recombinant techniques to express the transmembrane molecule. Other antigens and forms thereof useful for preparing antibodies will be apparent to those in the art.

In certain embodiments, the polypeptide (e.g., antibodies) produced by the cells and methods disclosed herein is capable of binding to can be further conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). An immunoconjugate comprising an antibody or bispecific antibody produced using the methods described herein can contain the cytotoxic agent conjugated to a constant region of only one of the heavy chains or only one of the light chains.

5.5.6 Antibody Variants

In certain aspects, amino acid sequence variants of the antibodies provided herein are contemplated, e.g., the antibodies provided in Section 5.5.5. For example, it can be desirable to alter the binding affinity and/or other biological properties of the antibody. Amino acid sequence variants of an antibody can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

5.5.6.1 Substitution, Insertion, and Deletion Variants

In certain aspects, antibody variants having one or more amino acid substitutions are provided. Sites of interest for substitutional mutagenesis include the CDRs and FRs. Conservative substitutions are shown in Table 1 under the heading of "preferred substitutions". More substantial changes are provided in Table 1 under the heading of "exemplary substitutions", and as further described below in reference to amino acid side chain classes. Amino acid substitutions can be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |

TABLE 1-continued

| Original Residue | Exemplary Substitutions | Preferred Substitutions |
| --- | --- | --- |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids can be grouped according to common side-chain properties:
   (1) hydrophobic: Norleucine, Met, Ala, Val, Leu, Ile;
   (2) neutral hydrophilic: Cys, Ser, Thr, Asn, Gln;
   (3) acidic: Asp, Glu;
   (4) basic: His, Lys, Arg;
   (5) residues that influence chain orientation: Gly, Pro;
   (6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which can be conveniently generated, e.g., using phage display-based affinity maturation techniques such as those described herein. Briefly, one or more. CDR residues are mutated and the variant antibodies displayed on phage and screened for a particular biological activity (e.g., binding affinity).

Alterations (e.g., substitutions) can be made in CDRs, e.g., to improve antibody affinity. Such alterations can be made in CDR "hotspots", i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some aspects of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding can be specifically identified, e.g., using alanine scanning mutagenesis or modeling. CDR-H3 and CDR-L3 in particular are often targeted.

In certain aspects, substitutions, insertions, or deletions can occur within one or more CDRs so long as such alterations do not substantially reduce the ability of the antibody to bind antigen. For example, conservative alterations (e.g., conservative substitutions as provided herein) that do not substantially reduce binding affinity can be made in the CDRs. Such alterations can, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that can be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions can be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues can be targeted or eliminated as candidates for substitution. Variants can be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

5.5.6.2 Glycosylation Variants

In certain aspects, an antibody provided herein is altered to increase or decrease the extent to which the antibody is glycosylated. Addition or deletion of glycosylation sites to an antibody can be conveniently accomplished by altering the amino acid sequence such that one or more glycosylation sites is created or removed.

Where the antibody comprises an Fc region, the oligosaccharide attached thereto can be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide can include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the disclosure can be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides can be at least about 20%, at least about 40%, at least about 60%, at least about 80%, or even about 100% (i.e., no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 can also be located about ±3 amino acids upstream or downstream of position 297, i.e., between positions 294 and 300, due to minor sequence variations in antibodies. Such antibodies having an increased proportion of non-fucosylated oligosaccharides in the Fc region can have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.,* 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants can have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants can have improved CDC function. Such antibody variants are described, e.g., in WO 1997/30087; WO 1998/58964; and WO 1999/22764.

5.5.6.3 Fc Region Variants

In certain aspects, one or more amino acid modifications can be introduced into the Fc region of an antibody provided herein, thereby generating an Fc region variant. The Fc region variant can comprise a human Fc region sequence (e.g., a human $IgG_1$, $IgG_2$, $IgG_3$ or $IgG_4$ Fc region) comprising an amino acid modification (e.g., a substitution) at one or more amino acid positions.

In certain aspects, the present disclosure contemplates an antibody variant that possesses some but not all effector functions, which make it a desirable candidate for applications in which the half life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods can be employed (see, for example, ACTI™ non-radioactive cytotoxicity assay for flow cytometry (CellTechnology, Inc. Mountain View, CA; and CytoTox 96© non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. Proc. Nat'l Acad. Sci. USA 95:652-656 (1998). C1q binding assays can also be carried out to confirm that the antibody is unable to bind C1q and hence lacks CDC activity. See, e.g., C1q and C3c binding ELISA in WO 2006/029879 and WO 2005/100402. To assess complement activation, a CDC assay can be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain aspects, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human IgG$_1$ Fc region. In one aspect, the substitutions are L234A, L235A and P329G (LALA-PG) in an Fc region derived from a human IgG$_1$ Fc region. (See, e.g., WO 2012/130831). In another aspect, the substitutions are L234A, L235A and D265A (LALA-DA) in an Fc region derived from a human IgG$_1$Fc region.

In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. J. Biol. Chem. 281 (2006) 23514-23524).

Fc region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU index numbering) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1994) 542). Residues I253, H310, and H435 were found to be critical for the interaction of human Fc with murine FcRn (Kim, J. K., et al., Eur. J. Immunol. 29 (1999) 2819). Studies of the human Fc-human FcRn complex have shown that residues I253, S254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In certain aspects, an antibody variant comprises an Fc region with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See, e.g., Grevys, A., et al., J. Immunol. 194 (2015) 5497-5508.

In certain aspects, an antibody variant comprises an Fc region with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human IgG1 Fc-region. (See, e.g., WO 2014/177460 A1).

In certain aspects, an antibody variant comprises an Fc region with one or more amino acid substitutions which increase FcRn binding, e.g., substitutions at positions 252, and/or 254, and/or 256 of the Fc region (EU numbering of residues). In certain aspects, the antibody variant comprises an Fc region with amino acid substitutions at positions 252, 254, and 256. In one aspect, the substitutions are M252Y, S254T and T256E in an Fc region derived from a human IgG$_1$ Fc-region. See also Duncan & Winter, *Nature* 322:738-40 (1988); U.S. Pat. Nos. 5,648,260; 5,624,821; and WO 94/29351 concerning other examples of Fc region variants.

The C-terminus of the heavy chain of the antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, an antibody comprising a heavy chain including a C-terminal CH3 domain as specified herein, comprises the C-terminal glycine-lysine dipeptide (G446 and K447, EU index numbering of amino acid positions). In one aspect of all aspects as reported herein, an antibody comprising a heavy chain including a C-terminal CH3 domain, as specified herein, comprises a C-terminal glycine residue (G446, EU index numbering of amino acid positions).

5.5.6.4 Cysteine Engineered Antibody Variants

In certain aspects, it can be desirable to create cysteine engineered antibodies, e.g., THIOMAB™ antibodies, in which one or more residues of an antibody are substituted with cysteine residues. In particular aspects, the substituted residues occur at accessible sites of the antibody. By substituting those residues with cysteine, reactive thiol groups are thereby positioned at accessible sites of the antibody and can be used to conjugate the antibody to other moieties, such as drug moieties or linker-drug moieties, to create an immunoconjugate, as described further herein. Cysteine engineered antibodies can be generated as described, e.g., in U.S. Pat. Nos. 7,521,541, 8,30,930, 7,855,275, 9,000,130, or WO 2016040856.

5.5.6.5 Antibody Derivatives

In certain aspects, an antibody provided herein can be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water. The polymer can be of any molecular weight, and can be branched or unbranched. The number of polymers attached to the antibody can vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

5.5.7 Immunoconjugates

The present disclosure also provides immunoconjugates comprising an antibody disclosed herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in Pharmacol Review 68:3-19 (2016).

In another aspect, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody as described herein conjugated to a radioactive atom to form a radioconjugate. A variety of radioactive isotopes are available for the production of radioconjugates. Examples include At$^{211}$, I$^{131}$, I$^{125}$, Y$^{90}$, Re$^{186}$, Re$^{188}$, Sm$^{153}$, Bi$^{212}$, P3$^2$, Pb$^{212}$ and radioactive isotopes of Lu. When the radioconjugate is used for detection, it can comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent can be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker can be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) can be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vi-

5.5.6 Viral Particles

In certain embodiments, the methods of the present disclosure can be used for the production of viral particles. In certain embodiments, the methods of the present disclosure can be used for the production of viral vectors. In certain embodiments, the methods of the present disclosure can be used for the expression of polypeptides, e.g., virus polypeptides. Non-limiting examples of such polypeptides include virus proteins, virus structural (Cap) proteins, virus packaging (Rep) proteins, AAV capsid proteins and virus helper proteins. In some embodiments, the virus polypeptide is an AAV virus polypeptide.

In certain embodiments, examples of genes of interest that can be carried by the viral particles produced by the methods describe herein include mammalian polypeptides, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; leptin; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hematopoietic growth factor; tumor necrosis factor-alpha and -beta; a tumor necrosis factor receptor such as death receptor 5 and CD120; TNF-related apoptosis-inducing ligand (TRAIL); B-cell maturation antigen (BCMA); B-lymphocyte stimulator (BLyS); a proliferation-inducing ligand (APRIL); enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; platelet-derived endothelial cell growth factor (PD-ECGF); a vascular endothelial growth factor family protein (e.g., VEGF-A, VEGF-B, VEGF-C, VEGF-D, and P1GF); a platelet-derived growth factor (PDGF) family protein (e.g., PDGF-A, PDGF-B, PDGF-C, PDGF-D, and dimers thereof); fibroblast growth factor (FGF) family such as aFGF, bFGF, FGF4, and FGF9; epidermal growth factor (EGF); receptors for hormones or growth factors such as a VEGF receptor(s) (e.g., VEGFR1, VEGFR2, and VEGFR3), epidermal growth factor (EGF) receptor(s) (e.g., ErbB1, ErbB2, ErbB3, and ErbB4 receptor), platelet-derived growth factor (PDGF) receptor(s) (e.g., PDGFR-α and PDGFR-β), and fibroblast growth factor receptor(s); TIE ligands (Angiopoietins, ANGPT1, ANGPT2); Angiopoietin receptor such as TIE1 and TIE2; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); a chemokine such as CXCL12 and CXCR4; an interferon such as interferon-alpha, -beta, and -gamma; colony stimulating factors (CSFs), e.g., M-CSF, GM-CSF, and G-CSF; a cytokine such as interleukins (TLs), e.g., IL-1 to IL-10; midkine; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD 11a, CD11b, CD11c, CD18, an ICAM, VLA-4 and VCAM; ephrins; Bv8; Delta-like ligand 4 (DLL4); Del-1; BMP9; BMP10; Follistatin; Hepatocyte growth factor (HGF)/scatter factor (SF); Alk1; Robo4; ESM1; Perlecan; EGF-like domain, multiple 7 (EGFL7); CTGF and members of its family; thrombospondins such as thrombospondin1 and thrombospondin2; collagens such as collagen IV and collagen XVIII; neuropilins such as NRP1 and NRP2; Pleiotrophin (PTN); Progranulin; Proliferin; Notch proteins such as Notch1 and Notch4; semaphorins such as Sema3A, Sema3C, and Sema3F; a tumor associated antigen such as CA125 (ovarian cancer antigen); immunoadhesins; and fragments and/or variants of any of the above-listed polypeptides as well as antibodies, including antibody fragments, binding to one or more protein, including, for example, any of the above-listed proteins.

In some embodiments, the gene of interest carried by the viral particles produced by the host cells of the present disclosure may encode proteins that bind to, or interact with, any protein, including, without limitation, cytokines, cytokine-related proteins, and cytokine receptors selected from the group consisting of 8MPI, 8MP2, 8MP38 (GDFIO), 8MP4, 8MP6, 8MP8, CSFI (M-CSF), CSF2 (GM-CSF), CSF3 (G-CSF), EPO, FGF1 (αFGF), FGF2 (βFGF), FGF3 (int-2), FGF4 (HST), FGF5, FGF6 (HST-2), FGF7 (KGF), FGF9, FGF1 0, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFN81, IFNG, IFNWI, FEL1, FEL1 (EPSELON), FEL1 (ZETA), IL A, IL 1B, IL2, IL3, IL4, IL5, IL6, IL7, IL8, IL9, IL1 0, IL 11, IL 12A, IL 12B, IL 13, IL 14, IL 15, IL 16, IL 17, IL 17B, IL 18, IL 19, IL20, IL22, IL23, IL24, IL25, IL26, IL27, IL28A, IL28B, IL29, IL30, PDGFA, PDGFB, TGFA, TGFB1, TGFB2, TGFBb3, LTA (TNF-β), LTB, TNF (TNF-α), TNFSF4 (OX40 ligand), TNFSF5 (CD40 ligand), TNFSF6 (FasL), TNFSF7 (CD27 ligand), TNFSF8 (CD30 ligand), TNFSF9 (4-1 BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL 1IRA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.k.

In some embodiments, the gene of interest carried by the viral particles produced by the host cells of the present disclosure may encode proteins that bind to, or interact with, a chemokine, chemokine receptor, or a chemokine-related protein selected from the group consisting of CCLI (1-309), CCL2 (MCP-1/MCAF), CCL3 (MIP-Iα), CCL4 (MIP-Iβ), CCL5 (RANTES), CCL7 (MCP-3), CCL8 (mcp-2), CCL11 (eotaxin), CCL 13 (MCP-4), CCL 15 (MIP-Iδ), CCL 16 (HCC-4), CCL 17 (TARC), CCL 18 (PARC), CCL 19 (MDP-3b), CCL20 (MIP-3α), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27

(CTACK/ILC), CCL28, CXCLI (GROI), CXCL2 (GR02), CXCL3 (GR03), CXCL5 (ENA-78), CXCL6 (GCP-2), CXCL9 (MIG), CXCL 10 (IP 10), CXCL 11 (1-TAC), CXCL 12 (SDFI), CXCL 13, CXCL 14, CXCL 16, PF4 (CXCL4), PPBP (CXCL7), CX3CL 1 (SCYDI), SCYEI, XCLI (lymphotactin), XCL2 (SCM-Iβ), BLRI (MDR15), CCBP2 (D6/JAB61), CCRI (CKRI/HM145), CCR2 (mcp-TRB IRA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Rα), IL8RB (IL8Rβ), LTB4R (GPR16), TCP10, CKLFSF2, CKLFSF3, CKLFSF4, CKLFSF5, CKLFSF6, CKLFSF7, CKLFSF8, BDNF, C5, C5R1, CSF3, GRCC10 (C10), EPO, FY (DARC), GDF5, HDF1, HDF1α, DL8, PRL, RGS3, RGS13, SDF2, SLIT2, TLR2, TLR4, TREM1, TREM2, and VHL. In some embodiments, the polypeptide expressed by the host cells of the present disclosure may bind to, or interact with, 0772P (CA125, MUC16) (i.e., ovarian cancer antigen), ABCFl; ACVR1; ACVR1B; ACVR2; ACVR2B; ACVRL1; ADORA2A; Aggrecan; AGR2; AICDA; AIF1; AIG1; AKAP1; AKAP2; AMH; AMHIR2; amyloid beta; ANGPTL; ANGPT2; ANGPTL3; ANGPTL4; ANPEP; APC; APOC1; AR; ASLG659; ASPHDI (aspartate beta-hydroxylase domain containing 1; LOC253982); AZGP1 (zinc-a-glycoprotein); B7.1; B7.2; BAD; BAFF-R (B cell-activating factor receptor, BLyS receptor 3, BR3; BAG1; BAI1; BCL2; BCL6; BDNF; BLNK; BLRI (MDR15); BMP1; BMP2; BMP3B (GDF10); BMP4; BMP6; BMP8; BMPR1A; BMPR1B (bone morphogenic protein receptor-type IB); BMPR2; BPAG1 (plectin); BRCA1; Brevican; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP16); CCL16 (HCC-4); CCL17 (TARC); CCL18 (PARC); CCL19 (MIP-30); CCL2 (MCP-1); MCAF; CCL20 (MIP-3α); CCL21 (MTP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Iα); CCL4 (MDP-Iβ); CCL5(RANTES); CCL7 (MCP-3); CCL8 (mcp-2); CCNA1; CCNA2; CCND1; CCNE1; CCNE2; CCR1 (CKRI/HM145); CCR2 (mcp-IRP/RA); CCR3 (CKR/CMKBR3); CCR4; CCR5 (CMKBR5/ChemR13); CCR6 (CMKBR6/CKR-L3/STRL22/DRY6); CCR7 (CKBR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD22 (B-cell receptor CD22-B isoform); CD24; CD28; CD3; CD37; CD38; CD3E; CD3G; CD3Z; CD4; CD40; CD40L; CD44; CD45RB; CD52; CD69; CD72; CD74; CD79A (CD79a, immunoglobulin-associated alpha, a B cell-specific protein); CD79B; CDS; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21/WAF1/Cip1); CDKN1B (p27/Kip1); CDKN1C; CDKN2A (P16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLL-1 (CLEC12A, MICL, and DCAL2); CLN3; CLU (clusterin); CMKLR1; CMKOR1 (RDC1); CNR1; COL 18A1; COL1A1; COL4A3; COL6A1; complement factor D; CR2; CRP; CRIPTO (CR, CR1, CRGF, CRIPTO, TDGF1, teratocarcinoma-derived growth factor); CSFI (M-CSF); CSF2 (GM-CSF); CSF3 (GCSF); CTLA4; CTNNB1 (b-catenin); CTSB (cathepsin B); CX3CL1 (SCYDI); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR5 (Burkitt's lymphoma receptor 1, a G protein-coupled receptor); CXCR6 (TYMSTR/STRL33/Bonzo); CYB5; CYC1; CYSLTR1; DAB2IP; DES; DKFZp451J0118; DNCLI; DPP4; E16 (LAT1, SLC7A5); E2F1; ECGF1; EDG1; EFNA1; EFNA3; EFNB2; EGF; EGFR; ELAC2; ENG; ENOl; ENO2; ENO3; EPHB4; EphB2R; EPO; ERBB2 (Her-2); EREG; ERK8; ESR1; ESR2; ETBR (Endothelin type B receptor); F3 (TF); FADD; FasL; FASN; FCER1A; FCER2; FCGR3A; FcRH1 (Fc receptor-like protein 1); FcRH2 (IFGP4, IRTA4, SPAP1A (SH2 domain containing phosphatase anchor protein 1a), SPAP1B, SPAP1C); FGF; FGF1 (αFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR; FGFR3; FIGF (VEGFD); FEL1 (EPSILON); FIL1 (ZETA); FLJ12584; FLJ25530; FLRTI (fibronectin); FLT1; FOS; FOSL1 (FRA-1); FY (DARC); GABRP (GABAa); GAGEB1; GAGEC1; GALNAC4S-6ST; GATA3; GDF5; GDNF-Ra1 (GDNF family receptor alpha 1; GFRA1; GDNFR; GDNFRA; RETL1; TRNR1; RETIL; GDNFR-alpha1; GFR-ALPHA-1); GEDA; GFI1; GGT1; GM-CSF; GNASI; GNRHI; GPR2 (CCR10); GPR19 (G protein-coupled receptor 19; Mm.4787); GPR31; GPR44; GPR54 (KISS1 receptor; KISSIR; GPR54; HOT7T175; AXOR12); GPR81 (FKSG80); GPR172A (G protein-coupled receptor 172A; GPCR41; FLJ11856; D15Ertd747e); GRCCIO (C10); GRP; GSN (Gelsolin); GSTP1; HAVCR2; HDAC4; HDAC5; HDAC7A; HDAC9; HGF; HIF1A; HOP1; histamine and histamine receptors; HLA-A; HLA-DOB (Beta subunit of MHC class II molecule (Ia antigen); HLA-DRA; HM74; HMOXI; HUMCYT2A; ICEBERG; ICOSL; 1D2; IFN-a; IFNA1; IFNA2; IFNA4; IFNA5; IFNA6; IFNA7; IFNB1; IFNgamma; DFNW1; IGBP1; IGF1; IGF1R; IGF2; IGFBP2; IGFBP3; IGFBP6; IL-1; IL10; IL10RA; IL10RB; IL11; IL1 IRA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; ILIF10; IL1F5; IL1F6; IL1F7; IL1F8; IL1F9; IL1HY1; IL1R1; IL1R2; IL1RAP; IL1RAPL1; IL1RAPL2; IL1RL1; IL1RL2, ILIRN; IL2; IL20; IL20Rα; IL21 R; IL22; IL-22c; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); influenza A; influenza B; EL7; EL7R; EL8; IL8RA; DL8RB; IL8RB; DL9; DL9R; DLK; INHA; INHBA; INSL3; INSL4; IRAK1; IRTA2 (Immunoglobulin superfamily receptor translocation associated 2); ERAK2; ITGA1; ITGA2; ITGA3; ITGA6 (a6 integrin); ITGAV; ITGB3; ITGB4 (b4 integrin); a407 and aEP7 integrin heterodimers; JAG1; JAK1; JAK3; JUN; K6HF; KAI1; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); LGR5 (leucine-rich repeat-containing G protein-coupled receptor 5; GPR49, GPR67); Lingo-p75; Lingo- Troy; LPS; LTA (TNF-b); LTB; LTB4R (GPR16); LTB4R2; LTBR; LY64 (Lymphocyte antigen 64 (RP105), type I membrane protein of the leucine rich repeat (LRR) family); Ly6E (lymphocyte antigen 6 complex, locus E; Ly67, RIG-E, SCA-2, TSA-1); Ly6G6D (lymphocyte antigen 6 complex, locus G6D; Ly6-D, MEGT1); LY6K (lymphocyte antigen 6 complex, locus K; LY6K; HSJ001348; FLJ35226); MACMARCKS; MAG or OMgp; MAP2K7 (c-Jun); MDK; MDP; MIB1; midkine; MEF; MIP-2; MKI67; (Ki-67); MMP2; MMP9; MPF (MPF, MSLN, SMR, megakaryocyte potentiating factor, mesothelin); MS4A1; MSG783 (RNF124, hypothetical protein FLJ20315); MSMB; MT3 (metallothionectin-111); MTSS1; MUC1 (mucin); MYC; MY088; Napi3b (also known as NaPi2b) (NAPI-3B, NPTIIb, SLC34A2, solute carrier family 34 (sodium phosphate), member 2, type II sodium-dependent phosphate transporter 3b); NCA; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NR0B1; NR0B2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; OX40; P2RX7; P2X5 (Purinergic receptor P2X ligand-gated ion channel 5); PAP; PART1; PATE; PAWR; PCA3; PCNA; PD-Li; PD-L2; PD-1; POGFA; POGFB; PECAMI; PF4 (CXCL4); PGF; PGR; phosphacan; PIAS2; PIK3CG; PLAU (uPA); PLG; PLXDCI; PMEL17 (silver homolog; SILV; D12S53E; PMEL17; SI; SIL); PPBP (CXCL7); PPID; PRI; PRKCQ; PRKDI; PRL; PROC; PROK2; PSAP; PSCA hlg (2700050C12Rik, C530008016Rik, RIKEN cDNA 2700050C12, RIKEN cDNA 2700050C12 gene); PTAFR; PTEN; PTGS2 (COX-2); PTN; RAC2 (p21 Rac2); RARB; RET (ret proto-oncogene; MEN2A; HSCR1; MEN2B; MTC1; PTC; CDHF12; Hs.168114; RET51; RET-ELE1); RGSI; RGS13; RGS3; RNF110 (ZNF144); ROBO2; S100A2; SCGB1D2 (lipophilin B); SCGB2A1 (mammaglobin2); SCGB2A2 (mammaglobin 1); SCYEI (endothelial Monocyte-activating cytokine); SDF2; Sema 5b (FLJ10372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B); SERPINAI; SERPINA3; SERPINB5 (maspin); SERPINEI(PAI-1); SER-PDMFI; SHBG; SLA2; SLC2A2; SLC33A1; SLC43A1; SLIT2; SPPI; SPRRIB (Sprl); ST6GAL1; STABI; STAT6; STEAP (six transmembrane epithelial antigen of prostate); STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein); TB4R2; TBX21; TCPIO; TOGFI; TEK; TENB2 (putative transmembrane proteoglycan); TGFA; TGFBI; TGFB1II; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor; TLR1; TLR2; TLR3; TLR4; TLR5; TLR6; TLR7; TLR8; TLR9; TLR10; TMEFF1 (transmembrane protein with EGF-like and two follistatin-like domains 1; Tomoregulin-1); TMEM46 (shisa homolog 2); TNF; TNF-a; TNFAEP2 (B94); TNFAIP3; TNFRSFIIA; TNFRSFIA; TNFRSFIB; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSFS (CD30 ligand); TNFSF9 (4-1 BB ligand); TOLLIP; Toll-like receptors; TOP2A (topoisomerase Ea); TP53; TPM1; TPM2; TRADD; TMEM118 (ring finger protein, transmembrane 2; RNFT2; FLJ14627); TRAF1; TRAF2; TRAF3; TRAF4; TRAF5; TRAF6; TREM1; TREM2; TrpM4 (BR22450, FLJ20041, TRPM4, TRPM4B, transient receptor potential cation channel, subfamily M, member 4); TRPC6; TSLP; TWEAK; Tyrosinase (TYR; OCAIA; OCA1A; tyrosinase; SHEP3); VEGF; VEGFB; VEGFC; versican; VHL C5; VLA-4; XCL1 (lymphotactin); XCL2 (SCM-1b); XCRI(GPR5/ CCXCRI); YY1; and/or ZFPM2.

Many other virus components and/or other genes of interest may be packaged by the host cells in accordance with the present disclosure, and the above lists are not meant to be limiting.

The methods of the present disclosure may be employed in the production of viral particles of interest at manufacturing scale. "Manufacturing scale" production of therapeutic proteins, or other proteins, utilize cell cultures ranging from about 400 L to about 80,000 L, depending on the protein being produced and the need. Typically, such manufacturing scale production utilizes cell culture sizes from about 400 L to about 25,000 L. Within this range, specific cell culture sizes such as 4,000 L, about 6,000 L, about 8,000, about 10,000, about 12,000 L, about 14,000 L, or about 16,000 L may be utilized.

6. EXEMPLARY EMBODIMENTS

The present disclosure relates to modified mammalian cells, (e.g., Chinese Hamster Ovary (CHO) cells) that have reduced or eliminated activity of certain host cell proteins, e.g., host cell enzymes, including but not limited to, certain lipases, esterases, and/or hydrolases, methods for making such cells, and methods of using such cells in the production of a product of interest, e.g., a recombinant protein.

In certain embodiments, the present disclosure provides a recombinant host cell where the cell is modified to reduce or eliminate the activity of one or more enzyme relative to the activity of the enzyme in an unmodified cell. In certain embodiments, the one or more enzyme is selected from the group consisting of: Lipoprotein lipase (LPL); phospholipase B-domain containing 2 (PLBL2/PLBD2); Lipase A (Lysosomal acid lipase/cholesteryl ester hydrolase, Lipase) (LIPA); Phospholipase A-2-activating protein (PLAA); Phospholipase D3 (PLD3); Phospholipase A2 group XV (LPLA2); Phospholipase C beta 1 (PLCB1); Phospholipase C delta 1 (PLCD1); DDHD domain containing protein 1 (Fragment) (DDHD1); Lysophospholipase-like protein 1 (LYPLA1); Phospholipase A2 group XIIA (PLA2G12A); Peroxiredoxin 6 (PRDX6); Sphingomyelin phosphodiesterase (SMPD1); Palmitoyl-protein thioesterase 1 (PPT1); Isoamyl acetate hydrolyzing esterase 1 (putative) (IAH1); OTU deubiquitinase, ubiquitin aldehyde binding 1 (OTUB1); Lysophospholipase 2 (Acyl-protein thioesterase 2) (LYPLA2); Acyl-coenzyme A thioesterase 13 (ACOT13); Fatty acid synthase (FASN); Phospholipase A2 group VII (PLA2G7); Ubiquitin specific peptidase 5 (USP5); N-acyl-sphingosine amidohydrolase 1 (Acid ceramidase) (ASAH1); Lipase maturation factor 1 (LMF1); Apolipoprotein-CII (APOC2); Acylcarnitine hydrolase (HACH); Carboxylesterase 1F (CES1F) or Liver carboxylesterase B-1-like (CES-B1L); Lysophospholipase 1 (LYPLA1); Carboxylesterase 1 (CES1); Phospholipase A1 member A (PLA1A); and Sialic acid acetylesterase (SIAE).

In certain embodiments, the activity of: a) PPT1; b) LPLA2; LPL; and LIPA; c) LPLA2; LPL; LIPA; PPT1; PLBL2; PLD3; and SMPD1; d) LPLA2; LPL; LIPA; PPT1; PLBL2; PLD3; SMPD1; PLAA; IAH1; OTUB1; LYPLA2; and PLA2G12A; e) BAX; BAK; LPLA2; LPL; LIPA; PPT1; PLD3; and SMPD1; f) BAX; BAK; LPLA2; LPL; LIPA; PPT1; PLBL2; PLD3; SMPD1; CLU; PRDX1; PLAA; and ACOT13; g) LPLA2; LPL; and PPT1; h) LPLA2; LPL; LIPA; and PPT1; i) HACH; CES1F/CES-B1L; and LYPLA1; j) LPLA2; LPL; LIPA; PPT1; HACH; CES1F/CES-B1L; and LYPLA1; k) SMPD1; CES1; PLA1A; and SIAE; l) LPLA2; LPL; LIPA; PPT1; HACH; CES1F/CES-B1L; LYPLA1; SMPD1; CES1; PLA1A; and SIAE; m) LPLA2; LMF1; LIPA; PPT1; HACH; CES1F/CES-B1L; and LYPLA1; n) LPLA2; LMF1; APOC2; LIPA; PPT1; HACH; CES1F/CES-B1L; and LYPLA1; o) LMF1 and APOC2 in a recombinant host cell is reduced or eliminated.

In certain embodiments, the activity of the one or more enzyme in a recombinant host cell is reduced or eliminated by: (a) knocking down expression of the enzyme; (b) or knocking out expression of the enzyme; or (c) altering the nucleic acid sequence encoding the enzyme.

In certain embodiments, the present disclosure is directed to a recombinant host cell comprising one or more altered enzyme genes. In certain embodiments, the one or more altered enzyme genes have no detectable enzymatic activity. In certain embodiments, the recombinant host cell comprises a nucleic acid sequence encoding a product of interest. In certain embodiments, the nucleic acid sequence is integrated in the cellular genome of the mammalian cell at a targeted location. In certain embodiments, the recombinant host cell further comprises a nucleic acid encoding the product of interest that is randomly integrated in the cellular genome of the mammalian cell. In certain embodiments, the modified cell does not express any detectable LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides compositions comprising a recombinant host cell described in the present disclosure.

In certain embodiments, the present disclosure provides a method for reducing enzymatic activity in a cell, where the method comprises knocking down or knocking out the expression of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing enzymatic activity in a cell, where the method comprises modulating a cell culture process and/or media composition, wherein modulating a cell culture process and/or media composition results in reduced activity of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing enzymatic activity in a cell, wherein the method comprises selecting cells with reduced activity of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing enzymatic activity in a cell, wherein the method comprises altering the gene encoding one or more of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method for reducing or eliminating enzymatic activity in a cell, wherein the method comprises administering to the cell a genetic engineering system, wherein the genetic engineering system knocks down or knocks out the expression of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; and/or ASAH1; LMF1; APOC2; HACH; CES1F/CES-B1L; LYPLA1; CES1; PLA1A; and/or SIAE.

In certain embodiments, the present disclosure provides a method for reducing or eliminating enzymatic activity in a cell, wherein the method comprises administering to the cell a genetic engineering system, wherein the genetic engineering system alters the nucleic acid sequence encoding one or more of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; and ASAH1 so that the one or more of LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE have reduced or eliminated enzymatic activity.

In certain embodiments, the present disclosure provides a method of producing a product of interest comprising culturing mammalian cells expressing the product of interest, wherein the mammalian cells express the product of interest and have reduced or eliminated activity of one or more of the following LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a method of culturing a population of mammalian cells expressing a product of interest, wherein the mammalian cells have reduced or eliminated activity of one or more of the following LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain embodiments, the present disclosure provides a recombinant host cell comprising one or more altered enzyme genes. In certain embodiments, the one or more altered enzyme genes are altered by disruption of a coding region. In certain embodiments, the one or more enzyme genes alteration comprises a biallelic alteration. In certain embodiments, the one or more enzyme genes alteration comprises a deletion of 1 or more base pairs, 2 or more base pairs, 3 or more base pairs, 4 or more base pairs, 5 or more base pairs, 6 or more base pairs, 7 or more base pairs, 8 or more base pairs, 9 or more base pairs, 10 or more base pairs, 11 or more base pairs, 12 or more base pairs, 13 or more base pairs, 14 or more base pairs, 15 or more base pairs, 16 or more base pairs, 17 or more base pairs, 18 or more base pairs, 19 or more base pairs, or 20 or more base pairs. In certain embodiments, the one or more enzyme genes are LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain of the above described embodiments, the genetic engineering system is selected from the group consisting of a CRISPR/Cas system, a zinc-finger nuclease (ZFN) system, a transcription activator-like effector nuclease (TALEN) system and a combination thereof. In certain of the above described embodiments, the genetic engineering system is a CRISPR/Cas9 system.

In certain of the above described embodiments, the CRISPR/Cas9 system comprises: (a) a Cas9 molecule, and (b) one or more guide RNAs (gRNAs) comprising a targeting sequence that is complementary to a target sequence in a gene encoding LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE.

In certain of the above described embodiments, the genetic engineering system comprises an RNA selected from the group consisting of: a short hairpin RNA (shRNA), a small interference RNA (siRNA), and a microRNA (miRNA), wherein the RNA is complementary to a portion of an mRNA expressed by one or more of the LPL; PLBL2/PLBD2; LIPA; PLAA; PLD3; LPLA2; PLCB1; PLCD1; DDHD1; LYPLA1; PLA2G12A; PRDX6; SMPD1; PPT1; IAH1; OTUB1; LYPLA2; ACOT13; FASN; PLA2G7; USP5; ASAH1; LMF1; APOC2; HACH; CES1F/CES-B1L; LYPLA1; CES1; PLA1A; and/or SIAE genes. In certain of the above described embodiments, the genetic engineering system is a zinc-finger nuclease (ZFN) system or a transcription activator-like effector nuclease (TALEN) system.

In certain of the above described embodiments, the reduction or elimination of activity is of: a) PPT1; b) LPLA2; LPL; and LIPA; c) LPLA2; LPL; LIPA; PPT1; PLBL2; PLD3; and SMPD1; d) LPLA2; LPL; LIPA; PPT1; PLBL2; PLD3; SMPD1; PLAA; IAH1; OTUB1; LYPLA2; and PLA2G12A; e) BAX; BAK; LPLA2; LPL; LIPA; PPT1; PLD3; and SMPD1; f) BAX; BAK; LPLA2; LPL; LIPA; PPT1; PLBL2; PLD3; SMPD1; CLU; PRDX1; PLAA; and ACOT13 or g) LPLA2; LPL; and PPT1; h) LPLA2; LPL; LIPA; and PPT1; i) HACH; CES1F/CES-B1L; and LYPLA1; j) LPLA2; LPL; LIPA; PPT1; HACH; CES1F/CES-B1L; and LYPLA1; k) SMPD1; CES1; PLA1A; and SIAE; 1) LPLA2; LPL; LIPA; PPT1; HACH; CES1F/CES-B1L; LYPLA1; SMPD1; CES1; PLA1A; and SIAE; m) LPLA2; LMF1; LIPA; PPT1; HACH; CES1F/CES-B1L; and LYPLA1; n) LPLA2; LMF1; APOC2; LIPA; PPT1; HACH; CES1F/CES-B1L; and LYPLA1; o) LMF1 and APOC2 in the mammalian cells.

In certain of the above described embodiments, the methods provided in the present disclosure further comprise purifying the product of interest, harvesting the product of interest, and/or formulating the product of interest.

In certain of the above described embodiments, the degradation of a polyoxyethylene sorbitan monolaurate is reduced. In certain of the above described embodiments, the degradation of polysorbate 20 (PS20 or Tween 20) is reduced. In certain of the above described embodiments, the degradation of polysorbate 80 (PS80 or Tween 80) is reduced.

In certain of the above described embodiments, the cell is a mammalian cell. In certain of the above described embodiments, the mammalian cell is a CHO cell.

In certain of the above described embodiments, the cell expresses a product of interest. In certain of the above described embodiments, the product of interest expressed by the mammalian cells is encoded by a nucleic acid sequence. In certain of the above described embodiments, the nucleic acid sequence is integrated in the cellular genome of the mammalian cells at a targeted location. In certain of the above described embodiments, the product of interest expressed by the cells is further encoded by a nucleic acid sequence that is randomly integrated in the cellular genome of the mammalian cells.

In certain of the above described embodiments, the product of interest comprises a protein, a viral particle or a viral vector. In certain of the above described embodiments, the product of interest comprises a recombinant protein. In certain of the above described embodiments, the product of interest comprises an antibody or an antigen-binding fragment thereof. In certain of the above described embodiments, the antibody is a multispecific antibody or an antigen-binding fragment thereof. In certain of the above described embodiments, the antibody consists of a single heavy chain sequence and a single light chain sequence or antigen-binding fragments thereof. In certain of the above described embodiments, the antibody is a chimeric antibody, a human antibody or a humanized antibody. In certain of the above described embodiments, the antibody is a monoclonal antibody.

In certain embodiments, the modified cell of the present disclosure does not express any detectable PPT1. In certain embodiments, the modified cell of the present disclosure does not express any detectable LPLA2, LPL, and LIPA. In certain embodiments, the modified cell of the present disclosure does not express any detectable LPLA2, LPL, LIPA, PPT1, PLBL2, PLD3, and SMPD1. In certain embodiments, the modified cell of the present disclosure does not express any detectable LPLA2, LPL, LIPA, PPT1, PLBL2, PLD3, SMPD1, PLAA, IAH1, OTUB1, LYPLA2, and PLA2G12A. In certain embodiments, the modified cell of the present disclosure does not express any detectable BAX, BAK, LPLA2, LPL, LIPA, PPT1, PLD3, and SMPD1. In certain embodiments, the modified cell of the present disclosure does not express any detectable BAX, BAK, LPLA2, LPL, LIPA, PPT1, PLBL2, PLD3, SMPD1, CLU, PRDX1, PLAA, and ACOT13. In certain embodiments, the modified cell of the present disclosure does not express any detectable LPLA2, LPL, and PPT1. In certain embodiments, the modified cell of the present disclosure does not express any detectable LPLA2, LPL, LIPA and PPT1. In certain embodiments, the modified cell of the present disclosure does not express any detectable HACH, CES1F/CES-B1L, and LYPLA1. In certain embodiments, the modified cell of the present disclosure does not express any detectable LPLA2, LPL, LIPA, PPT1, HACH, CES1F/CES-B1L, and LYPLA1. In certain embodiments, the modified cell of the present disclosure does not express any detectable SMPD1, CES1, PLA1A, and SIAE. In certain embodiments, the modified cell of the present disclosure does not express any detectable LPLA2, LPL, LIPA, PPT1, HACH, CES1F/CES-B1L, LYPLA1, SMPD1, CES1, PLA1A, and SIAE. In certain embodiments, the modified cell of the present disclosure does not express any detectable LPLA2, LMF1, LIPA, PPT1, HACH, CES1F/CES-B1L, and LYPLA1. In certain embodiments, the modified cell of the present disclosure does not express any detectable LPLA2, LMF1, APOC2, LIPA, PPT1, HACH, CES1F/CES-B1L, and LYPLA1. In certain embodiments, the modified cell of the present disclosure does not express any detectable LMF1 and APOC2.

In certain embodiments, the present disclosure provides a recombinant host cell, wherein the cell is modified to reduce or eliminate the activity of PPT1 enzymes relative to the activity of the enzymes in an unmodified cell. In certain embodiments, the present disclosure provides a recombinant host cell, wherein the cell is modified to reduce or eliminate the activity of LPLA2, LPL, and LIPA enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, PLBL2, PLD3, and SMPD1 enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, PLBL2, PLD3, SMPD1, PLAA, IAH1, OTUB1, LYPLA2, and PLA2G12A enzymes relative to the activity of the enzymes in an unmodified cell. In certain embodiments, the present disclosure provides a recombinant host cell, wherein the cell is modified to reduce or eliminate the activity of BAX, BAK, LPLA2, LPL, LIPA, PPT1, PLD3, and SMPD1 enzymes relative to the activity of the enzymes in an unmodified cell. In certain embodiments, the present disclosure provides a recombinant host cell, wherein the cell is modified to reduce or eliminate the activity of BAX, BAK, LPLA2, LPL, LIPA, PPT1, PLBL2, PLD3, SMPD1, CLU, PRDX1, PLAA, and ACOT13 enzymes relative to the activity of the enzymes in an unmodified cell. In certain embodiments, the present disclosure provides a recombinant host cell, wherein the cell is modified to reduce or eliminate the activity of LPLA2, LPL, and PPT1 enzymes relative to the activity of the enzymes in an unmodified cell. In certain embodiments, the present disclosure provides a recombinant host cell, wherein the cell is modified to reduce or eliminate the activity of LPLA2, LPL, LIPA and PPT1 enzymes relative to the activity of the enzymes in an unmodified cell. In certain embodiments, the present disclosure provides recombinant host cell, wherein the cell is modified to reduce or eliminate the activity of HACH, CES1F/CES-B1L, and LYPLA1 enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, HACH, CES1F/CES-B1L, and LYPLA1 enzymes relative to the activity of the enzymes in an unmodified cell. In certain embodiments, the present disclosure provides a recombinant host cell, wherein the cell is modified to reduce or eliminate the activity of SMPD1, CES1, PLA1A, and SIAE enzymes relative to the activity of the enzymes in an unmodified cell. In certain embodiments, the present disclosure provides a recombinant host cell, wherein the cell is modified to reduce or eliminate the activity of LPLA2, LPL, LIPA, PPT1, HACH, CES1F/CES-B1L, LYPLA1, SMPD1, CES1, PLA1A, and SIAE enzymes relative to the activity of the enzymes in an unmodified cell. In certain embodiments, the present disclosure provides a recombinant host cell, wherein the cell is modified to reduce or eliminate the activity of LPLA2, LMF1, LIPA, PPT1, HACH, CES1F/CES-B1L, and LYPLA1 enzymes relative to the activity of the enzymes in an unmodified cell. In certain embodiments, the present disclosure provides a recombinant host cell, wherein the cell is modified to reduce or eliminate the activity of LPLA2, LMF1, APOC2, LIPA, PPT1, HACH, CES1F/CES-B1L and LYPLA1 enzymes relative to the activity of the enzymes in an unmodified cell. In certain embodiments, the present disclosure provides a recombinant host cell, wherein the cell is modified to reduce or eliminate the activity of LMF1 and APOC2 enzymes relative to their activity in an unmodified cell.

In certain embodiments, the present disclosure provides a method for reducing enzymatic activity in a cell, comprising knocking down or knocking out the expression of PPT1. In certain embodiments, the present disclosure provides a method for reducing enzymatic activity in a cell, comprising knocking down or knocking out the expression of LPLA2, LPL, and LIPA. In certain embodiments, the present disclosure provides a method for reducing enzymatic activity in a cell, comprising knocking down or knocking out the expression of LPLA2, LPL, LIPA, PPT1, PLBL2, PLD3, and SMPD1. In certain embodiments, the present disclosure provides a method for reducing enzymatic activity in a cell, comprising knocking down or knocking out the expression of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising knocking down or knocking out the expression of BAX, BAK, LPLA2, LPL, LIPA, PPT1, PLD3, and SMPD1. In certain embodiments, the present disclosure provides a method for reducing enzymatic activity in a cell, comprising knocking down or knocking out the expression of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising knocking down or knocking out the expression of LPLA2, LPL, and PPT1. In certain embodiments, the present disclosure provides a method for reducing enzymatic activity in a cell, comprising knocking down or knocking out the expression of LPLA2, LPL, LIPA and PPT1. In certain embodiments, the present disclosure provides a method for reducing enzymatic activity in a cell, comprising knocking down or knocking out the expression of HACH, CES1F/CES-B1L, and LYPLA1. In certain embodiments, the present disclosure provides a method for reducing enzymatic activity in a cell, comprising knocking down or knocking out the expression of LPLA2, LPL, LIPA, PPT1, HACH, CES1F/CES-B1L, and LYPLA1. In certain embodiments, the present disclosure provides a method for reducing enzymatic activity in a cell, comprising knocking down or knocking out the expression of SMPD1, CES1, PLA1A, and SIAE. In certain embodiments, the present disclosure provides a method for reducing enzymatic activity in a cell, comprising knocking down or knocking out the expression of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising knocking down or knocking out the expression of LPLA2, LMF1, LIPA, PPT1, HACH, CES1F/CES-B1L, and LYPLA1. In certain embodiments, the present disclosure provides a method for reducing enzymatic activity in a cell, comprising knocking down or knocking out the expression of LPLA2, LMF1, APOC2, LIPA, PPT1, HACH, CES1F/CES-B1L, and LYPLA1. In certain embodiments, the present disclosure provides a method for reducing enzymatic activity in a cell, comprising knocking down or knocking out the expression of LMF1 and APOC2.

In certain embodiments, the present disclosure provides a method for reducing enzymatic activity in a cell, comprising modulating a cell culture process and/or media composition, wherein modulating a cell culture process and/or media composition results in reduced activity of PPT1. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, and LIPA. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, PLBL2, PLD3, and SMPD1. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising modulating a cell culture process and/or media composition, wherein modulating a cell culture process and/or media composition results in reduced activity of BAX, BAK, LPLA2, LPL, LIPA, PPT1, PLD3, and SMPD1. In certain embodiments, the present disclosure provides a method for reducing enzymatic activity in a cell, comprising modulating a cell culture process and/or media composition, wherein modulating a cell culture process and/or media composition results in reduced activity of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, and PPT1. In certain embodiments, the present disclosure provides a method for reducing enzymatic activity in a cell, comprising modulating a cell culture process and/or media composition, wherein modulating a cell culture process and/or media composition results in reduced activity of LPLA2; LPL; LIPA and PPT1. In certain embodiments, the present disclosure provides a method for reducing enzymatic activity in a cell, comprising modulating a cell culture process and/or media composition, wherein modulating a cell culture process and/or media composition results in reduced activity of HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of SMPD1, CES1, PLA1A, and SIAE. In certain embodiments, the present disclosure provides a method for reducing enzymatic activity in a cell, comprising modulating a cell culture process and/or media composition, wherein modulating a cell culture process and/or media composition results in reduced activity of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising modulating a cell culture process and/or media composition, wherein modulating a cell culture process and/or media composition results in reduced activity of LPLA2, LMF1, LIPA, PPT1, HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of LPLA2, LMF1, APOC2, LIPA, PPT1, HACH, CES1F/CES-B1L, and LYPLA1. In certain embodiments, the present disclosure provides a method for reducing enzymatic activity in a cell, comprising modulating a cell culture process and/or media composition, wherein modulating a cell culture process and/or media composition results in reduced activity of LMF1 and APOC2.

In certain embodiments, the present disclosure provides a method for reducing enzymatic activity in a cell, comprising selecting cells with reduced activity of PPT1. In certain embodiments, the present disclosure provides a method for reducing enzymatic activity in a cell, comprising selecting cells with reduced activity of LPLA2, LPL, and LIPA. In certain embodiments, the present disclosure provides a method for reducing enzymatic activity in a cell, comprising selecting cells with reduced activity of LPLA2, LPL, LIPA, PPT1, PLBL2, PLD3, and SMPD1. In certain embodiments, the present disclosure provides a method for reducing enzymatic activity in a cell, comprising selecting cells with reduced activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising selecting cells with reduced activity of BAX, BAK, LPLA2, LPL, LIPA, PPT1, PLD3, and SMPD1. In certain embodiments, the present disclosure provides a method for reducing enzymatic activity in a cell, comprising selecting cells with reduced activity of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising selecting cells with reduced activity of LPLA2, LPL, and PPT1. In certain embodiments, the present disclosure provides a method for reducing enzymatic activity in a cell, comprising selecting cells with reduced activity of LPLA2, LPL, LIPA and PPT1. In certain embodiments, the present disclosure provides a method for reducing enzymatic activity in a cell, comprising selecting cells with reduced activity of HACH, CES1F/CES-B1L, and LYPLA1. In certain embodiments, the present disclosure provides a method for reducing enzymatic activity in a cell, comprising selecting cells with reduced activity of LPLA2, LPL, LIPA, PPT1, HACH, CES1F/CES-B1L, and LYPLA1. In certain embodiments, the present disclosure provides a method for reducing enzymatic activity in a cell, comprising selecting cells with reduced activity of SMPD1, CES1, PLA1A, and SIAE. In certain embodiments, the present disclosure provides a method for reducing enzymatic activity in a cell, comprising selecting cells with reduced activity of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising selecting cells with reduced activity of LPLA2, LMF1, LIPA, PPT1, HACH, CES1F/CES-B1L, and LYPLA1. In certain embodiments, the present disclosure provides a method for reducing enzymatic activity in a cell, comprising selecting cells with reduced activity of LPLA2, LMF1, APOC2, LIPA, PPT1, HACH, CES1F/CES-B1L, and LYPLA1. In certain embodiments, the present disclosure provides a method for reducing enzymatic activity in a cell, comprising selecting cells with reduced activity of LMF1 and APOC2.

In certain embodiments, the present disclosure provides a method for reducing enzymatic activity in a cell, comprising altering the gene encoding PPT1. In certain embodiments, the present disclosure provides a method for reducing enzymatic activity in a cell, comprising altering the gene encoding one or more of LPLA2, LPL, and LIPA. In certain embodiments, the present disclosure provides a method for reducing enzymatic activity in a cell, comprising altering the gene encoding one or more of LPLA2, LPL, LIPA, PPT1, PLBL2, PLD3, and SMPD1. In certain embodiments, the present disclosure provides a method for reducing enzymatic activity in a cell, comprising altering the gene encoding one or more of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing enzymatic activity in a cell, comprising altering the gene encoding one or more of BAX, BAK, LPLA2, LPL, LIPA, PPT1, PLD3, and SMPD1. In certain embodiments, the present disclosure provides a method for reducing enzymatic activity in a cell, comprising altering the gene encoding one or more of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing enzymatic activity in a cell, comprising altering the gene encoding one or more of LPLA2, LPL, and PPT1. In certain embodiments, the present disclosure provides a method for reducing enzymatic activity in a cell, comprising altering the gene encoding one or more of LPLA2, LPL, LIPA and PPT1. In certain embodiments, the present disclosure provides a method for reducing enzymatic activity in a cell, comprising altering the gene encoding one or more of HACH, CES1F/CES-B1L, and LYPLA1. In certain embodiments, the present disclosure provides a method for reducing enzymatic activity in a cell, comprising altering the gene encoding one or more of LPLA2, LPL, LIPA, PPT1, HACH, CES1F/CES-B1L, and LYPLA1. In certain embodiments, the present disclosure provides a method for reducing enzymatic activity in a cell, comprising altering the gene encoding one or more of SMPD1, CES1, PLA1A, and SIAE. In certain embodiments, the present disclosure provides a method for reducing enzymatic activity in a cell, comprising altering the gene encoding one or more of LPLA2, LPL, LIPA, PPT1, HACH, CES1F/CES-B1L, LYPLA1, SMPD1, CES1, PLA1A, and SIAE. In certain embodiments, the present disclosure provides a method for reducing enzymatic activity in a cell, comprising altering the gene encoding one or more of LPLA2, LMF1, LIPA, PPT1, HACH, CES1F/CES-B1L, and LYPLA1. In certain embodiments, the present disclosure provides a method for reducing enzymatic activity in a cell, comprising altering the gene encoding one or more of LPLA2, LMF1, APOC2, LIPA, PPT1, HACH, CES1F/CES-B1L, and LYPLA1. In certain embodiments, the present disclosure provides a method for reducing enzymatic activity in a cell, comprising altering the gene encoding one or more of LMF1 and APOC2.

In certain embodiments, the present disclosure provides a method for reducing or eliminating enzymatic activity in a cell, comprising administering to the cell a genetic engineering system, wherein the genetic engineering system knocks down or knocks out the expression of PPT1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, and LIPA. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, PLBL2, PLD3, and SMPD1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, PLBL2, PLD3, SMPD1, PLAA, IAH1, OTUB1, LYPLA2, and PLA2G12A. In certain embodiments, the present disclosure provides a method for reducing or eliminating enzymatic activity in a cell, comprising administering to the cell a genetic engineering system, wherein the genetic engineering system knocks down or knocks out the expression of BAX, BAK, LPLA2, LPL, LIPA, PPT1, PLD3, and SMPD1. In certain embodiments, the present disclosure provides a method for reducing or eliminating enzymatic activity in a cell, comprising administering to the cell a genetic engineering system, wherein the genetic engineering system knocks down or knocks out the expression of BAX, BAK, LPLA2, LPL, LIPA, PPT1, PLBL2, PLD3, SMPD1, CLU, PRDX1, PLAA, and ACOT13. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, and PPT1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA and PPT1. In certain embodiments, the present disclosure provides a method for reducing or eliminating enzymatic activity in a cell, comprising administering to the cell a genetic engineering system, wherein the genetic engineering system knocks down or knocks out the expression of HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of SMPD1, CES1, PLA1A, and SIAE. In certain embodiments, the present disclosure provides a method for reducing or eliminating enzymatic activity in a cell, comprising administering to the cell a genetic engineering system, wherein the genetic engineering system knocks down or knocks out the expression of LPLA2, LPL, LIPA, PPT1, HACH, CES1F/CES-B1L, LYPLA1, SMPD1, CES1, PLA1A, and SIAE. In certain embodiments, the present disclosure provides a method for reducing or eliminating enzymatic activity in a cell, comprising administering to the cell a genetic engineering system, wherein the genetic engineering system knocks down or knocks out the expression of LPLA2, LMF1, LIPA, PPT1, HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of LPLA2, LMF1, APOC2, LIPA, PPT1, HACH, CES1F/CES-B1L, and LYPLA1. In certain embodiments, the present disclosure provides a method for reducing or eliminating enzymatic activity in a cell, comprising administering to the cell a genetic engineering system, wherein the genetic engineering system knocks down or knocks out the expression of LMF1 and APOC2.

In certain embodiments, the present disclosure provides a method for reducing or eliminating enzymatic activity in a cell, comprising administering to the cell a genetic engineering system, wherein the genetic engineering system alters the nucleic acid sequence encoding PPT1 so that the PPT1 has reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, and LIPA so that the LPLA2, LPL, and LIPA have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, PLBL2, PLD3, and SMPD1 so that the LPLA2, LPL, LIPA, PPT1, PLBL2, PLD3, and SMPD1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, PLBL2, PLD3, SMPD1, PLAA, IAH1, OTUB1, LYPLA2, and PLA2G12A so that the LPLA2, LPL, LIPA, PPT1, PLBL2, PLD3, SMPD1, PLAA, IAH1, OTUB1, LYPLA2, and PLA2G12A have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding BAX, BAK, LPLA2, LPL, LIPA, PPT1, PLD3, and SMPD1 so that the BAX, BAK, LPLA2, LPL, LIPA, PPT1, PLD3, and SMPD1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding BAX, BAK, LPLA2, LPL, LIPA, PPT1, PLBL2, PLD3, SMPD1, CLU, PRDX1, PLAA, and ACOT13 so that the BAX, BAK, LPLA2, LPL, LIPA, PPT1, PLBL2, PLD3, SMPD1, CLU, PRDX1, PLAA, and ACOT13 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, and PPT1 so that the LPLA2, LPL, and PPT1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA and PPT1 so that the LPLA2, LPL, LIPA and PPT1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding HACH, CES1F/CES-B1L, and LYPLA1 so that the HACH, CES1F/CES-B1L, and LYPLA1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, HACH, CES1F/CES-B1L, and LYPLA1 so that the LPLA2, LPL, LIPA, PPT1, HACH, CES1F/CES-B1L, and LYPLA1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding SMPD1, CES1, PLA1A, and SIAE and PPT1 so that the SMPD1, CES1, PLA1A, and SIAE have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LPL, LIPA, PPT1, HACH, CES1F/CES-B1L, LYPLA1, SMPD1, CES1, PLA1A, and SIAE so that the LPLA2, LPL, LIPA, PPT1, HACH, CES1F/CES-B1L, LYPLA1, SMPD1, CES1, PLA1A, and SIAE have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LMF1, LIPA, PPT1, HACH, CES1F/CES-B1L, and LYPLA1 so that the LPLA2, LMF1, LIPA, PPT1, HACH, CES1F/CES-B1L, and LYPLA1 have reduced or eliminated enzymatic activity.

In certain embodiments, the present disclosure provides a method for reducing or eliminating enzymatic activity in a cell, comprising administering to the cell a genetic engineering system, wherein the genetic engineering system alters the nucleic acid sequence encoding LPLA2, LMF1, APOC2, LIPA, PPT1, HACH, CES1F/CES-B1L, and LYPLA1 so that the LPLA2, LMF1, APOC2, LIPA, PPT1, HACH, CES1F/CES-B1L, and LYPLA1 have reduced or eliminated enzymatic activity. In certain embodiments, the present disclosure provides a method for reducing or eliminating enzymatic activity in a cell, comprising administering to the cell a genetic engineering system, wherein the genetic engineering system alters the nucleic acid sequence encoding LMF1 and APOC2 so that the LMF1 and APOC2 have reduced or eliminated activity.

In certain embodiments, the present disclosure provides a method of producing a product of interest comprising culturing mammalian cells expressing the product of interest, wherein the mammalian cells express the product of interest and have reduced or eliminated activity of PPT1. In certain embodiments, the present disclosure provides a method of producing a product of interest comprising culturing mammalian cells expressing the product of interest, wherein the mammalian cells express the product of interest and have reduced or eliminated activity of LPLA2, LPL, and LIPA. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, PLBL2, PLD3, and SMPD1. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method of producing a product of interest comprising culturing mammalian cells expressing the product of interest, wherein the mammalian cells express the product of interest and have reduced or eliminated activity of BAX, BAK, LPLA2, LPL, LIPA, PPT1, PLD3, and SMPD1. In certain embodiments, the present disclosure provides a method of producing a product of interest comprising culturing mammalian cells expressing the product of interest, wherein the mammalian cells express the product of interest and have reduced or eliminated activity of BAX, BAK, LPLA2, LPL, LIPA, PPT1, PLBL2, PLD3, SMPD1, CLU, PRDX1, PLAA, and ACOT13. In certain embodiments, the present disclosure provides a method of producing a product of interest comprising culturing mammalian cells expressing the product of interest, wherein the mammalian cells express the product of interest and have reduced or eliminated activity of LPLA2, LPL, and PPT1. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA and PPT1. In certain embodiments, the present disclosure provides a method of producing a product of interest comprising culturing mammalian cells expressing the product of interest, wherein the mammalian cells express the product of interest and have reduced or eliminated activity of HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of SMPD1, CES1, PLA1A, and SIAE. In certain embodiments, the present disclosure provides a method of producing a product of interest comprising culturing mammalian cells expressing the product of interest, wherein the mammalian cells express the product of interest and have reduced or eliminated activity of LPLA2, LPL, LIPA, PPT1, HACH, CES1F/CES-B1L, LYPLA1, SMPD1, CES1, PLA1A, and SIAE. In certain embodiments, the present disclosure provides a method of producing a product of interest comprising culturing mammalian cells expressing the product of interest, wherein the mammalian cells express the product of interest and have reduced or eliminated activity of LPLA2, LMF1, LIPA, PPT1, HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of LPLA2, LMF1, APOC2, LIPA, PPT1, HACH, CES1F/CES-B1L, and LYPLA1. In certain embodiments, the present disclosure provides a method of producing a product of interest comprising culturing mammalian cells expressing the product of interest, wherein the mammalian cells express the product of interest and have reduced or eliminated activity of LMF1 and APOC2.

In certain embodiments, the present disclosure provides a method of culturing a population of mammalian cells expressing a product of interest, wherein the mammalian cells have reduced or eliminated activity of PPT1. In certain embodiments, the present disclosure provides a method of culturing a population of mammalian cells expressing a product of interest, wherein the mammalian cells have reduced or eliminated activity of LPLA2, LPL, and LIPA. In certain embodiments, the present disclosure provides a method of culturing a population of mammalian cells expressing a product of interest, wherein the mammalian cells have reduced or eliminated activity of LPLA2, LPL, LIPA, PPT1, PLBL2, PLD3, and SMPD1. In certain embodiments, the present disclosure provides a method of culturing a population of mammalian cells expressing a product of interest, wherein the mammalian cells have reduced or eliminated activity of LPLA2, LPL, LIPA, PPT1, PLBL2, PLD3, SMPD1, PLAA, IAH1, OTUB1, LYPLA2, and PLA2G12A. In certain embodiments, the present disclosure provides a method of culturing a population of mammalian cells expressing a product of interest, wherein the mammalian cells have reduced or eliminated activity of BAX, BAK, LPLA2, LPL, LIPA, PPT1, PLD3, and SMPD1. In certain embodiments, the present disclosure provides a method of culturing a population of mammalian cells expressing a product of interest, wherein the mammalian cells have reduced or eliminated activity of BAX, BAK, LPLA2, LPL, LIPA, PPT1, PLBL2, PLD3, SMPD1, CLU, PRDX1, PLAA, and ACOT13. In certain embodiments, the present disclosure provides a method of culturing a population of mammalian cells expressing a product of interest, wherein the mammalian cells have reduced or eliminated activity of LPLA2, LPL, and PPT1. In certain embodiments, the present disclosure provides a method of culturing a population of mammalian cells expressing a product of interest, wherein the mammalian cells have reduced or eliminated activity of LPLA2, LPL, LIPA and PPT1. In certain embodiments, the present disclosure provides a method of culturing a population of mammalian cells expressing a product of interest, wherein the mammalian cells have reduced or eliminated activity of HACH, CES1F/CES-B1L, and LYPLA1. In certain embodiments, the present disclosure provides a method of culturing a population of mammalian cells expressing a product of interest, wherein the mammalian cells have reduced or eliminated activity of LPLA2, LPL, LIPA, PPT1, HACH, CES1F/CES-B1L, and LYPLA1. In certain embodiments, the present disclosure provides a method of culturing a population of mammalian cells expressing a product of interest, wherein the mammalian cells have reduced or eliminated activity of SMPD1, CES1, PLA1A, and SIAE. In certain embodiments, the present disclosure provides a method of culturing a population of mammalian cells expressing a product of interest, wherein the mammalian cells have reduced or eliminated activity of LPLA2, LPL, LIPA, PPT1, HACH, CES1F/CES-B1L, LYPLA1, SMPD1, CES1, PLA1A, and SIAE. In certain embodiments, the present disclosure provides a method of culturing a population of mammalian cells expressing a product of interest, wherein the mammalian cells have reduced or eliminated activity of LPLA2, LMF1, LIPA, PPT1, HACH, CES1F/CES-B1L, and LYPLA1. In certain embodiments, the present disclosure provides a method of culturing a population of mammalian cells expressing a product of interest, wherein the mammalian cells have reduced or eliminated activity of LPLA2, LMF1, APOC2, LIPA, PPT1, HACH, CES1F/CES-B1L, and LYPLA1. In certain embodiments, the present disclosure provides a method of culturing a population of mammalian cells expressing a product of interest, wherein the mammalian cells have reduced or eliminated activity of LMF1 and APOC2.

7. EXAMPLES

The following examples are merely illustrative of the presently disclosed subject matter and should not be considered as limitations in any way.

Materials and Methods

Construction of Expression Plasmids

Both heavy chain and light chain cDNAs were under the control of Cytomegalovirus immediate-early gene promoter and enhancer (CMV). Each CMV transcriptional start site is followed by splice donor and acceptor sequences, which define introns that are removed from the final transcripts (Lucas et al. 1996).

Antibody Plasmid DNA Construct Configurations

To construct one-plasmid antibody constructs, fragments bearing antibody heavy chain (HC) and light chain (LC) genes were cloned into a vector containing the L3 and 2L sequences as well as a puromycin N-acetyl-transferase (pac) selectable marker. To construct two-plasmid antibody constructs, antibody HC and LC gene fragments were cloned into a front vector containing L3 and LoxFAS sequences, and a back vector containing LoxFAS and 2L sequences and a pac selectable marker. In the two-plasmid system the start codon of pac is at the end of the front vector while the rest of the pac coding sequence is at the beginning of the back vector. All antibody genes were preceded by a CMV promoter and followed by a SV40 poly(A) sequence. A previously described Cre recombinase plasmid (pOG231) was used for all RMCE processes (O'Gorman S, Dagenais NA, Qian M, Marchuk Y. Proc Natl Acad Sci USA. 1997 Dec. 23; 94(26):14602-7).

L3 sequence: 5' ATAACTTCGTATAAAGTCTCCTATACGAAGTTAT

LoxFAS sequence: 5' ATAACTTCGTATAGAAAGGTATATACGAAGTTAT 2L sequence: 5' ATAACTTCGTATAGCATACATTATACGAAGTTAT Cell Culture CHO cells were cultured in a proprietary DMEM/F12-based medium in 125 mL shake flask vessels at 150 rpm, 37° C. and 5% CO2. Cells were passaged with a seeding density of $3 \times 10^5$/mL, every three to four days.

Stable Transfection and Protein Production

CHO cells were transfected using lipofectamine 2000 CD according to the manufacturer's recommendation (Invitrogen, Carlsbad, CA). Transfected cells were centrifuged and seeded into DMEM/F-12-based selective (glutamine-free) medium with various concentrations of methionine sulfoximine (MSX). About three weeks after seeding, individual colonies were picked into 96-well plates. Picked colonies were evaluated for antibody production by taking the supernatant for ELISA analysis. Top clones were scaled-up to produce antibody using a 14-day fed-batch culture process with day 3 temperature shift to 35 degree.

TI Stable Cell Line Development

Expression plasmids were transfected by MaxCyte STX electroporation (MaxCyte, Gaithersburg, MD). Transfected cells were then selected with puromycin and 1-(2'-deoxy-2'-fluoro-1-beta-D-arabinofuranosyl-5-iodo) uracil (FIAU) (Moravek). After pool selection, single cell cloning (SCC) was performed. Clones were screened for antibody titer by an HTRF assay and the highest titer clones were scaled up for further evaluation.

Fed-Batch Production Assay for Cell Culture Performance

Fed-batch production cultures were performed in shake flasks or ambr15 vessels (Sartorius Stedim) with proprietary chemically defined production media. Cells were seeded at $1 \times 10^6$ cells/ml on day 0, with a temperature shift from 37° C. to 35° C. on day 3. Cultures received proprietary feed medium on days 3, 7, and 10. Viable cell count (VCC) and percent viability of cells in culture were measured on days 0, 3, 7, 10, and 14 using a Vi-Cell XR instrument (Beckman Coulter). Glucose and lactate concentrations were measured on days 7, 10 and 14 using a Bioprofile 400 Analyzer (Nova Biomedical). Day 14 titers were determined using protein A affinity chromatography with UV detection.

Expression and Purification of Recombinant Lipases

Plasmids for expression of the enzymes palmitoyl-protein thioesterase 1 (Uniprot Accession G3HN89), N-acylsphingosine amidohydrolase 1 (Uniprot Accession G3GZB2), lipase A (Uniprot Accession G3HQY6), phospholipase A2 Group 15 (Uniprot Accession G3HKV9), acylcarnitine hydrolase (Uniprot Accession G3IIG1), liver carboxylesterase B-1-like protein (Uniprot Accession A0A061IAA7), Lysophospholipase 1 (Uniprot Accession A0A098KXH0), sphingomyelin phosphodiesterase (Uniprot Accession G3IMH4), carboxylesterase 1 (Uniprot Accession A0A061ID92), phospholipase A1 Member A (Uniprot Accession G3I1J5), and sialic acid acetylesterase (Uniprot Accession G3IIB1), fused to C-terminal 6xHis-or dual 6xHis-Flag epitope and driven by the mammalian cytomegalovirus (CMV) promoter, were created by gene synthesis followed by subcloning into the pRK5 expression vector. The expression constructs were verified by DNA sequencing and transiently transfected into CHO cells. Secreted recombinant lipases were harvested on day 10 after transfection and purified by Ni-NTA, size exclusion, and anti-His affinity chromatography. The purified lipases were dialyzed into the desired buffer and stored at −80° C.

Recombinant human lipoprotein lipase (Uniprot Accession Q6IAV0) was purchased from an external vendor for evaluation (R&D Systems Catalog #9888-LL-100).

Evaluation of Polysorbate Degrading Activity in a Subset of Identified HCPs mAb 2 drug substance (DS) was spiked with Palmitoyl-Thioesterase 1 (PPT1), recombinant human lipoprotein lipase (rhLPL), N-Acylsphingosine Amidohydrolase 1 (ASAH1), and Lipase A (LIPA) to final concentrations of 10 pg/mL, 0.6 pg/mL, 10 pg/mL, and 2.5 pg/mL, respectively. These solutions were incubated in an Agilent 1200 autosampler with the temperature controlled to 25° C. At selected time points over the course of 10-15 hours, 20 μL was sampled and injected to determine the PS20 content by mixed-mode HPLC coupled with ELSD.

A bio-pharmaceutically representative formulation buffer (histidine-acetate, pH 6.0, 120 mM sucrose, with 0.02% or 0.04% PS20 (w:v)) was spiked with purified enzymes to the following concentrations: phospholipase A2 Group 15 (LPLA2) at 0.5 μg/mL, acylcarnitine hydrolase (HACH) at 5 μg/mL, liver carboxylesterase B-1-like protein (CES-B1L) at 5 μg/mL, Lysophospholipase 1 (LYPLA1) at 0.5 μg/mL, sphingomyelin phosphodiesterase (SMPD1) at 52 μg/mL, carboxylesterase 1 (CES1) at 50 μg/mL, phospholipase A1 Member A (PLA1A) at 31 μg/mL, and sialic acid acetylesterase (SIAE) at 70 μg/mL. These solutions were incubated in an Agilent 1200 autosampler with the temperature controlled to 25° C. At selected time points over the course of 6-15 hours, 20 μL was sampled and injected to determine the PS20 content by mixed-mode HPLC coupled with ELSD.

Evaluation of Lipase/Esterase Knock Outs (KOs) on Purified mAbs from CHO Cells Using PS20 Degradation Assay The impact of KOs on polysorbate degradation was evaluated by comparing purified mAb samples generated using recombinant mAb-producing CHO cell lines with lipase/esterase genes knocked out against their corresponding mAb-producing CHO cell lines without the genes knocked out. For each mAb, production cultures of the mAb-producing CHO cells were conducted in small-scale (2-L) bioreactors using the same culture conditions. After approximately two weeks in production bioreactors, the cultures were harvested and purified. For each mAb, the culture supernatants were taken through the same downstream processing steps (affinity and polishing chromatography) and conditions to generate purified materials for testing. In this manner, for a given mAb, the purified samples only differed in the use of KO cell or control cells because the upstream and downstream processing steps and conditions were identical. It is important to perform the polysorbate 20 (PS20) degradation assay on purified materials instead of cell culture harvests because the purified materials are more representative of the drug products where polysorbate degradation and particle formation may occur during real-time long-term storage.

To perform the PS20 degradation assay, the purified samples were spiked with PS20 (0.04% v/v) and methionine (20 mg/ml) and incubated at 25° C. for approximately 2 weeks with samples taken at multiple time points. After incubation, the samples were analyzed for PS20 hydrolytic degradation by quantifying the free fatty acid (lauric acid) released from enzymatic cleavage as previously described in detail (Cheng et al., J Pharm Sci, 2019, Volume 108, Issue 9, Pages 2880-2886). The rate of lauric acid release represented the enzymatic activity towards PS20 degradation. The lauric acid release rates for cells with lipase/esterase genes knocked out (i.e., KOs) were compared to the lauric acid release rates for the control cells (i.e., without KOs). The efficacy of KOs towards inhibiting PS20 degradation was evaluated by calculating the percent decrease in the rate of lauric acid release in the mAb samples with genes knocked out relative to the corresponding mAb samples using control cells (FIG. 15). For example, complete inhibition of hydrolytic PS20 degradation in KO cells would result in a 100% decrease in PS20 degradation activity (as represented by lauric acid release rate).

Example 1: 28 Enzymes Found in Enriched Samples of Three Monoclonal Antibodies

FIG. 1 identifies 28 enzymes were found in enriched mAb-1, mAb-2 and mAb-3 samples taken from different stages in the purification process. The 28 enzymes include lipases, esterases and hydrolases. In the mAb-1 samples were found 18 enzymes. In the mAb-2 samples were found 15 enzymes. Additionally, in the mAb-3 samples, eight enzymes were found.

Example 2: Multiplexed KO Approach for the Generation of Blank CHO Host Cells

Blank CHO cell line hosts with single or multiple knockout genes were generated from a Parental CHO Host cell line using an approach as shown in FIG. 2. The 1× KO hosts were generated from the Parental Host wherein the PLBL2 gene is knocked out. For the generation of the 3× hosts from the Parental host, the LPLA2, LPL and Lipase A genes were simultaneously knocked out. For the generation of the 7× hosts from the 3× hosts, the PPT1, PLD3, PLBL2, and SMPD1 genes were additionally knocked out. For the generation of the 12× hosts from the 7× hosts, the PLAA, LAH1, OTUB1, LYPLA2, and PLA2G12a genes were additionally knocked out. The Bax-Bak KO hosts were generated by using the Parental host and by knocking out the Bax and Bak genes. For the generation of the 8× hosts from the Bax-Bak KO hosts, the LPLA2, LPL, Lipase A, PPT1, PLD3, and SMPD1 genes were additionally knocked out. For the generation of the 13× hosts from the 8× KO hosts, the Clu, PRDX1, Plaa, and Acot13 genes were additionally knocked out. The knocked-out genes of each KO host cell line are listed in FIG. 3.

Example 3: PLBL2 KO Cells have Comparable Cell Growth and Productivity to Parental CHO Host Cell Line A cultured seed train of the mAb-A expressing cell lines was used to source production cultures in bioreactors using standard or enhanced feeding strategies. Growth and viability of 1× KO and parental CHO cell lines were shown in FIGS. 4A and 4C. Titer of the 1× KO cell lines (FIG. 4B) was comparable or better to the parental CHO host cell.

Example 4: Cell Growth of 3-Lipase/Esterase Knocked Out CHO Cell Lines

The effect of the knockout of three (3× KO) lipase/esterases on CHO cell lines growth and expression of mAb-B was evaluated. The cell growth of the 3× KO cell line was compared to the parental CHO cell line. The growth (represented as the integral of viable cell count, IVCC) of the 3× KO cell line expressing mAb-B is depicted in FIG. 5A. Titer and Specific Productivity (Qp) are depicted in FIGS. 5B and 5C, respectively.

Example 5: Cell Growth of 7-Lipase/Esterase Knocked Out CHO Cell Lines

The effect of the knockout of seven (7× KO) lipase/esterases on CHO cell lines growth was evaluated. The cell growth of a 7× KO cell line was compared to the parental CHO cell line showing that the growth (represented as the integral of viable cell count, IVCC) of the 7× KO cell host was comparable to the parental CHO cell line (FIG. 6A). The viability and the lactate accumulation of the 7× KO host are depicted in FIGS. 6B and 6C, respectively.

Example 6: Production of 3 Different Antibodies in 7× Knockout CHO Cell Lines

The effect of the 7× KO on the expression of three different antibodies was also evaluated. Growth (FIG. 7A), titer (FIG. 7B) and product specificity (FIG. 7C) of the 7× KO cell line for the three different antibodies was comparable or better to the parental CHO host cell.

Example 7: Cell Growth of 8-Lipase/Esterase Knocked Out CHO Cell Lines

The effect of the knockout of eight (8× KO) lipase/esterases on CHO cell lines growth was evaluated. The cell growth of the Bax Bak KO Host and the 8× KO cell line was compared to the parental CHO cell line showing that the growth (represented as the integral of viable cell count, IVCC) of the 8× KO and the Bax Bak KO cell host was comparable to the parental CHO cell lines (FIG. 8A) The viability and the lactate accumulation of the 8× KO and the Bax Bak KO hosts are depicted in FIGS. 8B and 8C, respectively.

Example 8: Cell Growth of 12-Lipase/Esterase Knocked Out CHO Cell Lines

The effect of the knockout of twelve (12× KO) lipase/esterases on CHO cell lines growth was evaluated. The day 13 (D13) cell growth of 12× KO cell lines were compared to the parental CHO cell line, the 3× KO and the 7× KO hosts showing that the growth (represented as the integral of viable cell count, IVCC) of the 12× KO cell hosts was comparable to the parental CHO cell lines (FIG. 9A). The D13 viability and the lactate accumulation of the 12× KO hosts are depicted in FIGS. 9B and 9C respectively.

Example 9: Production of mAb-2 in 7× Knockout CHO Cell Lines

The effect of the 7× KO on the expression of mAb-2 was also evaluated. Average D10 titer (FIG. 10A), D10 and D14 growth (FIG. 10B), product specificity at D10 (FIG. 10C) and D14 lactate accumulation (FIG. 10D) of the 7× KO cell lines for the mAb-2 was comparable to the parental CHO host cell.

Example 10: Production of mAb-1 in 7× Knockout CHO Cell Lines

The effect of the 7× KO on the expression of mAb-1 was also evaluated. Titer (FIG. 11A), growth (FIG. 11B) and product specificity (FIG. 11C) of the 7× KO cell lines for the mAb-2 was comparable to the parental CHO host cell.

Example 11: PS20 Degradation in 7× Lipase/Esterase Knockout CHO Cell Lines

The effect of seven (7× KO) lipase/esterase knockout on PS20 degradation was evaluated on mAb-B producing cell lines. These cell lines were generated by transfecting the 7× KO CHO host (FIG. 3) to produce mAb-B. After culturing the cells in bioreactors, the cell culture harvests were processed through affinity and polishing chromatography steps. The PS20 degradation was reduced 61% in the 7× KO lipase cell lines compared to the parental CHO cell line (FIG. 12) in the purified materials obtained at the end of downstream processing. Reduced degradation of PS20 may enable significant purification process optimizations and more importantly, it lowers the risk of particle formation in drug products.

Example 12: Characterization of Recombinant LIPA, ASAH1, LPL, PPT1, LPLA2, HACH, CES-B1L, SMPD1, CES1, PLA1A, and SIAE Taking previous reports of PS-hydrolyzing enzymes as well the structural resemblance of triglycerides and polysorbate into account, LIPA, ASAH1, LPL, and PPT1 were selected to assess the degradation characteristics of polysorbate-hydrolyzing enzymes in more detail. CHO LIPA, ASAH1, PPT1, LPLA2, HACH, CES-B1L, SMPD1, CES1, PLA1A, and SIAE were expressed as His-tagged constructs in CHO cells and purified as described in the Methods section. SDS-PAGE for each enzyme is shown in FIG. 13 and all enzymes were confirmed as the protein of interest by intact mass MS (data not shown). It should also be mentioned that the recombinant human LPL (rhLPL) was purchased from a commercial source whereas all other enzymes tested were from *C. griseus*.

Figure 14A:
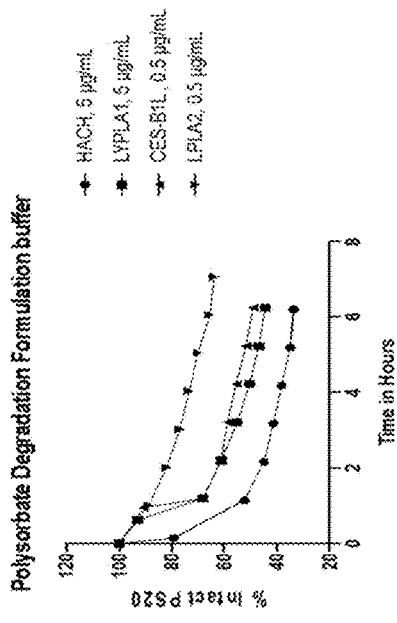
Figure 14B:
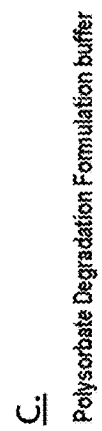
Figure 14C:
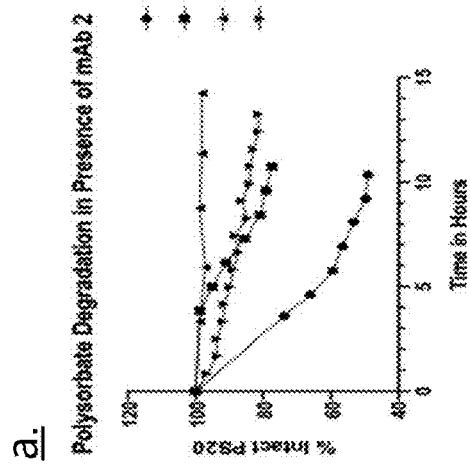

These enzymes were further characterized for their ability to degrade polysorbate. Each enzyme was spiked into a polysorbate-containing mAb formulation. The enzyme activity was measured by measuring the polysorbate concentration as a function of time. Ultimately, it was shown that PPT1, LIPA, and rhLPL (at 10 µg/mL, 10 µg/mL, and 0.6 µg/mL, respectively) were able to degrade polysorbate within the timeframe tested, 10-15 hrs, whereas ASAH1 at 2.5 µg/mL did not show measurable degradation as shown in FIG. 14a. It was also shown that HACH, LYPLA1, CES-B1L, and LPLA2 (at 5 µg/mL, 5 µg/mL, 0.5 µg/mL, and 0.5 µg/mL, respectively) were also able to degrade polysorbate in solutions of formulation buffer (FIG. 14b). The additional set of hydrolytic enzymes, PLA1A, SIAE, CES1, and SMPD1 (at 31 µg/mL, 70 µg/mL, 50 µg/mL, and 52 µg/mL, respectively) were also able to degrade polysorbate in solutions of formulation buffer, but higher concentrations of these recombinantly expressed enzymes were required to degrade polysorbate (FIG. 14c).

Example 13: PS20 Degradation in Additional 7× and 12× Lipase/Esterase Knockout CHO Cell Lines The effect of knocking out seven (7× KO) and twelve (12× KO) genes in CHO cells lines on PS20 degradation was evaluated in 4 additional mAb producing cell lines. These cell lines were generated by transfecting the 7× KO or 12× KO CHO hosts (FIG. 3) to produce the desired mAb. The effect of 7× KO was tested with mAb W and mAb X cell lines, and the effect of 12× KO was tested with mAb Y and mAb Z cell lines. After culturing the cells in bioreactors, the cell culture harvests were processed through affinity and polishing chromatography steps. In all cases, the materials generated at the end of purification showed decreased enzymatic activity towards PS20 degradation for the 7× KO and 12× KO cell lines relative to the control cell lines without any genes knocked out (FIG. 15). Reduced degradation of PS20 may enable significant purification process optimizations and more importantly, it lowers the risk of particle formation in drug products.

Example 14: PS20 Degradation in mAb T Cell Line with Multiple Lipase/Esterase Genes Knocked Out The effect of knocking out lipase/esterase genes in a recombinant CHO cell line producing mAb T on PS20 degradation was evaluated. These cell lines were generated by sequentially knocking out lipase/esterase genes from the recombinant mAb T producing CHO cell line, The effects of 1× KO (LPLA2) and 2× KO (LPLA2 and LPL) on the cell lines were tested first. Then the effects of 3× KO (LPLA2, LPL and LIPA) and 6× KO (LPLA2, LPL, LIPA, PPT1, PLD3 and PLBL2) on the cell lines were tested thereafter. After culturing the cells in bioreactors, the cell culture harvests were processed through affinity and polishing chromatography steps. In all cases, the materials generated at the end of purification showed decreased enzymatic activity towards PS20 degradation for the 1× KO, 2× KO, 3× KO and 6× KO cell lines relative to the control parental mAb T cell line without any genes knocked out (FIG. 16). The second set of experiment with the 3× KO and 6× KO cell lines showed lower PS20 degrading activity than the first set of experiment with the 1× KO and 2× KO cell lines. Taken together, these results indicate the potential benefits of knocking out multiple relevant lipase/esterase genes that express polysorbate-degrading enzymes. Reduced degradation of PS20 may enable significant purification process optimizations and more importantly, it lowers the risk of particle formation in drug products.

The contents of all figures and all references, patents and published patent applications and Accession numbers cited throughout this application are expressly incorporated herein by reference.

What is claimed is:

1. A recombinant host cell, wherein the cell is modified to reduce or eliminate the activity of a plurality of enzymes relative to the activity of the enzymes in an unmodified cell, wherein the enzymes are Phospholipase A2 group XV (LPLA2); Lipoprotein lipase (LPL); Lipase A (Lysosomal acid lipase ester hydrolase, Lipase) (LIPA); Palmitoyl-protein thioesterase 1 (PPT1); phospholipase B-domain containing 2 (PLBL2 PLBD2); Phospholipase D3 (PLD3); and Sphingomyelin phosphodiesterase (SMPD1).

2. The recombinant host cell of claim 1, wherein the activity of the enzymes is reduced or eliminated by:
   a. knocking down expression of the enzymes;
   h. or knocking out expression of the enzymes; or
   c. altering the nucleic acid sequence encoding the enzymes.

3. The recombinant host cell of claim 1, wherein the cell comprises a plurality of altered enzyme genes.

4. The recombinant host cell of claim 3, wherein the altered enzyme genes have no detectable enzymatic activity.

5. The recombinant host cell of claim 1, wherein the cell is a mammalian cell.

6. The recombinant host cell of claim 5, wherein the cell is a CHO cell.

7. The recombinant host cell of claim 1, comprising a nucleic acid sequence encoding a product of interest.

8. The recombinant host cell of claim 7, wherein the product of interest comprises a protein, a viral particle or a viral vector.

9. The recombinant host cell of claim 7, wherein the product of interest comprises a recombinant protein.

10. The recombinant host cell of claim 7, wherein the product of interest comprises an antibody or an antigen-binding fragment thereof.

11. The recombinant host cell of claim 7, wherein the nucleic acid sequence is integrated in the cellular genome of the mammalian cell at a targeted location.

12. The recombinant host cell of claim 11, further comprising a second nucleic acid sequence encoding the product of interest, which is randomly integrated in the cellular genome of the mammalian cell.

13. The recombinant host cell of claim 1, wherein the modified cell does not express any detectable LPL; PLBL2/PLBD2; LIPA; PLD3; LPLA2.

14. A composition comprising a recombinant host cell of claim 1.

* * * * *